United States Patent
Linschoten et al.

(10) Patent No.: US 7,071,175 B1
(45) Date of Patent: Jul. 4, 2006

(54) PYRIDINE MERCAPTO CARBOXYLIC ACIDS AS CARBOXYPEPTIDASE U INHIBITORS

(75) Inventors: Marcel Linschoten, Västra Frölunda (SE); Magnus Polla, Gothenburg (SE)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 09/600,661

(22) PCT Filed: May 3, 2000

(86) PCT No.: PCT/SE00/00834

§ 371 (c)(1),
(2), (4) Date: Jul. 20, 2000

(87) PCT Pub. No.: WO00/66557

PCT Pub. Date: Nov. 9, 2000

(30) Foreign Application Priority Data

May 3, 1999 (SE) .............................. 9901573

(51) Int. Cl.
*C07D 213/72* (2006.01)
*C07D 213/74* (2006.01)
*A61K 31/44* (2006.01)
*A61P 7/02* (2006.01)

(52) U.S. Cl. .......................... 514/63; 514/89; 514/277; 514/340; 514/345; 514/352; 514/354; 514/357; 546/13; 546/22; 546/268.4; 546/301; 546/309; 546/323; 546/341

(58) Field of Classification Search .................. 514/63, 514/89, 277, 340, 345, 352, 354, 357; 546/13, 546/22, 268.4, 301, 309, 323, 341
See application file for complete search history.

(56) References Cited

U.S. PATENT DOCUMENTS

| | | | | |
|---|---|---|---|---|
| 3,091,569 A | | 5/1963 | Sheffner ...................... | 167/58 |
| 3,766,206 A | | 10/1973 | Hess et al ................... | 260/305 |
| 4,113,715 A | | 9/1978 | Ondetti et al. ............ | 260/112.5 |
| 4,177,277 A | | 12/1979 | Ondetti et al. .............. | 424/263 |
| 4,537,727 A | | 8/1985 | Barton et al. ................ | 260/455 |
| 5,254,579 A | | 10/1993 | Poli et al. .................... | 514/423 |
| 5,506,259 A | * | 4/1996 | Norcini et al. .............. | 514/423 |

FOREIGN PATENT DOCUMENTS

| | | |
|---|---|---|
| DE | 3838467 | 5/1990 |
| EP | 0136883 | 4/1985 |
| EP | 0300100 | 1/1989 |
| EP | 0318859 | 6/1989 |
| EP | 0361365 | 4/1990 |
| EP | 0470686 | 2/1992 |
| EP | 0636621 | 2/1995 |
| EP | 0852225 | 7/1998 |
| FR | 1393338 | 2/1965 |
| FR | 2266502 | 10/1975 |
| FR | 2430945 | 2/1980 |
| GB | 1593469 | 7/1981 |
| JP | 01254654 A2 | * 10/1989 |
| RU | 2055834 | 3/1996 |
| WO | WO 93/08181 | 4/1993 |

OTHER PUBLICATIONS

Chemical Abstracts Documents No. 112:197646, abstract of JP 01254654 A2.*
Boffa, M.B. et al, Curr Drug Targets Cardiovasc Haematol Disord. Dec. 2001;1(2):59–74., Medline abstract PMID: 12769657.*
U.S. Appl. No. 09/600,660, filed Jul. 20, 2000, Linschoten et al.
U.S. Appl. No. 09/600,659, filed Jul. 20, 2000, Abrahamsson et al.
Chem. Abstr. 116: 83328, Mimura, et al., J. Med. Chem. 35, 602–608 (1992).
Derwent Abstr. 89–211491/29, JP 01149763 to Dainippon Pharm. KK (1989).
Hirsh, et al., CHEST 2001; 119:1S–2S.
Geerts, et al., CHEST 2001; 119:132S–175S.
Albers, et al., CHEST 2001; 119:194S–206S.
Cairns, et al., CHEST 2001; 119:228S–252S.
Albers, et al., CHEST 2001; 119:300S–320S.
Cohen, Seminars in Thrombosis and Hemostasis 28, suppl. 3, 13–17 (2002).
Barrow et al., J. Med. Chem. 46, 5294–5297 (2003).
Muto et al., Eur. J. Pharmacol. 461, 181–189 (2003).
Suzuki et al., J. Pharmacol. Exper. Ther. 309, 607–615 (2004).
Hashimoto et al., Thromb. Haemost. 87, 110–113 (2002).
Wu et al., Thromb. Haemost. 90, 414–421 (2003).
Nagashima et al., Thromb. Res. 98, 333–342 (2000).
Redlitz et al. Circulation 93, 1328–1330 (1996).
2HU et al, Isolation and characterization of americnin, a specific inhibitor of thrombin, from the salivary glands of the lone star tick Amblyomma americanum (L.), Exp. Parasitol. 87, 30–38 (1997) (abstract only).

* cited by examiner

Primary Examiner—Thomas C. McKenzie
(74) Attorney, Agent, or Firm—White & Case LLP

(57) ABSTRACT

The present invention relates to compounds of Formula I, and pharmaceutically acceptable salts or solvates thereof, or solvates of such salts,

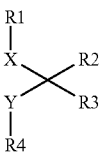

(I)

which compounds inhibit carboxypeptidase U and thus can be used in the prevention and treatment of diseases associated with carboxypeptidase U. In further aspects, the invention relates to compounds of the invention for use in therapy; to processes for preparation of such new compounds: to pharmaceutical compositions containing at least one compound of the invention, or a pharmaceutically acceptable salt or solvate thereof, as active ingredient; and to the use of the active compounds in the manufacture of medicaments for the medical use indicated above.

23 Claims, No Drawings

PYRIDINE MERCAPTO CARBOXYLIC ACIDS AS CARBOXYPEPTIDASE U INHIBITORS

FIELD OF THE INVENTION

The present invention relates to novel compounds, and pharmaceutically acceptable salts thereof, which inhibit basic carboxypeptidases, more specifically carboxypeptidase U, and thus can be used in the prevention and treatment of diseases wherein inhibition of carboxypeptidase U is beneficial. In further aspects, the invention relates to compounds of the invention for use in therapy; to processes for preparation of such new compounds; to pharmaceutical compositions containing at least one compound of the invention, or a pharmaceutically acceptable salt thereof, as active ingredient; and to the use of the active compounds in the manufacture of medicaments for the medical use indicated above.

BACKGROUND OF THE INVENTION

Fibrinolysis is the result of a series of enzymatic reactions resulting in the degradation of fibrin by plasmin. The activation of plasminogen is the central process in fibrinolysis. The cleavage of plasminogen to produce plasmin is accomplished by the plasminogen activators, tissue-type plasminogen activator (t-PA) or urokinase-type plasminogen activator (u-PA). Initial plasmin degradation of fibrin generates carboxy-terminal lysine residues that serves as high-affinity binding sites for plasminogen. Since plasminogen bound to fibrin is much more readily activated to plasmin than free plasminogen, this mechanism provides a positive feedback regulation of fibrinolysis.

One of the endogenous inhibitors to fibrinolysis is carboxypeptidase U (CPU). CPU is also known as plasma carboxypeptidase B, active thrombin activatable fibrinolysis inhibitor (TAFIa), carboxypeptidase R and inducable carboxypeptidase activity. CPU is formed during coagulation and fibrinolysis from its precursor proCPU by the action of proteolytic enzymes e.g. thrombin, thrombin-thrombomodulin complex or plasmin. CPU cleaves basic amino acids at the carboxy-terminal of fibrin fragments. The loss of carboxy-terminal lysines and thereby of lysine binding sites for plasminogen then serves to inhibit fibrinolysis.

By inhibiting the loss of lysine binding sites for plasminogen and thus increasing the rate of plasmin formation, effective inhibitors of carboxypeptidase U would be expected to facilitate fibrinolysis.

2-mercaptomethyl-3-guanidinoethylthiopropanoic acid is reported as a carboxypeptidase N inhibitor. More recently, this compound has been shown to inhibit CPU, Hendriks, D. et al., Biochimica et Biophysica Acta, 1034 (1990) 86–92.

Guanidinoethylmercaptosuccinic acid is reported as a carboxypeptidase N inhibitor. More recently, this compound has been shown to inhibit CPU, Eaton, D. L., et al., The Journal of Biological Chemistry, 266 (1991) 21833–21838.

DISCLOSURE OF THE INVENTION

It has surprisingly been found that compounds of the Formula I are particularly effective as inhibitors of carboxypeptidase U and thereby useful as medicaments for the treatment or prophylaxis of conditions wherein inhibition of carboxypeptidase U is beneficial.

In one aspect, the invention thus relates to compounds of the general Formula I,

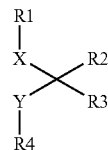

(I)

or a pharmaceutically acceptable salt or solvate thereof, or a solvate of such a salt,
wherein $R_1$ represents,
  $C_1$–$C_6$ alkyl, substituted with one or more basic groups such as amino, amidino and/or guanidino;
  cycloalkyl, substituted with one or more basic groups such as amino, amidino and/or guanidino;
  heterocyclyl, containing at least one nitrogen atom;
  heterocyclyl, containing at least one hetero atom selected from S or O, and substituted with one or more basic groups such as amino, amidino and/or guanidino;
  or aryl, substituted with one or more basic groups such as amino, amidino and/or guanidino, $R_2$ represents H, acyl, acylamino, alkyl, alkylcarbamoyl, alkylthio, alkoxy, aroyl, aroylamino, aryloxy, arylthio, amidino, amino, aryl, carbamoyl, carboxy, cyano, cycloalkyl, formyl, guanidino, halogen, heterocyclyl, hydroxy, oxo, nitro, thiol, $Z_2N$—CO—, ZO—CO—NZ— or $Z_2N$—CO—NZ— group, $R_3$ represents $COOR_5$, $SO(OR_5)$, $SO_3R_5$, P=$O(OR_5)_2$, $B(OR_5)_2$, P=$OR_5(OR_5)$, or tetrazole, or any carboxylic acid isostere, R represents SH, S—CO—$C_1$–$C_6$ alkyl or S—CO-aryl, $R_5$ represents H, $C_1$–$C_6$ alkyl or aryl, $R_6$ represents H or $C_1$–$C_6$ alkyl, X represents O, S, SO, $SO_2$, $C(Z)_2$, N(Z), $NR_6SO_2$, $SO_2NR_6$, $NR_6CO$ or $CONR_6$, Y represents $C(Z)_2$, Z represents independently H, $C_1$–$C_6$ alkyl, aryl, cycloalkyl or heterocyclyl.

Preferred compounds according to the present invention are those of Formula I, or a pharmaceutically acceptable salt or solvate thereof, or a solvate of such a salt,
wherein $R_1$ represents,
  cycloalkyl, substituted with one or more basic groups such as amino, amidino and/or guanidino;
  heterocyclyl, containing at least one nitrogen atom;
  heterocyclyl, containing at least one hetero atom selected from S or O, and substituted with one or more basic groups such as amino, amidino and/or guanidino;
  or aryl, substituted with one or more basic groups such as amino, amidino and/or guanidino;

$R_2$ represents H, acyl, acylamino, alkyl, alkylcarbamoyl, alkylthio, alkoxy, aroyl, aroylamino, aryloxy, arylthio, amidino, amino, aryl, carbamoyl, carboxy, cyano, cycloalkyl, formyl, guanidino, halogen, heterocyclyl, hydroxy, oxo, nitro, thiol, $Z_2N$—CO—O—, ZO—CO—NZ— or $Z_2N$—CO—NZ— group, $R_3$ represents $COOR_5$, $R_4$ represents SH, S—CO—$C_1$–$C_6$ alkyl or S—CO-aryl, $R_5$ represents H, $C_1$–$C_6$ alkyl or aryl, $R_6$ represents H or $C_1$–$C_6$ alkyl, X represents O, S, SO, $SO_2$, $C(Z)_2$, N(Z), $NR_6SO_2$, $SO_2NR_6$ or $CONR_6$, Y represents $C(Z)_2$, Z represents independently H, $C_1$–$C_6$ alkyl, aryl, cycloalkyl or heterocyclyl.

More preferred compounds according to the present invention are those of Formula I, or a pharmaceutically acceptable salt or solvate thereof, or a solvate of such a salt, wherein $R_1$ represents,
  cycloalkyl, substituted with one or more basic groups such as amino, amidino and/or guanidino;
  heterocyclyl, containing at least one nitrogen atom;
  heterocyclyl, containing at least one hetero atom selected from S or O, and substituted with one or more basic groups such as amino, amidino and/or guanidino;
$R_2$ represents H, $C_1$–$C_3$ alkyl, amino, halogen or hydroxy,
$R_3$ represents $COOR_5$,
$R_4$ represents SH, S—CO—$C_1$–$C_6$ alkyl or S—CO-aryl,
$R_5$ represents H, $C_1$–$C_6$ alkyl or aryl,
X represents $C(Z)_2$,
Y represents $C(Z)_2$,
Z represents independently H or $C_1$–$C_6$ alkyl.

Even more preferred compounds according to the present invention are those of Formula I, or a pharmaceutically acceptable salt or solvate thereof, or a solvate of such a salt, wherein $R_1$ represents,
  cycloalkyl, substituted with one or more basic groups such as amino, amidino and/or guanidino;
  heterocyclyl, containing at least one nitrogen atom;
$R_2$ represents H, F, or C, alkyl,
$R_3$ represents $COOR_5$,
$R_4$ represents SH, S—CO—$C_1$–$C_6$ alkyl or S—CO-aryl,
$R_5$ represents H, $C_1$–$C_6$ alkyl or aryl,
X represents $C(Z)_2$,
Y represents $C(Z)_2$,
Z represents independently H or $C_1$–$C_6$ alkyl.

Most preferred compounds according to the present invention are those of Formula I or a pharmaceutically acceptable salt or solvate thereof, or a solvate of such a salt, wherein $R_1$ represents cyclopentyl, pyridyl, pyrimidinyl, piperidinyl or thiazolyl,
$R_2$ represents H, F, or $C_1$ alkyl,
$R_3$ represents $COOR_5$,
$R_4$ represents SH,
$R_5$ represents H.
X represents CHZ,
Y represents CHZ,
Z represents independently H or $C_1$–$C_6$ alkyl.

The following definitions shall apply throughout the specification and the appended claims:

The term "basic group" denotes a basic group, wherein the conjugate acid of said basic group has a pKa of from about −5 to about 25, preferably of from 1 to 15.

The term "carboxylic acid isostere" denotes an acidic group having a pKa of from about −5 to about 25, preferably of from 1 to 15.

The term "$C_1$–$C_6$ alkyl" denotes a straight or branched, saturated or unsaturated, substituted or unsubstituted alkyl group having 1 to 6 carbon atoms in the chain wherein the alkyl group may optionally be interrupted by one or more heteroatoms selected from O, N or S. Examples of said alkyl include, but is not limited to, methyl, ethyl, ethenyl, ethynyl, n-propyl, iso-propyl, propenyl, iso-propenyl, propynyl, n-butyl, iso-butyl, sec-butyl, t-butyl, butenyl, iso-butenyl, butynyl and straight- and branched-chain pentyl and hexyl.

The term "$C_1$–$C_3$ alkyl" denotes a straight or branched, saturated or unsaturated, substituted or unsubstituted alkyl group having 1 to 3 carbon atoms in the chain wherein the alkyl group may optionally be interrupted by one or more heteroatoms selected from O, N or S. Examples of said alkyl include, but is not limited to, methyl, ethyl, ethenyl, ethynyl, n-propyl, iso-propyl, propenyl, iso-propenyl, propynyl.

The term "$C_1$ alkyl" denotes a substituted or unsubstituted alkyl group having 1 carbon atom. An example of said alkyl include, but is not limited to, methyl, The term "$C_1$–$C_6$ alkoxy" denotes an alkyl-O-group, wherein $C_1$–$C_6$ alkyl is as defined above.

The term "$C_1$–$C_3$ alkoxy" denotes an alkyl-O-group, wherein $C_1$–$C_3$ alkyl is as defined above.

The term "heterocyclyl" denotes a substitued or unsubstituted, 4- to 10-membered monocyclic or multicyclic ring system in which one or more of the atoms in the ring or rings is an element other than carbon, for example nitrogen, oxygen or sulfur, especially 4-, 5- or 6-membered aromatic or aliphatic heterocyclic groups, and includes, but is not limited to, azetidine, furan, thiophene, pyrrole, pyrroline, pyrrolidine, dioxolane, oxthiolane, oxazolane, oxazole, thiazole, imidazole, imidazoline, imidazolidine, pyrazole, pyrazoline, pyrazolidine, isoxazole, isothiazole, oxadiazole, furazan, triazole, thiadiazole, pyran, pyridine, piperidine, dioxane, morpholine, dithiane, oxathiane, thiomorpholine, pyridazine, pyrimidine, pyrazine, piperazine, triazine, thiadiazine, dithiazine, azaindole, azaindoline, indole, indoline, naphthyridine groups, and shall be understood to include all isomers of the above identified groups. The term "azetidinyl" shall for example be understood to include the 2-, and 3-isomers and the terms "pyridyl" and "piperidinyl" shall for example be understood to include the 2-, 3-, and 4-isomers.

The term "cycloalkyl" denotes a saturated or unsaturated, substituted or unsubstituted, non-aromatic ring composed of 3, 4, 5, 6 or 7 carbon atoms, and includes, but is not limited to, cyclopropyl, cyclobutyl, cyclopentyl, cyclohexyl, cycloheptyl, cyclobutenyl, cyclopentenyl, cyclohexenyl, cycloheptenyl, cyclopentadienyl, cyclohexadienyl and cycloheptadienyl groups.

The term "halogen" includes fluoro, chloro, bromo and iodo groups.

The term "aryl" denotes a substituted or unsubstituted $C_6$–$C_{14}$ aromatic hydrocarbon and includes, but is not limited to, phenyl, naphthyl, indenyl, anthracenyl, phenanthrenyl, and fluorenyl.

The term "aryloxy" denotes an aryl-O-group, wherein aryl is as defined above.

The term "acyl" denotes an alkyl-CO-group, wherein alkyl is as defined above.

The term "aroyl" denotes an aryl-CO-group, wherein aryl is as defined above.

The term "alkylthio" denotes an alkyl-S-group, wherein alkyl is as defined above.

The term "arylthio" denotes an aryl-S-group, wherein aryl is as defined above.

The term "aroylamino" denotes an aroyl-N(Z)-group, wherein aroyl and Z are as defined above.

The term "acylamino" denotes an acyl-N(Z)-group, wherein acyl and Z are as defined above.

The term "carbamoyl" denotes a $H_2N$—CO-group.

The term "alkylcarbamoyl" denotes a $Z_2N$—CO-group wherein Z is as defined above.

The term "substituted" denotes an "$C_1$ alkyl", "$C_1$–$C_3$ alkyl", "$C_1$–$C_6$ alkyl", "cycloalkyl", "heterocyclyl" or a "aryl" group as defined above which is substituted by one or more acyl, acylamino, alkyl, alkylcarbamoyl, alkylthio, alkoxy, aroyl, aroylamino, aryloxy, arylthio, amidino, amino, aryl, carbamoyl, carboxy, cyano, cycloalkyl, formyl, guanidino, halogen, heterocyclyl, hydroxy, oxo, nitro, thiol, thio, $Z_2N$—CO—O—, ZO—CO—NZ—, or $Z_2N$—CO—NZ— groups.

Moreover, the compounds of Formula I wherein $R_4$ is mercapto may be present in the form of a dimer which is bonded via —S—S-bond, which is also included in this invention.

Both the pure enantiomers, racemic mixtures and unequal mixtures of two enantiomers are within the scope of the present invention. It should also be understood that all the diastereomeric forms possible are within the scope of the invention. Also included in the invention are derivatives of the compounds of the Formula I which have the biological function of the compounds of Formula I, such as prodrugs.

Depending on the process conditions the compounds of Formula I are obtained either in neutral or salt form or as a solvate, e.g. a hydrate, and are all within the scope of the present invention.

Preparation

The present invention also provides the processes A–C for the manufacture of compounds with the general Formula I.

Process A

Process A for manufacture of compounds with the general Formula I, wherein $R_1$, $R_3$, $R_4$, and Y are as defined above and $R_2$ is H, and X is $C(Z)_2$, comprises the following steps:

a) Compounds of the general Formula II,

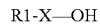  (II)

wherein $R_1$, is as defined for Formula I and X is $C(Z)_2$, which are either commercially available or are available using known techniques, can be converted into a compound of the general Formula III,

  (III)

wherein L is a suitable leaving group, such as chloro, bromo, iodo, triflate or tosyl, under standard conditions using a suitable reagent, such as $PPh_3/CBr_4$, TosCl/pyridine or $(CF_3SO_2)_2O$/TEA.

b) Compounds of the general Formula III can thereafter be reacted with compounds of the general Formula IV,

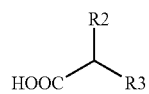  (IV)

wherein $R_2$ and $R_3$ are as defined for Formula I, which are either commercially available, or are available using known techniques, in the presence of a suitable base, such as $K_2CO_3$ or NaH, under standard conditions to give compounds of the general Formula V.

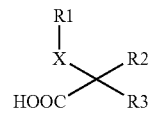  (V)

(c) Compounds of the general Formula V wherein $R_1$ and $R_3$ are as defined for Formula I and X is $C(Z)_2$ and $R_2$ is H can thereafter be converted to compounds of the general Formula VI,

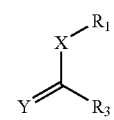  (VI)

by treatment with formaldehyde in the presence of a suitable base, such as $Et_2NH$, under standard conditions.

d) Compounds of the general Formula VI can also be prepared by treating compounds of the general Formula VII,

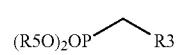  (VII)

wherein $R_3$ and $R_5$ are as defined for Formula I, with an alkylating agent of the general Formula III in the presence of a suitable base, such as LDA or NaH, under standard conditions to give compounds of the general Formula VIII,

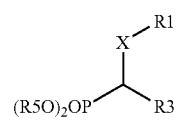  (VIII)

e) Compounds of the general Formula VIII can thereafter be reacted with an appropriate aldehyde or ketone $OC(Z)_2$, in the presence of a suitable base, such as KOtBu, LDA or NaH, under standard conditions to give a compound of the general Formula VI.

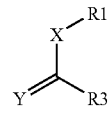  (VI)

f) Compounds of the general Formula VI can be further reacted with compounds of the general Formula IX,

  (IX)

wherein $R_5$ is a suitable protecting group, such as Ac, Bz, PMB or Bn, alone or in the presence of a suitable base, such as NaOMe, NaH or triethylamine or alternatively in the presence of a free-radical initiator, such as AIBN under standard conditions to give compounds of the general Formula I, wherein $R_1$, $R_3$, $R_4$, and Y are as defined for Formula I and $R_2$ is H and X is $C(Z)_2$.

Process B

Process B for manufacture of compounds with the general Formula I, wherein $R_1$, $R_2$, $R_3$, and $R_4$, are as defined in Formula I and Y is $CH_2$, and X is O, S, SO, $SO_2$, $C(Z)_2$, or N(Z), comprises the following steps:

a) Reacting a compound of the general Formula X,

 (X)

wherein $R_1$ is as defined for Formula I and X is O, S, or N(Z), with an alkylating agent of the general Formula XI,

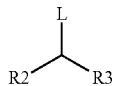 (XI)

wherein $R_2$ and $R_3$ are as defined for Formula I and L is a suitable leaving group, such as a chloro, bromo, iodo, triflate or tosylate group, under standard conditions using suitable reagents, such as NaH, $Ag_2CO_3$, or $Bu_4NHSO_4$/NaOH, to give compounds of the general Formula XII,

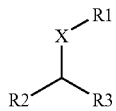 (XII)

b) Compounds of the general Formula XII can thereafter be reacted with carbon dioxide in the presence of a suitable base, such as LDA or KHMDS under standard conditions to give a compound of the general Formula XIII,

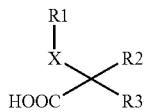 (XIII)

(c) Compounds of the general Formula XIII can thereafter be reacted with an alkyl chloroformate, such as ClCOOMe in the presence of a base, such as triethylamine, and thereafter reducing the formed mixed anhydride with a suitable reducing agent, such as $NaBH_4$, under standard conditions, to give a compound of the general Formula XIV

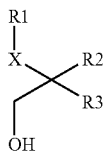 (XIV)

(d) Compounds of the general Formula XIV may thereafter be reacted with a compound of the general Formula IX

 (IX)

wherein $R_5$ is a suitable protecting group, such as Ac or Bz, in the presence of a suitable reagent, such as $PPh_3$/DIAD, under standard conditions to give compounds of the general Formula I, wherein $R_1$, $R_2$, $R_3$, and $R_4$ are as defined above and Y is $CH_2$ and X is O, S, $C(Z)_2$, or N(Z).

e) Compounds of the general Formula I, wherein $R_1$, $R_2$, $R_3$, $R_4$ and Y are as defined above and and X is S may thereafter be reacted with a suitable oxidizing reagent, such as MCPBA under standard conditions to give compounds of the general Formula I, wherein $R_1$, $R_2$, $R_3$, $R_4$ and Y are as defined above and and X is SO or $SO_2$.

Process C for manufacture of compounds with the general Formula I, wherein $R_1$, $R_2$, $R_3$, $R_4$, and Y, are as defined above and X is $NR_6CO$, $CONR_6$, $SO_2NR_6$ or $NR_6SO_2$ comprises the following steps:

a) Reacting a compound of the general Formula XV,

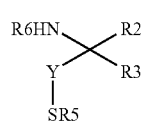 (XV)

wherein $R_2$, $R_3$, $R_6$ and Y are as defined for Formula I and $R_5$ is a suitable protecting group, such as Ac, Bz, PMB or Bn, with a compound of the general Formula XVI,

 (XVI)

wherein $R_1$ is as defined for Formula I and X is COOH or $SO_2Cl$ in the presence of suitable coupling reagents, such as PyBOP/DIPEA, DCC/HOBt, EDC/TEA/DMAP or pyridine under standard conditions to give compounds of the general Formula I, wherein $R_1$, $R_2$, $R_3$, $R_4$, and Y, are as defined above and X is $NR_6CO$ or $NR_6SO_2$.

b) Reacting a compound of the general Formula XVII,

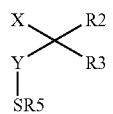 (XVII)

wherein $R_2$, $R_3$, and Y are as defined for Formula I and X is COOH or $SO_2Cl$ and $R_5$ is a suitable protecting group, such as Ac, Bz, PMB or Bn, with a compound of the general Formula XVIII,

 (XVIII)

wherein $R_6$ is as defined for Formula I in the presence of suitable coupling reagents, such as PyBOP/DIPEA, DCC/HOBt, EDC/TEA/DMAP or pyridine under standard conditions to give compounds of the general Formula I, wherein $R_1$, $R_2$, $R_3$, $R_4$ and Y are as defined above and X is $CONR_6$ or $SO_2NR_6$.

It will be appreciated by those skilled in the art that in the processes described above the functional groups of intermediate compounds may need to be protected by suitable protecting groups.

Functional groups, which it is desirable to protect, include hydroxy, amino, mercapto and carboxylic acid. Suitable protecting groups for hydroxy include trialkylsilyl or diarylalkylsilyl (e.g. t-butyldimethylsilyl, t-butyldiphenylsilyl or trimethylsilyl), tetrahydropyranyl and benzyl. Suitable protecting groups for amino, amidino and guanidino include t-butyloxycarbonyl and benzyloxy-carbonyl. Suitable protecting groups for mercapto include $CO-C_{1-6}$ alkyl, p-methoxybenzyl and trityl. Suitable protecting groups for carboxylic acid include $C_{1-6}$ alkyl and benzyl esters.

Protecting groups may be removed in accordance with techniques, which are well known to those skilled in the art and as described hereinafter.

Certain protected derivatives of compounds of Formula I, which may be made prior to a final deprotection stage to form compounds of Formula I, are novel.

The use of protecting groups is described in 'Protective Groups in Organic Synthesis', 2nd edition, T. W. Greene & P. G. M. Wutz, Wiley-Interscience (1991). The protective group may also be a polymer resin such as Wang resin or a 2-chorotrityl chloride resin.

It will also be appreciated by those skilled in the art, although such protected derivatives of compounds of Formula I may not possess pharmacological activity as such, they may be administered parenterally or orally and thereafter metabolised in the body to form compounds of the invention which are pharmacologically active. Such derivatives may therefore be described as "prodrugs". All prodrugs of compounds of Formula I are included within the scope of the invention.

It should also be understood that all polymorphs, amorphous forms, anhydrates, hydrates, solvates of the compounds of the present invention are within the scope of the invention.

Pharmaceutical Formulations

In yet a further aspect, the invention relates to pharmaceutical compositions containing at least one compound of the present invention, or a pharmaceutically acceptable salt thereof, as active ingredient.

For clinical use, the compounds of the invention are formulated into pharmaceutical formulations for oral, intravenous, subcutaneous, tracheal, bronchial, intranasal, pulmonary, transdermal, buccal, rectal, parenteral or other mode of administration. The pharmaceutical formulation contains a compound of the invention in combination with one or more pharmaceutically acceptable ingredients. The carrier may be in the form of a solid, semi-solid or liquid diluent, or a capsule. These pharmaceutical preparations are a further object of the invention. Usually the amount of active compounds is between 0.1–95% by weight of the preparation.

In the preparation of pharmaceutical formulations containing a compound of the present invention the compound selected may be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture may then be processed into granules or pressed into tablets.

Soft gelatine capsules may be prepared with capsules containing a mixture of the active compound or compounds of the invention, vegetable oil, fat, or other suitable vehicle for soft gelatine capsules. Hard gelatine capsules may contain granules of the active compound. Hard gelatine capsules may also contain the active compound in combination with solid powdered ingredients such as lactose, saccharose, sorbitol, mannitol, potato starch, cornstarch, amylopectin, cellulose derivatives or gelatine.

Dosage units for rectal administration may be prepared (i) in the form of suppositories which contain the active substance mixed with a neutral fat base; (ii) in the form of a gelatine rectal capsule which contains the active substance in a mixture with a vegetable oil, paraffin oil or other suitable vehicle for gelatine rectal capsules; (iii) in the form of a ready-made micro enema; or (iv) in the form of a dry micro enema formulation to be reconstituted in a suitable solvent just prior to administration.

Liquid preparations may be prepared in the form of syrups or suspensions, e.g. solutions or suspensions containing the active ingredient and the remainder consisting, for example, of sugar or sugar alcohols and a mixture of ethanol, water, glycerol, propylene glycol and polyethylene glycol. If desired, such liquid preparations may contain colouring agents, flavouring agents, preservatives, saccharine and carboxymethyl cellulose or other thickening agents. Liquid preparations may also be prepared in the form of a dry powder to be reconstituted with a suitable solvent prior to use.

Solutions for parenteral administration may be prepared as a solution of a compound of the invention in a pharmaceutically acceptable solvent. These solutions may also contain stabilizing ingredients, preservatives and/or buffering ingredients. Solutions for parenteral administration may also be prepared as a dry preparation to by reconstituted with a suitable solvent before use.

The typical daily dose of the active substance varies within a wide range and will depend on various factors such as for example the individual requirement of each patient, the route of administration and the disease. In general, oral and parenteral dosages will be in the range of 0.1 to 1000 mg per day of active substance.

Medical and Pharmaceutical Use

The compounds of the invention are inhibitors of carboxypeptidase U either as such or, in the case of prodrugs, after administration. The compounds of the invention are thus expected to be useful in those conditions where inhibition of carboxypeptidase U is beneficial, such as in the treatment or prophylaxis of thrombosis and hypercoagulability in blood and tissues of mammals, including man.

It is known that hypercoagulabililty may lead to thromboembolic diseases. Conditions associated with hypercoagulability and thrombo-embolic diseases which may be mentioned include protein C resistance and inherited or acquired deficiencies in antithrombin III, protein C, protein S and heparin cofactor II. Other conditions known to be associated with hypercoagulability and thrombo-embolic disease include circulatory and septic shock, circulating antiphospholipid antibodies, homocysteinemia, heparin-induced thrombocytopenia and defects in fibrinolysis. The compounds of the invention are thus indicated both in the therapeutic and/or prophylactic treatment of these conditions. The compounds of the invention are further indicated in the treatment of conditions where there is an undesirable excess of proCPU/CPU.

Particular disease states which may be mentioned include the therapeutic and /or prophylactic treatment of venous thrombosis and pulmonary embolism, arterial thrombosis (e.g. in myocardial infarction, unstable angina, thrombosis-based stroke and peripheral arterial thrombosis) and systemic embolism usually from the atrium during arterial fibrillation or from the left ventricle after transmural myocardial infarction.

Moreover, the compounds of the invention are expected to have utility in prophylaxis of re-occlusion and restenosis (i.e. thrombosis) after thrombolysis, percutaneous transluminal angioplasty (PTA) and coronary bypass operations; the prevention of re-thrombosis after microsurgery and vascular surgery in general.

Further indications include the therapeutic and/or prophylactic treatment of disseminated intravascular coagulation caused by bacteria, multiple trauma, intoxication or any other mechanism, fibrinolytic treatment when blood is in contact with foreign surfaces in the body, such as vascular grafts, vascular stents, vascular catheters, mechanical and biological prosthetic valves or any other medical device, and fibrinolytic treatment when blood is in contact with medical devices outside the body, such as during cardiovascular surgery using a heart-lung machine or in haemodialysis.

The compounds of the invention may also be combined and/or coadministered with any antithrombotic agent with a different mechanism of action, such as the antiplatelet agents acetylsalicylic acid ticlopidine, clopidogrel, thromboxane receptor and/or synthetase inhibitors, fibrinogen receptor antagonists, prostacyclin mimetics and phosphodiesterase inhibitors and ADP-receptor ($P_2T$) antagonists and thrombin inhibitors.

The compounds of the invention may further be combined and/or coadministered with thrombolytics such as tissue plasminogen activator (natural, recombinant or modified), streptokinase, urokinase, prourokinase, anisoylated plasminogen-streptokinase activator complex (APSAC), animal salivary gland plasminogen activators, and the like, in the treatment of thrombotic diseases, in particular myocardial infarction and stroke.

In Vitro Experiments

The inhibiting effect of the compounds of the present invention was estimated using the assay described in: Dirk Hendriks, Simon Scharpé and Marc van Sando, Clinical Chemistry, 31, 1936–1939 (1985); and Wei Wang, Dirk F. Hendriks, Simon S. Scharpé, The Journal of Biological Chemistry, 269, 15937–15944 (1994). The essential aspects of the assay system described in these references are set forth below.

Principle

Carboxypeptidase U (CPU) acts on the substrate hippuryl-arginine. Arginine is cleaved off from the substrate, resulting in the formation of hippuric acid. Hippuric acid is then detected by means of HPLC.

Materials

Chemicals

ProCPU was purified from human plasma according to Clinica Chimica Acta, 292, 25–40, (2000). Hippuryl-arginine and thrombin were from Sigma, thrombomodulin was from American Diagnostica, 2-Methylhippuric acid was from Aldrich. PPACK*HCl was from Alexis, ethyl acetate was from Fisher Scientific Int Company and all other reagents and solvents were from Merck.

HPLC System

The system employed for measurement of generated hippuric acid comprised a high precision pump model 480, auto sampler Gina 50, auto sampler rack 5805.9210, UV-detector UVD 1706 and degasser GT-102 (Gynkotek, Munchen, Germany) with Chromeleon sofware (version 6,00) and a Sperisorb C18, 5 ODS, (150 mm×4.6 mm) column using 85% $KH_2PO_4$ (10 mM, pH 3.5, adjust pH with 10% $H_3PO_4$) and 15% acetonitrile as the mobile phase.

Activation of proCPU

Thrombin

Thrombin (10 U) was dissolved in 5 mM $CaCl_2$ (1 mL). This solution was further diluted with dilution buffer to give a 12 nM thrombin solution.

Thrombomodulin

A 1 mL vial of 430 nM thrombomodulin (30 U thrombomodulin) was diluted with dilution buffer to give a 48 nM thrombomodulin solution.

PPACK

PPACK*HCl (5 mg) was dissolved in distilled $H_2O$ (1 mL). This solution was further diluted with buffer to give a 20 μM PPACK solution.

Dilution Buffer

The dilution buffer consisted of Hepes 20 mM, $CaCl_2$ 5 mM, Tween 80 0.01%, pH7.4.

Inactivated Plasma

Citrated human blood was centrifuged at 20000×g for 20 minutes at 4° C. The plasma was then incubated for 12 hours at 56° C.

ProCPU

ProCPU was diluted in 50 mM Hepes buffer (ph 7.4) to give a CPU activity of about 0.5–1.5 mU per sample in the assay.

Activation of proCPU

A solution of thrombomodulin (48 nM, 100 μL) and a solution of proCPU (100 μL) were added to a solution of thrombin (12 nM, 100 μL). The mixture was Incubated for 10 min at room temperature. A solution of PPACK (20 μM, 100 μL) was added and the mixture was incubated for 10 minutes at room temperature. Inactivated plasma (100 μL) was added and the resulting mixture was put on ice.

Assay for Carboxypeptidase U Activity

Substrate

Hippuryl-arginine (503 mg) was dissolved in 50 mM Hepes buffer (50 mL, pH 7.4) to give a 30 mM solution of hippuryl-arginine. The solution was sonicated prior to use.

Internal Standard

2-Methylhippuric acid (291 mg) was dissolved in 99.5% EtOH (25 mL) and distilled $H_2O$ was then added to give a total volume of 100 mL. The solution was diluted further with 4 volumes of 25% EtOH before addition to assay.

Carboxypeptidase U Activity Assay

Substrate (30 mM, 40 μL) was added to each vial. A solution of a carboxypeptidase U inhibitor of different concentrations (5 μL) or vehicle 5 μL) was then added to the vials. The assay was started by adding proCPU (5 μL) every 10 or 15 seconds to the vials, one at a time. The mixture was then incubated for 30 minutes at 37° C. The assay was stopped by adding HCl (1M, 50 μL) to one vial at a time every 10 or 15 seconds. Internal standard (10 μL) and ethyl acetate (300 μL) were then added to each vial. The sample mixtures were mixed by turning the vials upside down 30 times. The vials were then centrifuged for 1 minute at 1000×g. Two hundred (200) μL of the upper layer (the ethyl acetate phase) was transferred to HPLC-vials and the solution was evaporated to dryness using a stream of nitrogen. The samples were redissolved in mobile phase (75 μL) and analyzed in the HPLC system. For calculation of the effect of carboxypeptidase U inhibitor, the enzyme activity was determined in the presence of increasing concentrations of inhibitor.

EXAMPLES

General Experimental Procedures

Mass spectra were recorded on a Finnigan MAT TSQ 700 triple quadropole mass spectrometer equipped with an electrospray interface (FAB-MS) and VG Platform II mass spectrometer equipped with an electrospray interface (LC-MS). $^1H$ NMR and $^{13}C$ NMR measurements were performed on Varian UNITY plus 400, 500 and 600 spectrometers, operating at $^1H$ frequencies of 400, 500 and 600 MHz respectively. Chemical shifts are given in ppm with the solvent as internal standard. Organic extracts were dried using $MgSO_4$ or $Na_2SO_4$ as the drying agent. Chromatography separations were performed using Merck Silica gel 60 (0.063–0.200 mm). HPLC separations were performed on a HIGHCROM KR100-10C8 column.

Example 1

2-Mercaptomethyl-3-piperidin4-yl-propionic acid (a) 3-Piperidin-4-yl-propionic acid A solution of 3-pyridin4-yl-acrylic acid (4.20 g, 28.0 mmol) in water (50 mL) and ammonia (aq, 25%, 4 mL) was hydrogenated at 60 bar in a high pressure steel autoclave in presence of ruthenium (5% on alumina, 439 mg). When hydrogen pressure remained constant (3 days) the catalyst was removed from the reaction mixture by filtration. The catalyst was washed with ethanol and water, and the ethanol was removed from the solution on a rotavapor and the aqueous solution was freeze dried to give 3-piperidin4-yl-propionic acid (4.30 g, 100%).

(b) 4-(2-carboxy-ethyl)-piperidine-1-carboxylic acid tert-butyl ester

A solution of 3-piperidin4-yl-propionic acid (4.79 g, 30.5 mmol), di-tert-butyl-dicarbonate (6.98 g, 32.0 mmol) and $NaHCO_3$ (2.69 g, 32.0 mmol) in THF/water (1:1, 50 mL) were stirred at room temperature for 22 h. Another portion of di-tert-butyl-dicarbonate (2.00 g, 9.10 mmol) was added together with a catalytic amount of DMAP, the resulting mixture was stirred for another four days. THF was removed under reduced pressure and the aqueous phase was extracted with $CH_2Cl_2$. The aqueous was then acidified to pH 2 with 1M HCl and the acid extracted with $CH_2Cl_2$. The combined organic extracts were washed with brine, dried and concentrated in vacuo to yield 4-(2-carboxy-ethyl)-piperidine-1-carboxylic acid tert-butyl ester as a white solid (6.36 g, 81%).

(c) 4-(3-Benzylsulfanyl-2-carboxy-propyl)-piperidine-1-carboxylic acid tert-butyl ester BuLi (1.6 M, 15.3 mL, 24.4 mmol) was added to a solution of diisopropylamine (3.43 mL, 24.4 mmol) in THF (3 mL) at −78° C. under argon. After a few min the solution was allowed to warm up to room temperature over a period of 15 min. The resulting LDA solution was slowly added to a solution of 4-(2-carboxy-ethyl)-piperidine-1-carboxylic acid tert-butyl ester (3.07 g, 11.9 mmol) in THF (7 mL) at −78° C. The resulting solution was stirred at −78° C. for 10 min., THF (20 mL) was added during that time in order to dissolve the anion which had solidified. The dianion was cooled to −78° C. and bromomethyl thiobenzylether (2.72 g, 12.5 mmol) was added as a solution in THF (3 mL), the solution was stirred at −78° C. for 30 min, at 0° C. for 30 min and then allowed to warm up to room temperature and stirred overnight. The reaction mixture was acidified with 1 M HCl, diluted with EtOAc and the organic phase was washed with water and dried. The crude product was purified by flash chromatography (MeOH/$CHCl_3$,1:9) to yield 4-(3-Benzylsulfanyl-2-carboxy-propyl)-piperidine-1-carboxylic acid tert-butyl ester as a pale yellow oil (3.12 g, 66%).

(d) 4-(2-Carboxy-3-mercapto-propyl)-piperidine-1-carboxylic acid tert-butyl ester Sodium metal (513 mg, 22.5 mmol) was added in portions during 5 min. to a solution of 4-(3-Benzylsulfanyl-2-carboxy-propyl)-piperidine-1-carboxylic acid tert-butyl ester (0.9 g, 2.29 mmol) in THF (45 mL) and liquid ammonia (50 mL) at −60° C. under argon. After stirring for 15 min. ammonium chloride (1.7 g, 31.5 mmol) was added in portions. The cooling bath was removed and the ammonia was evaporated using a stream of argon. 0.5 M NaOH was added and the mixture was washed with heptane. The aqueous phase was acidified with 2 M HCl and extracted with methylene chloride. The organic phase was washed with brine, dried and concentrated under reduced pressure to give 4-(2-Carboxy-3-mercapto-propyl)-piperidine-1-carboxylic acid tert-butyl ester (0.7 g, 100%).

(e) 2-Mercaptomethyl-3-piperidin4-yl-propionic acid

To a solution of 4-(2-Carboxy-3-mercapto-propyl)-piperidine-1-carboxylic acid tert-butyl ester (0.7 g, 2.29 mmol) in methylene chloride (8 mL) under argon was added triethylsilane (731 μL, 4.58 mmol) followed by TFA (4 mL). The reaction mixture was stirred for 60 min. and then concentrated under reduced pressure. Purification by HPLC (10→30% acetonitrile, 0.1% TFA in water) gave the title compound as the TFA salt (447 mg, 61%).

$^1$H NMR (400 MHz, $D_2O$): δ 1.34–1.50 (m, 2H), 1.54–1.76 (m, 3H), 1.90–1.99 (m, 1H), 2.0–2.1 (m, 1H), 2.9–3.05 (m, 5H), 3.38–3.48 (m, 2H). MS (+) 204 (M+1).

Example 2

3-(1-Acetyl-piperidin4-yl)-2-mercaptomethyl-propionic acid

A solution of 2-Mercaptomethyl-3-piperidin-4-yl-propionic acid TFA salt (0.1 g, 0.32 mmol) in acetic anhydride (2 mL) was stirred over night under argon and then concentrated under reduced pressure. Purification by HPLC (10→50% acetonitrile, 0.1% TFA in water) gave the title compound (63 mg, 80%).

$^1$H NMR (500 MHz, $CD_3OD$): δ 1.0–1.22 (m, 2H), 1.46–1.55 (m, 1H), 1.55–1.66 (m, 2H), 1.67–1.79 (m, 1H), 1.81–1.92 (m, 1H), 2.08 (s, 3H), 2.55–2.73 (m, 4H), 3.03–3.12 (m, 1H), 3.85–3.94 (m, 1H), 4.454.53 (m, 1H). MS (+) 246 (M+1).

Example 3

3-Mercapto-5-methyl-2-piperidin-4-ylmethyl-hexanoic acid (a) 4-Hydroxymethyl-piperidine-1-carboxylic acid tert-butyl ester To a solution of, 4-(hydroxymethyl)piperidine (5.00 g, 43.41 mmol THF/$H_2O$ (1:1, 120 mL) was added di-t-butyl dicarbonate (9.47 g, 43.41 mmol). The reaction mixture was stirred for 16 h at room temperature. The reaction mixture was then poured into $H_2O$ (500 mL) and extracted with ethyl acetate (3×250 mL). The organic layers were combined and washed with water. The organic layer was dried over sodium sulfate, filtered, and then concentrated under reduced pressure to give 4-hydroxymethyl-piperidine-1-carboxylic acid tert-butyl ester (9.01 g, 96%).

(b) 4-Bromomethyl-piperidine-1-carboxylic acid tert-butyl ester

To a solution 4-hydroxymethyl-piperidine-1-carboxylic acid tert-butyl ester (8.75 g, 40.64 mmol) in diethyl ether (200 mL) at 0° C. under nitrogen. were added triphenyl phosphine (21.32 g, 81.28 mmol) and carbon tetrabromide (26.96 g, 81.28 mmol). The mixture was allowed to warm to room temperature and stirred under nitrogen for 48 h. The reaction mixture was filtered through a pad of Celite and the organic filtrate was washed with 5% $NaS_2O_3$, water, brine, and dried. The mixture was filtered and concentrated under reduced pressure. The crude product was purified by column chromatography (ethyl acetate/hexane, 1:9) to give 4-bromomethyl-piperidine-1-carboxylic acid tert-butyl ester (8.26 g, 73%).

(c) 4-[2-tert-Butoxycarbonyl-2-(diethoxyphosphoryl)-ethyl]-piperidine-1-carboxylic acid tert-butyl ester tert-Butyl diethylphosphonoacetate (75.0 g, 297.32 mmol) was added dropwise to a suspension of sodium hydride (8.03 g, 334.58 mmol) in DMF (450 mL) at 0° C. under nitrogen. The mixture was stirred at 0° C. for 0.5 h and at room temperature for 0.5 h. 4-bromomethyl-piperidine-1-carboxylic acid tert-butyl ester (20.68 g, 74.34 mmol) in DMF (50 mL) was added dropwise to the reaction mixture and the reaction was heated to 60° C. and stirred for 16 h. The reaction was cooled to room temperature, poured into $H_2O$ and extracted with ethyl acetate. The organic layers were combined and washed with water. The organic layer was dried, filtered, and concentrated under reduced pressure. The crude product was purified by column chromatography (ethyl acetate/hexane, 3:7) to give 4-[2-tert-Butoxycarbonyl-2-(diethoxy-phosphoryl)-ethyl]-piperidine-1-carboxylic acid tert-butyl ester and unreacted t-butyl diethylphosphonoacetate. The product was 47% pure by HPLC. The product was further purified by vacuum distillation to give 77% purity. This mixture was taken on to the next reaction.

(d) 4-(2-tert-Butoxycarbonyl-5-methyl-hex-2-enyl)-piperidine-1-carboxylic acid tert-butyl ester 4-[2-tert-Butoxycarbonyl-2-(diethoxy-phosphoryl)-ethyl]-piperidine-1-carboxylic acid tert-butyl ester(8.1 g) in 20 mL DME was added dropwise to a suspension of sodium hydride (1.04 g, 43.13 mmol) in DME (20 mL) at 0° C. under nitrogen. The mixture was stirred for 0.75 h and isovaleraldehyde (7.76 g, 90.1 mmol) was added dropwise to the mixture. The mixture was allowed to warm to room temperature and. stirred for 48 h. The mixture was diluted with ether and washed with water. The organic layer was dried, filtered, and concentrated under reduced pressure to give 9.4 g of a yellow oil. The crude product was purified by column chromatography (ethyl acetate/hexane, 1:50) to give 4-(2-tert-butoxycarbonyl-5-methyl-hex-2-enyl)-piperidine-1-carboxylic acid tert-butyl ester (1.53 g, 24%) for two reactions.

(e) 4-[2-tert-Butoxycarbonyl-3-(4-methoxy-benzylsulfanyl)-5-methyl-hexyl]-piperidine-1-carboxylic acid tert-butyl ester A solution of 4-(2-tert-butoxycarbonyl-5-methyl-hex-2-enyl)-piperidine-1-carboxylic acid tert-butyl ester (2.0 g, 5.24 mmol) in DMF (5 mL) was added to a mixture of potassium carbonate (0.54 g, 3.93 mmol) and 4-methoxy-α-toluenethiol (1.17 g, 10.48 mmol) in DMF (50 mL) under nitrogen. The mixture was refluxed for 5 h and allowed to cool to room temperature. The reaction mixture was then poured into $H_2O$ and extracted with ethyl acetate. The organic layers were combined and washed with water. The organic layer was dried, filtered and concentrated under reduced pressure to give 3.76 g of crude material. The crude product was purified by column chromatography (ethyl acetate/hexane, 1:10) to give 4-[2-tert-butoxycarbonyl-3-(4-methoxy-benzylsulfanyl)-5-methyl-hexyl]-piperidine-1-carboxylic acid tert-butyl ester (1.77 g, 63%).

(f) 3-Mercapto-5-methyl-2-piperidin-4-ylmethyl-hexanoic acid

A mixture of $H_2O$ (2.6 mL) and TFA (26 mL) was frozen and then allowed to warm to room temperature under nitrogen. 4-[2-tert-butoxycarbonyl-3-(4-methoxy-benzylsulfanyl)-5-methyl-hexyl]-piperidine-1-carboxylic acid tert-butyl ester (2.62 g, 4.89 mmol) was added and the mixture was refluxed for 16 h. The mixture was allowed to cool to room temperature and concentrated under reduced pressure. The crude product was purified by reverse-phase column chromatography (MeOH/$H_2O$, 3:2) to give the title compound as the TFA salt (0.40 g, 22%).

$^1$H NMR (300 MHz) (CD$_3$OD) δ 0.88 (d,), 0.94 (d,), 1.43 (m), 1.70 (br), 1.94 (m), 2.48 (m), 2.90 (m), 2.99 (br), 3.34 (m). MS (+) 260.2 (M-TFA).

Example 4

3-Mercapto-4-phenyl-2-piperidin-4-ylmethyl-butyric acid (a) 4-(2-tert-Butoxycarbonyl4-phenyl-but-2-enyl)-piperidine-1-carboxylic acid tert-butyl ester A solution of 4-[2-tert-butoxycarbonyl-2-(diethoxy-phosphoryl)-ethyl]-piperidine-1-carboxylic acid tert-butyl ester (3.0 g) in DME (8 mL) was added dropwise to a suspension of sodium hydride (0.26 g, 10.51 mmol) in DME (8 mL) at 0° C. under nitrogen. The mixture was stirred for 0.75 h. Phenyl acetaldehyde (5.26 g, 43.81 mmol) was added dropwise to the mixture at 0° C. The mixture was allowed to warm to room temperature and stirred for 16 h. The mixture was diluted with ether and washed with water. The organic layer was dried, filtered, and concentrated under reduced pressure to give 8.6 g of a yellow oil. The crude product was purified by column chromatography (ethyl acetate/hexane, 1:50→1:10) to give 4-(2-tert-butoxycarbonyl4-phenyl-but-2-enyl)-piperidine-1-carboxylic acid tert-butyl ester (1.32 g, 62% yield) for two reactions.

(b) 4-[2-tert-Butoxycarbonyl-3-(4-methoxy-benzylsulfanyl)-4-phenyl-butyl]-piperidine-1-carboxylic acid tert-butyl ester 4-(2-tert-Butoxycarbonyl4-phenyl-but-2-enyl)-piperidine-1-carboxylic acid tert-butyl ester (0.8 g, 1.93 mmol) in DMF (10 mL) was added to a suspension of potassium carbonate (0.20 g, 1.44 mmol) ) and 4-methoxy-α-toluenethiol (0.54 mL, 3.85 mmol) in DMF (10 mL) under nitrogen. The mixture was heated to 75° C. for 24 h and allowed to cool to room temperature. The reaction mixture was then poured into $H_2O$ and extracted with ethyl acetate. The organic layers were combined and washed with water. The organic layer was dried, filtered, and concentrated under reduced pressure to give 1.8 g crude material. The crude product was purified by column chromatography (ethyl acetate/hexane, 1:10) to give 4-[2-tert-butoxycarbonyl-3-(4-methoxy-benzylsulfanyl)4-phenyl-butyl]-piperidine-1-carboxylic acid tert-butyl ester (0.55 g, 50%).

(c) 3-Mercapto-4-phenyl-2-piperidin-4-ylmethyl-butyric acid

A mixture of $H_2O$ (0.65 mL) and TFA (6.5 mL) was frozen and then allowed to warm to room temperature under nitrogen. 4-[2-tert-butoxycarbonyl-3-(4-methoxy-benzylsulfanyl)-4-phenyl-butyl]-piperidine-1-carboxylic acid tert-butyl ester (0.65 g, 1.14 mmol) was added and the mixture was refluxed for 16 h. The mixture was allowed to cool to room temperature and concentrated under reduced pressure. The crude product was purified by reverse-phase column chromatography (MeOH/$H_2O$, 1:1) to give the title compound as the TFA salt (0.27 g, 58%).

$^1$H NMR (300 MHz) (DMSO) δ 1.22 (m), 1.49 (m), 1.67 (br), 2.21 (d,), 2.98 (m), 7.25 (m, 5H), 8.27 (br), 8.57 (br), 12.59 (br). MS (+) 294.3 (M-TFA).

Example 5

2-(2-Amino-pyridin-4-ylmethyl)-3-mercapto-propionic acid (a) N-(4-Methyl-pyridin-2-yl)-acetamide 2-Amino4-methylpyridine (99.0 g, 91.5 mmol) in acetic anhydride (250 mL) was warmed to 70° C. for two h. The mixture was cooled to room temperature and diethyl ether (100 mL) added. The product crystallized as white needle crystals. Filtering and drying in vacuo afforded N-(4-methyl-pyridin-2-yl)-acetamide (130 g, 95%).

(b) 2-Acetylamino-isonicotinic acid

A mixture of N-(4-methyl-pyridin-2-yl)-acetamide (40.0 g, 0.26 mol) and water (400 mL) was heated at 90° C. until the solution was homogeneous. $KMnO_4$ (100 g, 0.62 mol) was added carefully in small portions with vigorous mechanical stirring over 2 h. The reaction mixture was kept at 90–95° C. for further 3 h before filtering through Celite while still hot. The filtrate was concentrated to about 100 mL and concentrated HCl was added to adjust the pH to about 4. The reaction flask was cooled in an ice bath and the white solid filtered off. The crystals were washed with cold water and chloroform and dried in vacuo giving 2-acetylamino-isonicotinic acid (12.0 g, 25%).

(c) 2-Amino-isonicotinic acid ethyl ester

2-Acetylamino-isonicotinic acid (10.8 g, 60.0 mmol) was suspended in ethanol (150 mL) and $BF_3OEt_2$ (22 mL, 138 mmol) was added. The mixture was refluxed overnight, and after cooling to room temperature 10% $NaHCO_3$ (250 mL) was added. The product was extracted with chloroform and the combined organic extracts were washed with water and dried. Filtering and concentration afforded 2-amino-isonicotinic acid ethyl ester (7.46 g, 79%) as pale yellow crystals.

(d) 2-[N,N-bis(tert-Butoxycarbonyl)amino]-isonicotinic acid ethyl ester

To a solution of 2-amino-isonicotinic acid ethyl ester (5.00 g, 30 mmol) in t-BuOH (45 mL) and acetone (15 mL) was added DMAP (50 mg, 0.41 mmol) and di-t-butyl dicarbonate (16.4 g, 75.0 mmol). The reaction was stirred at room temperature overnight and hexane (60 mL) was added. The reaction mixture was cooled in a refrigerator for 3 h and filtered to give 2-[N,N-bis(tert-butoxycarbonyl)amino]-isonicotinic acid ethyl ester (8.71 g, 79%).

(e) (4-Hydroxymethyl-pyridin-2-yl)-carbamic acid tert-butyl ester

A solution of to 2-[N,N-bis(tert-Butoxycarbonyl)amino]-isonicotinic acid ethyl ester (35.0 g, 95.5 mmol) in THF (350 mL) was treated with $LiAlH_4$ (7.25 g, 191 mmol) and refluxed for 1 h under nitrogen. The reaction mixture was poured carefully onto crushed ice and the product extracted several times with $CHCl_3$ and $CHCl_3$: MeOH (9:1). The combined organic extracts were dried, filtered and concentrated under reduced pressure to give (4-hydroxymethyl-pyridin-2-yl)-carbamic acid tert-butyl ester (18.5 g, 86%) as a pale yellow solid.

(f) (4-Bromomethyl-pyridin-2-yl)-carbamic acid tert-butyl ester (4-Hydroxymethyl-pyridin-2-yl)-carbamic acid tert-butyl ester (8.00 g, 35.6 mmol) was dissolved in $CH_2Cl_2$ (150 mL) and treated with $PPh_3$ (11.2 g, 42.8 mmol) under nitrogen. The reaction flask was cooled in an ice bath and $CBr_4$ (14.2 g, 42.8 mmol) was added in small portions. The ice bath was removed after 30 min and the reaction mixture was stirred overnight at room temperature. The reaction mixture was concentrated under reduced pressure and acetonitrile (50 mL) was added. The reaction flask was placed in a refrigerator for 3 h and the precipitate filtered and washed with cold acetonitrile. The white solid was dried in vacuo giving (4-bromomethyl-pyridin-2-yl)-carbamic acid tert-butyl ester (8.38 g, 82%).

(g) 2-(2-tert-Butoxycarbonylamino-pyridin-4-ylmethyl)-malonic acid diethyl ester To a solution of NaH (80%, 0.17 g, 4.00 mmol) in THF (5 mL) at 0° C. under argon was added diethyl malonate (0.64 g, 4.00 mmol). After the mixture was stirred for 15 min the mixture was added to a refluxed mixture of (4-bromomethyl-pyridin-2-yl)-carbamic acid tert-butyl ester (1.00 g, 3.48 mmol) in THF (10 mL), and the mixture was refluxed for 2 h. The mixture was concentrated under reduced pressure and the residue was partitioned between water and chloroform. The organic layer was washed with water and brine and dried. After filtration and evaporation of the solvent, the crude product was purified by flash chromatography (MeOH/$CH_2Cl_2$, 1:100) to give 2-(2-tert-butoxycarbonylamino-pyridin4-ylmethyl)-malonic acid diethyl ester (0.80 g, 55%).

(h) 2-(2-tert-Butoxycarbonylamino-pyridin-4-ylmethyl)-malonic acid monoethyl ester A solution of KOH (0.19 g, 3.43 mmol) in ethanol (5 mL) was added to a solution of 2-(2-tert-butoxycarbonylamino-pyridin4-ylmethyl)-malonic acid diethyl ester (1.20 g, 3.27 mmol) in ethanol (5 mL) and methylene chloride (5 mL) at 0° C. The mixture was stirred for 18 h at room temperature. The mixture was concentrated under reduced pressure and water was added to the residue. The aqueous layer was washed with diethyl ether, acidified to pH 4 by 1M HCl, and extracted with methylene chloride. The organic layer was washed with water, brine and dried. After filtration and evaporation in vacuo, the crude product was purified by flash chromatography ($CH_3OH$/$CH_2Cl_2$, 1:20) to yield 2-(2-tert-butoxycarbonylamino-pyridin4-ylmethyl)-malonic acid monoethyl ester (0.90 g, 81%).

(i) 2-(2-tert-Butoxycarbonylamino-pyridin4-ylmethyl)-acrylic acid ethyl ester

A solution of diethylamine (0.26 g, 2.67 mmol) in methylene chloride (4 mL) was added to a mixture of 2-(2-tert-butoxycarbonylamino-pyridin4-ylmethyl)-malonic acid monoethyl ester (0.90 g, 2.66 mmol) and 37% aq. solution of formaldehyde (0.24 g, 3.00 mmol) at 0° C. The mixture was stirred for 5 h at room temperature and the mixture was poured onto ice-water and extracted with methylene chloride. The organic layer was washed with 5% $NaHCO_3$ and dried. The crude product was purified by flash chromatography (1% methanol in $CH_2Cl_2$) to yield 2-(2-tert-butoxycarbonylamino-pyridin4-ylmethyl)-acrylic acid ethyl ester (0.58 g, 71%).

(j) 2-Acetylsulfanylmethyl-3-(2-tert-butoxycarbonylamino-pyridin-4-yl)-propionic acid ethyl ester A solution of 2-(2-tert-butoxycarbonylamino-pyridin-4-ylmethyl)-acrylic acid ethyl ester (0.48 g, 1.57 mmol) and triethylamine (0.17 g, 1.64 mmol) was added to thioacetic acid (3 mL) at 0° C. under nitrogen. The mixture was stirred at room temperature for 4 h. The mixture was poured onto ice-water and extracted with $CH_2Cl_2$. The organic phase was washed with saturated $NaHCO_3$ (aq) and dried. The crude product was purified by flash chromatography (2.5% MeOH in CH$_2$Cl$_2$) to give 2-acetylsulfanylmethyl-3-(2-tert-butoxycarbonylamino-pyridin-4-yl)-propionic acid ethyl ester (0.60 g, 100%).

(k) 2-Acetylsulfanylmethyl-3-(2-amino-pyridin-4-yl)-propionic acid ethyl ester

TFA (0.5 mL) was added to a solution of 2-acetylsulfanylmethyl-3-(2-tert-butoxycarbonylamino-pyridin4-yl)-propionic acid ethyl ester (50 mg, 0.13 mmol) in methylene chloride under argon. The solution was stirred for 60 min and concentrated under reduced pressure to give crude 2-acetylsulfanylmethyl-3-(2-amino-pyridin-4-yl)-propionic acid ethyl ester (52 mg, 100%).

$^1$H NMR (500 MHz, CD$_3$OD$_3$): δ 1.15 (t, 3H), 2.32 (s, 3H), 2.73–2.83 (m, 2H), 2.86–2.93 (m, 1H), 3.01–3.07 (dd, 1H), 3.12–3.18 (dd, 1H), 4.034.12 (m, 2H), 6.39 (s, 1H), 6.43 (d, 1H), 7.77 (d, 1H).

(l) 2-(2-Amino-pyridin4-ylmethyl)-3-mercapto-propionic acid

2-Acetylsulfanylmethyl-3-(2-amino-pyridin4-yl)-propionic acid ethyl ester (52 mg, 0.13 mmol) was dissolved in conc. HCl (2 mL) under argon. The solution was heated to reflux for 1 h. Concentration under reduced pressure gave the title compound as the hydrochloride salt (32 mg, 100%).

$^1$H NMR (500 MHz. CD$_3$OD): δ 2.70 (bs, 2H), 2.85–3.0 (m, 3H), 6.76 (bs, 1H), 6.81 (bs, 1H), 7.67 (bs, 1H). MS (+) 213 (M+1).

Example 6

3-(6-Amino-pyridin-3-yl)-2-mercaptomethyl-propionic acid (a) 6-Amino-nicotinic acid ethyl ester 2-Amino-5-pyridinecarboxylic acid (25.0 g, 181 mmol) was suspended in ethanol (190 mL) and SOCl$_2$ (15 mL, 206 mmol) was added. The mixture was refluxed for 10 hs and more SOCl$_2$ (16 mL) was added. After 3 days with reflux (and more SOCl$_2$ (10 mL) added each day), the reaction mixture was cooled to room temperature and diethyl ether was added. After 24 h at –20° C. the mixture was filtered. The crude salt was dissolved in methanol (214 mL) and a solution of NaOH (40.0 g, 23.5 mmol) in methanol (90 mL) was added. The reaction mixture was stirred for 1 h and THF (270 mL) was added. The reaction mixture was filtered through a plug of silica (THF/MeOH) and concentrated under reduced pressure to give 6-amino-nicotinic acid ethyl ester (36.2 g, 97%).

(b) 6-tert-Butoxycarbonylamino-nicotinic acid ethyl ester

To a solution of 6-amino-nicotinic acid ethyl ester (36.0 g 217.0 mmol) in t-BuOH (308 mL) and acetone (103 mL) was added DMAP (0.53 g, 4.34 mmol) and di-t-butyl dicarbonate (72.0 g, 330 mmol). The reaction was stirred at room temperature for 10 h followed by addition of more di-t-butyl dicarbonate (2.60 g). After 10 h stirring at room temperature hexane (470 mL) was added. The reaction mixture was cooled to –20° C. for 2 h and filtered. The filtrate was washed with hexane/dichloromethane (3:1) and and dried in vacuo to give 6-tert-butoxycarbonylamino-nicotinic acid ethyl ester (40.5 g, 70%).

(c) (5-Hydroxymethyl-pyridin-2-yl)-carbamic acid tert-butyl ester

To a stirred solution of 6-tert-butoxycarbonylamino-nicotinic acid ethyl ester (3.50 g, 13.1 mmol) in THF (20 mL) under nitrogen was added LiAlH$_4$ (0.91 g, 24.0 mmol) in THF (20 mL) over a period of 2 h. The reaction mixture was stirred for 6 h, then NH$_4$Cl (sat.) was added (carefully) until neutral solution. The mixture was filtered and concentrated under reduced pressure to give (5-hydroxymethyl-pyridin-2-yl)-carbamic acid tert-butyl ester (2.00 g 68%).

(d) (5-Bromomethyl-pyridin-2-yl)-carbamic acid tert-butyl ester

Triphenylphosphine (8.70 g, 33.1 mmol) and carbontetrabromide (17.0 g, 51.2 mmol) were added to a suspension of (5-hydroxymethyl-pyridin-2-yl)-carbamic acid tert-butyl ester (7.00 g 31.2 mmol) in CH$_2$Cl$_2$ (200 mL) at room temperature. Stirring was continued for 5 h followed by evaporation of the solvent. Acetonitrile (200 mL) was added and the mixture was cooled to –20° C. for 2 h. The mixture was then filtered and the crystalline residue washed with cold acetonitrile (2×10 mL), to give (5-bromomethyl-pyridin-2-yl)-carbamic acid tert-butyl ester (5.96 g, 67%).

(e) 2-(6-tert-Butoxycarbonylamino-pyridin-3-ylmethyl)-malonic acid diethyl ester To a suspension of NaH (0.49 g, 16.3 mmol, 80%) in THF (15 mL) at 0° C. was added diethyl malonate (2.61 g, 16.3 mmol). The mixture was stirred for 15 min and was then added dropwise to a refluxed mixture of (5-bromomethyl-pyridin-2-yl)-carbamic acid tert-butyl ester (3.90 g, 13.6 mmol) in THF (25 mL), and the resulting solution was refluxed for 15 min. After evaporation of the solvent, the crude product was purified by flash chromatography (methanol/CH$_2$Cl$_2$, 1:100→2.5:100) to give 2-(6-tert-butoxycarbonylamino-pyridin-3-ylmethyl)-malonic acid diethyl ester (2.18 g, 44%).

(f) 2-(6-tert-Butoxycarbonylamino-pyridin-3-ylmethyl)-malonic acid monoethyl ester A solution of KOH (0.37 g, 6.54 mmol) in ethanol (5 mL) was added to a solution of 2-(6-tert-butoxycarbonylamino-pyridin-3-ylmethyl)-malonic acid diethyl ester (2.18 g, 5.95 mmol) in ethanol (25 mL) and methylene chloride (10 mL) at 0° C. The mixture was stirred for 18 h at room temperature. The mixture was concentrated under reduced pressure and the residue dissolved in water. The aqueous layer was washed with ether, acidified to pH 4 by 1M HCl and extracted with methylene chloride. The organic layer was washed with water, brine and dried. After filtration and concentration under reduced pressure, the crude product was purified by flash chromatography (methanol/CH$_2$Cl$_2$, 1:20) to yield 2-(6-tert-butoxycarbonylamino-pyridin-3-ylmethyl)-malonic acid monoethyl ester (1.00 g, 50%).

(g) 2-(6-tert-Butoxycarbonylamino-pyridin-3-ylmethyl)-acrylic acid ethyl ester

Diethylamine (0.29 g, 3.00 mmol), water (2 mL) and methylene chloride (2 mL) was added to a mixture of 2-(6-tert-butoxycarbonylamino-pyridin-3-ylmethyl)-malonic acid monoethyl ester (1.00 g, 2.96 mmol) and 37% aq. solution of formaldehyde (0.25 g, 3.05 mmol) at 0° C. The mixture was stirred for 16 h at room temperature and then poured onto ice-water and extracted with methylene chloride. The organic layer was washed with 5% NaHCO$_3$ and dried. Filtration and concentration under reduced pressure gave 2-(6-tert-butoxycarbonylamino-pyridin-3-ylmethyl)-acrylic acid ethyl ester (0.75 g, 83%).

(h) 2-Acetylsulfanylmethyl-3-(6-tert-butoxycarbonylamino-pyridin-3-yl)-propionic acid ethyl ester 2-(6-tert-butoxycarbonylamino-pyridin-3-ylmethyl)-acrylic acid ethyl ester (0.49 g, 1.60 mmol) and triethylamine (0.17 g, 1.64 mmol) were added to thioacetic acid (3 mL) at 0° C. The mixture was stirred at room temperature for 6 h. The mixture was poured onto ice-water and extracted with CH$_2$Cl$_2$. The organic phase was washed with saturated NaHCO$_3$ and dried. The crude product was purified by flash chromatography (MeOH/CH$_2$Cl$_2$, 2.5:100) to give 2-acetylsulfanylmethyl-3-(6-tert-butoxycarbonylamino-pyridin-3-yl)-propionic acid ethyl ester (0.36 g, 61%).

(i) 2-Acetylsulfanylmethyl-3-(6-amino-pyridin-3-yl)-propionic acid ethyl ester

TFA (0.5 mL) was added to a solution of 2-acetylsulfanylmethyl-3-(6-tert-butoxycarbonylaminopyridin-3-yl)-propionic acid ethyl ester (100 mg, 0.26 mmol) in methylene chloride (2 mL) under argon. The solution was stirred for 60 min and concentrated under reduced pressure to give crude 2-acetylsulfanylmethyl-3-(6-amino-pyridin-3-yl)-propionic acid ethyl ester (104 mg, 100%).

$^1$H NMR. (500 MHz, CD$_3$OD): δ 1.21 (t, 3H), 2.33 (s, 3H), 2.78–2.97 (m, 3H), 3.05–3.13 (m, 1H), 3.14–3.21 (m, 1H), 4.08–4.15 (m, 2H), 6.99 (d, 1H), 7.69 (s, 1H), 7.85 (d, 1H).

(j) 3-(6-Amino-pyridin-3-yl)-2-mercaptomethyl-propionic acid

2-Acetylsulfanylmethyl-3-(6-tert-butoxycarbonylamino-pyridin-3-yl)-propionic acid ethyl ester (38 mg, 0.096 mmol) was dissolved in conc. HCl (2.0 mL) under argon. The solution was stirred at room temperature for 1 h and then heated to reflux for 1 h. Concentration under reduced pressure gave the title compound (25.7 mg, 100%) as the hydrochloride salt.

$^1$H NMR (500 MHz, CD$_3$OD): δ 2.74–2.78 (m, 2H), 2.84–2.94 (m, 3H), 7.02 (d, 1H), 7.72 (s, 1H), 7.89 (d, 1H). MS (+) 213 (M+1).

Example 7

3-(6-Amino-pyridin-3-yl)-2-mercaptomethyl-2-methyl-propionic acid (a) 2-(6-tert-Butoxycarbonylamino-pyridin-3-ylmethyl)-2-methyl-malonic acid tert-butyl ester ethyl ester A solution of tert-butyl ethyl methylmalonate (457 mg, 2.26 mmol) in DMF (4 mL) was added dropwise to a suspension of NaH (90 mg, 2.26 mmol, 60% in oil) in DMF (4 mL). The reaction mixture was stirred for 20 min. A solution of (5-bromomethyl-pyridin-2-yl)-carbamic acid tert-butyl ester (500 mg, 1.74 mmol) in DMF (2.5 mL) was added and the reaction was stirred for 70 min. EtOAc was added and the mixture was washed with water and brine, dried and concentrated under reduced pressure. Chromathography (Heptane/EtOAc, 3:1→1:3) gave 2-(6-tert-butoxycarbonylamino-pyridin-3-ylmethyl)-2-methyl-malonic acid tert-butyl ester ethyl ester (437 mg, 61% yield).

(b) 2-(6-tert-Butoxycarbonylamino-pyridin-3-ylmethyl)-2-methyl-malonic acid mono-tert-butyl ester 1M NaOH (2 mL) was added to a solution of 2-(6-tert-butoxycarbonylamino-pyridin-3-ylmethyl)-2-methyl-malonic acid tert-butyl ester ethyl ester (0.42g, 1.03 mmol) in THF/EtOH (4 mL, 1:1). The reaction mixture was stirred at 50° C. for 16 h. CH$_2$Cl$_2$ was added and the mixture was washed with 0.5 M HCl and brine and dried. Concentration under reduced pressure gave 2-(6-tert-butoxycarbonylamino-pyridin-3-ylmethyl)-2-methyl-malonic acid mono-tert-butyl ester (348 mg, 89%).

(c) 3-(6-tert-Butoxycarbonylamino-pyridin-3-yl)-2-hydroxymethyl-2-methyl-propionic acid tert-butyl ester Methyl chloroformate (75 μL, 0.92 mmol) was added dropwise to a solution of 2-(6-tert-butoxycarbonylamino-pyridin-3-ylmethyl)-2-methyl-malonic acid mono-tert-butyl ester (348 mg, 0.915 mmol) and Et$_3$N (123 μL, 0.92 mmol) in THF (6 mL). The reaction mixture was stirred for 20 min., filtered and added dropwise to a suspension of NaBH$_4$ (39 mg, 1.04 mmol) in THF (6 mL) at 0° C. The reaction was stirred for 16 h at room temperature. 0.2 M HCl was added followed by EtOAc. The organic phase was washed with brine and dried. Concentration under reduced pressure followed by chromathography (toluene/EtOAc, 3:1→1:3) gave 3-(6tert-butoxycarbonylamino-pyridin-3-yl)-2-hydroxymethyl-2-methyl-propionic acid tert-butyl ester (190 mg, 57%).

(d) 2-Acetylsulfanylmethyl-3-(6-tert-butoxycarbonylamino-pyridin-3-yl)-2-methyl-propionic acid tert-butyl ester Diethyl azodicarboxylate (160 μL, 1.01 mmol) was added dropwise to a solution of 3-(6-tert-butoxycarbonylamino-pyridin-3-yl)-2-hydroxymethyl-2-methyl-propionic acid tert-butyl ester (180 mg, 0.49 mmol) and triphenylphosphine (266 mg, 1.01 mmol) in THF (6 mL) and the reaction was stirred for 5 min. Thiolacetic acid (96 μL, 1.34 mmol) was added and the reaction was stirred for 16 h. Concentration under reduced pressure followed by chromathography (toluene/EtOAc, 10:1→1:1) gave 2-acetylsulfanylmethyl-3-(6-tert-butoxycarbonylamino-pyridin-3-yl)-2-methyl-propionic acid tert-butyl ester (137 mg, 65%).

(e) 3-(6-Amino-pyridin-3-yl)-2-mercaptomethyl-2-methyl-propionic acid

2-Acetylsulfanylmethyl-3-(6-tert-butoxycarbonylamino-pyridin-3-yl)-2-methyl-propionic acid tert-butyl ester (4 mg, 9.4 μmol) was dissolved in conc. HCl under argon. The solution was heated to reflux for 1 h. Concentration under reduced pressure yielded the title compound as the hydrochloride salt (2.5 mg, 100%).

$^1$H NMR (500 MHz, CD$_3$OD): δ 1.20 (s, 3H), 2.62 (d, 1H), 2.76–2.83 (m, 2H), 2.95 (d, 1H), 6.94 (d, 1H), 7.64 (d, 1H), 7.80 (dd, 1H). MS (+) 227 (M+1).

Example 8

2-(6-Amino-pyridin-3-ylmethyl)-2-mercaptomethyl-butyric acid (a) [5-(5-Ethyl-2,2-dimethyl-4,6-dioxo-[1,3]dioxan-5-ylmethyl)-pyridin-2-yl]-carbamic acid tert-butyl ester (5-Bromomethyl-pyridin-2-yl)-carbamic acid tert-butyl ester (1.0 g, 3.48 mmol) was added to a solution of 2,2-dimethyl-5-ethyl-1,3-dioxane4,6-dione (600 mg, 3.48 mmol) and triethylamine (0.51 mL, 3.66 mmol) in dimethyl sulfoxide (40 mL) under nitrogen. The reaction mixture was stirred over night and water (100 mL) was added. Filtration of the precipitate gave [5-(5-ethyl-2,2-dimethyl-4,6-dioxo-[1,3]dioxan-5-ylmethyl)-pyridin-2-yl]-carbamic acid tert-butyl ester (1.15 g, 87%).

(b) 2-(6-tert-Butoxycarbonylamino-pyridin-3-ylmethyl)-2-ethyl-malonic acid monoethyl ester A solution of sodium metal (140 mg, 6.08 mmol) in ethanol (20 mL) was added to a solution of [5-(5-ethyl-2,2-dimethyl-4,6-dioxo-[1,3]dioxan-5-ylmethyl)-pyridin-2-yl]-carbamic acid tert-butyl ester (1.15 g, 3.04 mmol) in ethanol (10 mL). The reaction was stirred for 90 min. and methylene chloride was then added. The mixture was washed with 0.5 M HCl, dried and concentrated under reduced pressure to give 2-(6-tert-butoxy-carbonylamino-pyridin-3-ylmethyl)-2-ethyl-malonic acid monoethyl ester (1.05 g, 95%).

(c) 2-(6-tert-Butoxycarbonylamino-pyridin-3-ylmethyl)-2-hydroxymethyl-butyric acid ethyl ester Methyl chloroformate (150 pL, 1.95 mmol) was added dropwise to a solution of 2-(6-tert-butoxycarbonylamino-pyridin-3-ylmethyl)-2-ethyl-malonic acid monoethyl ester (700 mg, 1.91 mmol) and $Et_3N$ (275 μL, 1.97 mmol) in THF (15 mL) at −20° C. under nitrogen. The reaction mixture was stirred for 50 min., filtered and added dropwise to a suspension of $NaBH_4$ (80 mg, 2.1 mmol) in THF (15 mL) at −20° C. The reaction was stirred for 16 h at room temperature. 0.2 M HCl was added followed by methylene chloride. The organic phase was washed with brine and dried. Concentration under reduced pressure followed by chromathography (toluene/EtOAc, 3:1→1:3) gave 2-(6-tert-butoxycarbonylamino pyridin-3-ylmethyl)-2-hydroxymethyl-butyric acid ethyl ester (300 mg, 45%).

(d) 2-Acetylsulfanylmethyl-2-(6-tert-butoxycarbonylamino-pyridin-3-ylmethyl)-butyric acid ethyl ester Diisopropyl azodicarboxylate (296 μL, 1.53 mmol) was added dropwise to a solution of triphenylphosphine (402 mg, 1.53 mmol) in THF (4 mL) at 0° C. under argon and the reaction was stirred for 30 min. A solution of thiolacetic acid (109 μL, 1.53 mmol) and 2-(6-tert-butoxycarbonylamino-pyridin-3-ylmethyl)-2-hydroxymethyl-butyric acid ethyl ester (0.27 g, 0.77 mmol) in THF (2 mL) was added dropwise during 10 min. The reaction was stirred for 60 min. at 0° C. and then for 16 h at room temperature. Concentration under reduced pressure followed by chromathography (heptane/EtOAc, 10:1→1:1) gave 2-acetylsulfanylmethyl-2-(6-tert-butoxycarbonylamino-pyridin-3-ylmethyl)-butyric acid ethyl ester (193 mg, 61%).

(e) 2-(6-Amino-pyridin-3-ylmethyl)-2-mercaptomethyl-butyric acid

2-Acetylsulfanylmethyl-2-(6-tert-butoxycarbonylamino-pyridin-3-ylmethyl)-butyric acid ethyl ester (12.3 mg, 30 μmol) was dissolved in conc. HCl (2 mL) under argon. The solution was heated to reflux for 24 h. Concentration under reduced pressure gave the title compound as the hydrochloride salt (8.3 mg, 100%).

$^1H$ NMR (500 MHz, $CD_3OD$): δ 0.91 (t, 3H), 1.71 (m, 2H), 2.68 (m, 2H), 2.92 (m, 2H), 6.96 (d, 1H), 7.65 (bs, 1H), 7.82 (dd, 1H). MS (−) 239 (M−1).

Example 9

3-(6-Amino-5-methyl-pyridin-3-yl)-2-mercaptomethyl-2-methyl-propionic acid (a) 2-[N,N-bis(tert-Butoxycarbonyl)amino]-3-Methyl-5-(2,2,5-trimethyl-4,6-dioxo-[1,3]dioxan-5-ylmethyl)-pyridin 2-[N,N-bis(tert-Butoxycarbonyl)amino]-5-bromomethyl-3-methyl-pyridin (1.6 g, 4.0 mmol) was added to a solution of 2,2,5-trimethyl-1,3-dioxane-4,6-dione (630 mg, 4.0 mmol) and triethylamine (0.58 mL, 4.2 mmol) in dimethyl sulfoxide (40 mL). The reaction mixture was stirred overnight and water (100 mL) was added. The mixture was extracted with EtOAc, the combined organic phases washed with water and brine and dried. Concentration under reduced pressure gave crude 2-[N,N-bis(tert-butoxycarbonyl)amino]-3-methyl-5-(2,2,5-trimethyl-4,6-dioxo-[1,3]dioxan-5-ylmethyl)-pyridin (2.06 g)

(b) 2-(6-[N,N-bis(tert-Butoxycarbonyl)amino]-5-methyl-pyridin-3-ylmethyl)-2-methyl-malonic acid monoethyl ester A solution of sodium metal (184 mg, 8.0 mmol) in ethanol (20 mL) was added to a solution of crude 2-[N,N-bis(tert-butoxycarbonyl)amino]-3-methyl-5-(2,2,5-trimethyl-4,6-dioxo-[1,3]dioxan-5-ylmethyl)-pyridin (2.06 g, ~4.0 mmol) in ethanol (20 mL) under argon. The reaction was stirred for 60 min. and methylene chloride was then added. The mixture was washed with 0.5 M HCl and brine, dried and concented under reduced pressure to give crude 2-(6-[N,N-bis(tert-butoxycarbonyl)amino]-5-methyl-pyridin-3-ylmethyl)-2-methyl-malonic acid monoethyl ester (1.9 g)

(c) 3-(6-[N N-bis(tert-Butoxycarbonyl)amino]-5-methyl-pyridin-3-yl)-2-hydroxymethyl-2-methyl-propionic acid ethyl ester Methyl chloroformate (338 μL, 4.4 mmol) was added dropwise to a solution of crude 2-(6-[N,N-bis(tert-butoxycarbonyl)amino]-5-methyl-pyridin-3-yl methyl)-2-methyl-malonic acid monoethyl ester (1.9 g) and $Et_3N$ (641 μL, 4.6 mmol) in THF (30 mL) at −20° C. The reaction mixture was stirred for 50 min., filtered and added dropwise to a suspension of $NaBH_4$ (182 mg, 4.8 mmol) in THF (30 mL) at −20° C. The reaction was stirred for 16 h at room temperature. 0.5 M HCl was added followed by methylene chloride. The organic phase was washed with brine and dried. Concentration under reduced pressure followed by chromathography (toluene/EtOAc, 10:1→1:3) gave 3-(6-[N,N-bis(tert-butoxycarbonyl)-amino]-5-methyl-pyridin-3-yl)-2-hydroxymethyl-2-methyl-propionic acid ethyl ester (885 mg, 49%).

(d) 2-Acetylsulfanylmethyl-3-(6-[N,N-bis(tert-Butoxycarbonyl)amino]-5-methyl-pyridin-3-yl)-2-methyl-propionic acid ethyl ester Diisopropyl azodicarboxylate (755 μL, 3.91 mmol) was added dropwise to a solution of triphenylphosphine (1.026 g, 3.91 mmol) in THF (10 mL) at 0° C. and the reaction was stirred for 30 min. A solution of thiolacetic acid (279 μL, 3.91 mmol) and 3-(6-[N,N-bis(tert-butoxycarbonyl)amino]-5-methyl-pyridin-3-yl)-2-hydroxymethyl-2-methyl-propionic acid ethyl ester (885 mg, 1.96 mmol) in THF (5 mL) was added dropwise during 10 min. The reaction was stirred for 60 min. at 0° C. and then for 16 h at room temperature. Concentration under reduced pressure followed by chromathography (heptane/EtOAc, 10:1→1:3) gave impure 2-acetylsulfanylmethyl-3-(6-[N,N-bis(tert-butoxycarbonyl)amino]-5-methyl-pyridin-3-yl)-2-methyl-propionic acid ethyl ester (1.46 g)

(e) 2-Acetylsulfanylmethyl-3-(6-amino-5-methyl-pyridin-3-yl)-2-methyl-propionic acid ethyl ester Crude 2-acetylsulfanylmethyl-3-(6-[N,N-bis(tert-butoxycarbonyl)amino]-5-methyl-pyridin-3-yl)-2-methylpropionic acid ethyl ester (1.46 g) was dissolved in TFA (5 mL) and stirred for 60 min. Concentration under reduced pressure followed by chromathography (toluene/EtOAc, 1:1→1:10→0:1) gave slightly impure 2-acetylsulfanylmethyl-3-(6-amino-5-methyl-pyridin-3-yl)-2-methyl-propionic acid ethyl ester (696 mg, 84%)

(f) 3-(6-Amino-5-methyl-pyridin-3-yl)-2-mercaptomethyl-2-methyl-propionic acid

2-Acetylsulfanylmethyl-3-(6-amino-5-methyl-pyridin-3-yl)-2-methyl-propionic acid ethyl ester (17 mg, 40 µmol) was dissolved in conc. HCl (2 mL) under argon. The solution was heated to reflux for 150 min. Concentration under reduced pressure gave the title compound as the hydrochloride salt (10.7 mg, 96%).

$^1$H NMR (500 MHz, CD$_3$OD): δ 1.20 (s, 3H), 2.23 (s, 3H), 2.61 (d, 1H), 2.79 (2d, 2H), 2.94 (d, 1H), 7.55 (m, 1H), 7.69 (m, 1H). MS (+) 241 (M+1).

Example 10

3-Mercapto-2-[(piperidine4-carbonyl)-amino]-propionic acid

CH$_2$Cl$_2$ (70 mL) was added to 4-methoxytrityl chloride resin (7 g, L=0.91 mmol/g 6.37 mmol) under argon and the resin was allowed to swell for 10 min and 2-amino-3-mercapto-propionic acid ethyl ester HCl-salt (5.9 g, 32 mmol) was added. TFA (70 mL) was then added in small portions over 10 min. The slurry was shaken at room temperature for 1 h and concentrated under reduced pressure. When almost dry, toluene (150 mL) was added and the mixture was again concentrated under reduced pressure. This procedure was repeated twice. The now yellow resin was washed with DMF (3×60 mL), CH$_2$Cl$_2$ (2×60 mL), TEA:CH$_2$Cl$_2$ (1:1, 2×60 mL), CH$_2$Cl$_2$ (2×60 mL), MeOH (2×60 mL) and dried under vacuum overnight.

To calculate the loading of 2-amino-3-mercapto-propionic acid ethyl ester on the resin, 50 mg of the product was treated with 10% TFA in CH$_2$Cl$_2$ for 1 minute, and this procedure was repeated 4 times. The mixture was concentrated under reduced pressure to give 2-Amino-3-mercapto-propionic acid ethyl ester (9.8 mg), indicating a loading of about 0.6 mmol/g.

A solution of piperidine-1,4-dicarboxylic acid mono-tert-butyl ester (28 mg, 0.12 mmol) in DMF (1 mL) was added to the resin (100 mg, L=0.6 mmol/g, 0.06 mmol) in a plastic syringe, followed by PyBOP (62 mg, 0.12 mmol) in DMF (0.5 mL) and DIPEA (41 µL, 0.24 mmol). The reaction was left at room temperature for 2 h with occasional stirring and the procedure was repeated once more. The resin was then washed with DMF (2×2 mL), CH$_2$Cl$_2$ (2×2 mL), MeOH (2×2 mL), CH$_2$Cl$_2$ (2×2 mL) and THF (2×2 mL). THF (800 µL) was added to the syringe and the resin was allowed to swell for 10 min. Then water (250 µL) and 10 M NaOH (50 µL) were added. The reaction was left at room temperature for 16 h with occasional stirring. The resin was then washed with THF:water (1:1, 2×2 mL), THF (2×2 mL), CH$_2$Cl$_2$ (2×2 mL), MeOH (2×2 mL) and CH$_2$Cl$_2$ (2×2 mL).

10% TFA in CH$_2$Cl$_2$ (1 mL) was added to the syringe and after 5 min the solution was collected in a tared vial. This procedure was repeated one more time and the combined organic phases were concentrated under reduced pressure to yield the title compound as the TFA salt (15.3 mg, 74%).

$^1$H NMR (500 MHz, CD$_3$OD): δ 1.85–2.10 (m, 4H), 2.65–2.72 (m, 1H), 2.85–2.92 (m, 1H), 2.95–3.08 (m, 3H), 3.40–3.47 (m, 2H), 4.55–4.60 (m, 1H).

Example 11

2-[(Azetidine-2-carbonyl)-amino]-3-mercapto-propionic acid

The title compound was prepared from azetidine-1,2-dicarboxylic acid 1-tert-butyl ester by the method described in Example 14. Yield: 13.8 mg (72%).

$^1$H NMR (500 MHz, CD$_3$OD): δ 2.54–2.63 (m, 1H), 2.82–3.05 (m, 3H), 3.93–4.15 (m, 2H), 4.66–4.71 (m, 1H), 5.05–5.10 (m, 1H).

Example 12

3-Mercapto-2-[(piperidine-3-carbonyl)-amino]-propionic acid

The title compound was prepared from piperidine-1,3-dicarboxylic acid 1-tert-butyl ester by the method described in Example 14. Yield: 15.1 mg (73%).

$^1$H NMR (500 MHz, CD$_3$OD): δ 1.73–2.10 (m, 4H), 2.84–2.92 (m, 2H), 2.95–3.14 (m, 2H), 3.15–3.29 (m, 3H), 4.56–4.62 (m, 1H).

Example 13

2-[(Azetidine-3-carbonyl)-amino]-3-mercapto-propionic acid

The title compound was prepared from azetidine-1,3-dicarboxylic acid mono-tert-butyl ester by the method described in Example 14. Yield: 13.5 mg (71%).

$^1$H NMR (500 MHz, CD$_3$OD): δ 2.86–3.02 (m, 2H), 3.72–3.80 (m, 1H), 4.20–4.24 (d, 4H), 4.62–4.67 (m, 1H).

Example 14

3-(6-Amino-5-methyl-pyridin-3-yl)-2-mercaptomethyl-propionic acid (a) 5-Bromo-2-[N,N-bis(tert-butoxycarbonyl)amino]-3-methyl-pyridin 2-Amino-5-bromo-3-methylpyridine (15.0 g, 80.2 mmol) in tert-butanol was treated with di-tert-butyl dicarbonate (43.6 g, 200 mmol) and DMAP (0.60 g, 4.91 mmol). The reaction mixture was left at ambient temperature overnight and was then concentrated under reduced pressure. Hexane was added and the product precipitated as a solid. Filtering afforded 5-bromo-2-[N,N-bis(tert-butoxycarbonyl)amino]-3-methyl-pyridin (22.0 g, 71%).

(b) 2-[N,N-bis(tert-Butoxycarbonyl)amino]-5-(tert-butyl-dimethyl-silanyloxymethyl)-3-methylpyridin A solution of 5-bromo-2-[N,N-bis(tert-butoxycarbonyl)amino]-3-methyl-pyridin (26.0 g, 67.1 mmol), tert-butyl-dimethyl-tributylstannanylmethoxy-silane (47.6 g, 109 mmol), and bis(triphenylphosphine)palladium(II) dichloride (0.90 g, 1.42 mmol) in 1,2-dichloroethane (80 mL) was stirred at 90° C. for two days. The mixture was cooled to 0° C. and diethyl ether (200 mL) was added followed by saturated aqueous potassium fluoride (40 mL). The mixture was stirred vigourously for 30 min and filtered. The organic phase was washed with water, dried and concentrated under reduced pressure. Flash chromatography (hexane/EtOAc, 100:0→95:5) gave 2-[N,N-bis(tert-butoxycarbonyl)amino]-5-(tert-butyl-dimethyl-silanyloxymethyl)-3-methylpyridin (18.0 g, 59%).

(c) 2-[N,N-bis(tert-butoxycarbonyl)amino]-5-hydroxymethyl-3-methylpyridin

Tetrabutylammonium fluoride (25.1 g 79.6 mmol) was added to a solution of 2-[N,N-bis(tert-butoxycarbonyl)

amino]-5-(tert-butyl-dimethyl-silanyloxymethyl)-3-methylpyridin (18.0 g, 39.8 mmol) in THF (150 mL). The reaction mixture was stirred overnight at room temperature. Concentration under reduced pressure followed by flash chromatography (hexane/EtOAc, 50:50) gave 2-[N,N -bis(tert-butoxycarbonyl)amino]-5-hydroxymethyl-3-methylpyridin (8.0 g, 59%).

(d) 5-Bromomethyl-2-[N,N-bis(tert-butoxycarbonyl)amino]-3-methylpyridin

Triphenylphosphine (7.43 g, 28.3 mmol) and $CBr_4$ (9.49 g, 28.6 mmol) was added to a solution of 2-[N,N-bis(tert-butoxycarbonyl)amino]-5-hydroxymethyl-3-methylpyridin (8.00 g, 23.6 mmol) in dichloromethane (220 mL) at 0° C. The reaction mixture was stirred for 3 h and was then concentrated under reduced pressure. Flash chromatography (hexane/EtOAc, 80:20) gave 5-bromomethyl-2-[N,N-bis(tert-butoxycarbonyl)amino]-3-methylpyridin (8.0 g, 77%).

(e) 2-(6-[N,N-bis(tert-Butoxycarbonyl)amino]-5-methyl-pyridin-3-ylmethyl)- malonic acid diethyl ester To a suspension of NaH (0.24 g, 6.0 mmol, 60%) in DMF (5 mL) was added diethyl malonate (0.91 mL, 6.0 mmol) and the mixture was stirred for 15 min. A solution 2-[N,N-bis(tert-butoxycarbonyl)amino]-5-bromomethyl-3-methyl-pyridin (2.0 g, 5.0 mmol) in DMF (5 mL) was added and the resulting solution stirred for 120 min at 60° C. Ethyl acetate was added and the mixture was washed with water and brine and dried. After evaporation of the solvent, the crude product was purified by flash chromatography ($CH_3OH/CH_2Cl_2$, 1:100→1:20) to give 2-(6-[N,N-bis(tert-butoxycarbonyl)amino]-5-methyl-pyridin-3-ylmethyl)-malonic acid diethyl ester (1.2 g, 50%).

(f) 2-(6-[N,N-bis(tert-butoxycarbonyl)amino]-5-methyl-pyridin-3-ylmethyl)-malonic acid monoethyl ester A solution of KOH (154 mg, 2.75 mmol) in ethanol (2 mL) was added to a solution 2-(6-[N,N-bis(tert-butoxycarbonyl)amino]-5-methyl-pyridin-3-ylmethyl)-malonic acid diethyl ester (1.2 g, 2.50 mmol) in ethanol (10 mL) and methylene chloride (4 mL) at 0° C. The mixture was stirred for 18 h at room temperature. The mixture was concentrated under reduced pressure and the residue dissolved in water. Ethyl acetate was added and the organic layer was washed with 0.5 M HCl, water, brine and dried. After filtration and concentration under reduced pressure gave crude 2-(6-[N,N-bis(tert-butoxy-carbonyl)amino]-5-methyl-pyridin-3-ylmethyl)-malonic acid monoethyl ester (1.0 g, 88%).

(g) 2-(6-[N,N-bis(tert-Butoxycarbonyl)amino]-5-methyl-pyridin-3-ylmethyl)-acrylic acid ethyl ester Diethylamine (0.26 g, 2.67 mmol) was added a mixture of 2-(6-[N,N-bis(tert-butoxycarbonyl)amino]-5-methyl-pyridin-3-ylmethyl)-malonic acid monoethyl ester (1.0 g, 2.2 mmol) and 37% aq. solution of formaldehyde (0.24 g, 3.00 mmol) in methylene chloride (2 mL) at 0° C. The mixture was stirred for 16 h at room temperature and ethyl acetate was added. The organic layer was washed with water and 5% $NaHCO_3$ and dried. Concentration under reduced pressure followed by flash chromatography (toluene/ethyl acetate, 3:1→1:2) gave 2-(6-[N,N-bis(tert-butoxycarbonyl)amino]-5-methyl-pyridin-3-ylmethyl)-acrylic acid ethyl ester (0.68 g, 73%).

(h) 2-Acetylsulfanylmethyl-3-(6-[N,N-bis(tert-butoxycarbonyl)amino]-5-methyl-pyridin-3-yl)-propionic acid ethyl ester Triethylamine (0.234 mL, 1.68 mmol) was added to a solution of 2-(6-[N,N-bis(tert-butoxycarbonyl)amino]-5-methyl-pyridin-3-ylmethyl)-acrylic acid ethyl ester (0.68 g, 1.61 mmol) in thioacetic acid (3 mL) at 0° C. The mixture was stirred at room temperature for 16 h. Ethyl acetate was added and the organic phase was washed with water, saturated $NaHCO_3$ and brine and dried. The crude product was purified by flash chromatography (toluene/ethyl acetate, 3:1→1:2) to give pure 2-acetylsulfanylmethyl-3-(6-[N,N-bis(tert-butoxycarbonyl)amino]-5-methyl-pyridin-3-yl)-propionic acid ethyl ester (489 mg, 61%) and slightly impure 2-acetylsulfanylmethyl-3-(6-[N,N-bis(tert-butoxycarbonyl)amino]-5-methyl-pyridin-3-yl)-propionic acid ethyl ester (0.34 g, 43%).

(i) 3-(6-Amino-5-methyl-pyridin-3-yl)-2-mercaptomethyl-propionic acid

2-Acetylsulfanylmethyl-3-(6-[N,N-bis(tert-butoxycarbonyl)amino]-5-methyl-pyridin-3-yl)-propionic acid ethyl ester (17 mg, 0.034 mmol) was dissolved in conc. HCl (3.0 mL). The solution was heated to reflux for 1 h. Concentration under reduced pressure gave the title compound (8.9 mg, 100%) as the hydrochloride salt.

$^1$H NMR (500 MHz, $CD_3OD$): δ 2.26 (s, 3H), 2.72–2.75 (m, 2H), 2.83–2.91 (m, 3H), 7.60 (s, 1H), 7.77 (s, 1H). MS (+) 227 (M+1).

Example 15

3-(6-Amino4-methyl-pyridin-3-yl)-2-mercaptomethyl-propionic acid (a) 2-Amino-5-bromo-4-methylpyridine 2-Amino-4-methylpyridine (110 g, 1.02 mol) in hydrobromic acid (1 L, 48%) was stirred at 70° C. and a solution of hydrogen peroxide (300 mL, 15%) was added dropwise over a one h at such a rate that the temperature of the reaction mixture remained at 70–80° C. The mixture was stirred for 90 min at 70° C. and poured onto crushed ice. The pH was adjusted to 4–5 with sodium carbonate and the precipitated solid (containing mostly dibrominated products) was filtered off and discarded. The pH was subsequently raised to 9 and the precipitated product collected by filtration. Recrystallization from toluene gave 2-Amino-5-bromo-4-methylpyridine (76.3 g, 40%).

(b) 2-[N,N-bis(tert-Butoxycarbonyl)amino]-5-bromo4-methylpyridin

2-Amino-5-bromo4-methylpyridine (5.70 g, 30.5 mmol) in chloroform was treated with di-tert-butyl dicarbonate (20.0 g, 91.60 mmol) and DMAP (0.60 g, 4.91 mmol). The reaction mixture was left at ambient temperature overnight and was then concentrated under reduced pressure. Flash chromatography (hexane/EtOAc, 95:5) gave 2-[N,N-bis(tert-butoxycarbonyl)amino]-5-bromo4-methylpyridin (8.02 g, 68%).

(c) 2-[N,N-bis(tert-Butoxycarbonyl)amino]-5-(tert-butyl-dimethyl-silanyloxymethyl)-4-methylpyridin A solution of 2-[N,N-bis(tert-butoxycarbonyl)amino]-5-bromo-4-methylpyridin (15.0 g, 38.70 mmol), tert-butyl-dimethyl-tributylstannanylmethoxy-silane (25.4 g, 58.3 mmol), and bis(triphenylphosphine)palladium(II) dichloride (0.90 g, 1.42 mmol) in 1,2dichloroethane (50 mL) was stirred at 90° C. for two days. The mixture was cooled to 0° C. and diethyl ether (200 mL) was added followed by saturated aqueous potassium fluoride (40 mL). The mixture was stirred vigourously for 30 min and filtered. The organic phase was washed with water, dried and concentrated under reduced pressure. Flash chromatography (hexane/EtOAc, 95:5) gave 2-[N,N-bis(tert-butoxycarbonyl)amino]-5-(tert-butyl-dimethyl-silanyloxymethyl)-4-methylpyridin (10.0 g, 57%).

(d) 2-[N,N-bis(tert-butoxycarbonyl)amino]-5-hydroxymethyl-4-methylpyridin

Tetrabutylammonium fluoride (13.9 g, 44.1 mmol) was added to a solution of 2-[N,N-bis(tert-butoxycarbonyl)amino]-5-(tert-butyl-dimethyl-silanyloxymethyl)-4-methylpyridin (10.0 g, 24.3 mmol) in THF (100 mL). The reaction mixture was stirred for 3 h at room temperature. Concentration under reduced pressure followed by flash chromatography (hexane/EtOAc, 50:50) gave 2-[N,N-bis(tert-butoxycarbonyl)amino]-5-hydroxymethyl-4-methylpyridin (5.0 g, 67%).

(e) 5-Bromomethyl-2-[N,N-bis(tert-butoxycarbonyl)amino]-4-methylpyridin

Triphenylphosphine (4.69 g, 17.9 mmol) and CBr$_4$ (4.89 g, 14.8 mmol) was added to a solution of 2-[N,N-bis(tert-butoxycarbonyl)amino]-5-hydroxymethyl-4-methylpyridin (5.00 g, 22.0 mmol) in dichloromethane (130 mL) at 0° C. The reaction mixture was stirred for 3 h and was then diluted with dichloromethane. The organic phase was washed with water, dried and concentrated under reduced pressure. Flash chromatography (hexane/EtOAc, 80:20) gave 5-bromomethyl-2-[N,N-bis(tert-butoxycarbonyl)amino]-4-methylpyridin (5.35 g, 90%).

(f) 2-(6-[N,N-bis(tert-Butoxycarbonyl)amino]-4-methyl-pyridin-3-ylmethyl)-malonic acid diethyl ester To a suspension of NaH (0.24 g, 6.0 mmol, 60%) in DMF (5 mL) was added diethyl malonate (0.91 mL, 6.0 mmol) and the mixture was stirred for 15 min. A solution 2-[N,N-bis(tert-butoxycarbonyl)amino]-5-bromomethyl-4-methylpyridin (2.0 g, 5.0 mmol) in DMF (5 mL) was added and the resulting solution stirred for 120 min at 60 ° C. Ethyl acetate was added and the mixture was washed with water and brine and dried. After evaporation of the solvent, the crude product was purified by flash chromatography (CH$_3$OH/CH$_2$Cl$_2$, 1:100→1:20) to give a pure fraction 2-(6-[N,N-bis(tert-butoxycarbonyl)amino]-4-methyl-pyridin-3-ylmethyl)-malonic acid diethyl ester (1.15 g, 48%) and an impure fraction 2-(6-[N,N-bis(tert-butoxycarbonyl)amino]4-methyl-pyridin-3-ylmethyl)-malonic acid diethyl ester (1.1 g).

(g) 2-(6-[N,N-bis(tert-butoxycarbonyl)amino]-4-methyl-pyridin-3-ylmethyl)-malonic acid monoethyl ester A solution of KOH (141 mg, 2.52 mmol) in ethanol (2 mL) was added to a solution 2-(6-[N,N-bis(tert-butoxycarbonyl)amino]4-methyl-pyridin-3-ylmethyl)-malonic acid diethyl ester (1.1 g, 2.29 mmol) in ethanol (10 mL) and methylene chloride (4 mL) at 0° C. The mixture was stirred for 18 h at room temperature. The mixture was concentrated under reduced pressure and the residue dissolved in water. Ethyl acetate was added and the organic layer was washed with 0.5 M HCl, water, brine and dried. After filtration and concentration under reduced pressure gave crude 2-(6-[N,N-bis(tert-butoxycarbonyl)-amino]-4-methyl-pyridin-3-ylmethyl)-malonic acid monoethyl ester (1.0 g, 97%).

(h) 2-(6-[N,N-bis(tert-butoxycarbonyl)amino]-4-methyl-pyridin-3-ylmethyl)-acrylic acid ethyl ester Diethylamine (0.26 g, 2.67 mmol) was added a mixture of 2-(6-[N,N-bis(tert-butoxycarbonyl)amino]-4-methyl-pyridin-3-ylmethyl)-malonic acid monoethyl ester (1.0 g, 2.2 mmol) and 37% aq. solution of formaldehyde (0.24 g, 3.00 mmol) in methylene chloride (2 mL) at 0° C. The mixture was stirred for 16 h at room temperature and ethyl acetate was added. The organic layer was washed with water and 5% NaHCO$_3$ and dried. Concentration under reduced pressure followed by flash chromatography (toluene/ethyl acetate, 3:1→1:1) gave 2-(6-[N,N-bis(tert-butoxycarbonyl)amino]-4-methyl-pyridin-3-ylmethyl)-acrylic acid ethyl ester (0.81 g, 88%).

(i) 2-Acetylsulfanylmethyl-3-(6-[N,N-bis(tert-butoxycarbonyl)amino]-4-methyl-pyridin-3-yl)-propionic acid ethyl ester Triethylamine (0.279 mL, 2.0 mmol) was added to a solution of 2-(6-[N,N-bis(tert-butoxycarbonyl)amino]-4-methyl-pyridin-3-ylmethyl)-acrylic acid ethyl ester (0.8 g, 1.9 mmol) in thioacetic acid (3 mL) at 0° C. The mixture was stirred at room temperature for 16 h. Ethyl acetate was added and the organic phase was washed with water, saturated NaHCO$_3$ and brine and dried. The crude product was purified by flash chromatography (toluene/ethyl acetate, 3:1→1:2) to give pure 2-acetylsulfanylmethyl-3-(6-[N,N-bis(tert-butoxycarbonyl)amino]-5-methyl-pyridin-3-yl)-propionic acid ethyl ester (200 mg, 21%) and slightly impure 2-acetylsulfanylmethyl-3-(6-[N,N-bis(tert-butoxycarbonyl)amino]-4-methyl-pyridin-3-yl)-propionic acid ethyl ester (0.68 g).

(j) 3-(6Amino-4-methyl-pyridin-3-yl)-2-mercaptomethyl-propionic acid

2-Acetylsulfanylmethyl-3-(6-[N,N-bis(tert-butoxycarbonyl)amino]-4-methyl-pyridin-3-yl)-propionic acid ethyl ester (36 mg, 0.072 mmol) was dissolved in conc. HCl (3.0 mL). The solution was heated to reflux for 1 h. Concentration under reduced pressure gave the title compound (18.7 mg, 98%) as the hydrochloride salt.

$^1$H NMR (500 MHz, CD$_3$OD): δ 2.42 (s, 3H), 2.72–2.95 (m, 5H), 6.81 (s, 1H), 7.58 (s, 1H). MS (+) 227 (M+1).

Example 16

2-Mercaptomethyl-3-piperidin4-yl-butyric acid (a) 4-formyl-piperidine-1-carboxylic acid tert-butyl ester Periodinane (26.9 g, 63.5 mmol) was added to a solution of 1-tert-butoxycarbonyl-piperidine-4-methanol (10.5 g, 48.8 mmol) in methylene chloride (200 mL) and the mixture was stirred for 90 min. Diethyl ether was added and precipitates were removed by extraction with 10% Na$_2$S$_2$O$_3$/saturated NaHCO$_3$ (1:1, 300 mL). The organic layer was washed with 0.5 M NaOH and brine, dried and concentrated under reduced pressure. Flash chromatography (hexane/EtOAc, 8:2) gave 4-formyl-piperidine-1-carboxylic acid tert-butyl ester (8.5 g, 81%).

(b) 2-(1-tert-Butoxycarbonyl-piperidin-4-ylmethylene)-malonic acid diethyl ester To a solution of diethyl malonate (710 μL, 4.7 mmol) and 4-formyl-piperidine-1-carboxylic acid tert-butyl ester (1.0 g,4.7 mmol) in methylene chloride (5 mL) was added piperidine (46 μL, 0.47 mmol) and acetic acid (27 μL, 0.47 mmol). The reaction mixture was stirred for 72 h at room temperature and then for 16 h at 45° C. EtOAc was added and the mixture was washed with water and brine, dried and concentrated under reduced pressure. The crude was purified by flash chromatography (heptane/EtOAc, 3:1→1:3) to give 2-(1-tert-butoxycarbonyl-piperidin4-ylmethylene)-malonic acid diethyl ester (0.69 g 40%).

(c) 2-[1-(1-tert-Butoxycarbonyl-piperidin-4-yl)-ethyl]-malonic acid diethyl ester MeLi (5.34 mL, 8.54 mmol, 1.6 M in diethyl ether) was added dropwise to a slurry of CuI (0.74 g, 3.88 mmol) in THF (5 mL) at −78° C. under argon and the mixture was stirred for 30 min. A solution of 2-(1-tert-butoxycarbonyl-piperidin4-ylmethylene)-malonic acid diethyl ester (0.69 g, 1.94 mmol) in THF (5 mL) was added dropwise and the reacton mixture was stirred for 120 min at −78° C. and was then allowed to warm to room temperature during 60 min. Concentrated aqueous $NH_4OH$ was added and the mixture was then extracted with EtOAc, washed with concentrated aqueous $NH_4OH$ and brine, dried and concentrated under reduced pressure. The crude was purified by flash chromatography (heptane/EtOAc, 3:1→1:6) to give 2-[1-(1-tert-butoxycarbonyl-piperidin-4-yl)-ethyl]-malonic acid diethyl ester (0.39 g, 54%).

(d) 2-[1-(1-tert-Butoxycarbonyl-piperidin-4-yl)-ethyl]-malonic acid monoethyl ester A solution of KOH (84 mg, 1.16 mmol) in EtOH (2 mL) was added dropwise to a solution of 2-[1-(1-tert-butoxycarbonyl-piperidin-4-yl)-ethyl]-malonic acid diethyl ester (0.39 g, 1.01 mmol) in methylene chloride (4 mL) and EtOH (10 mL) at 0° C. The resulting mixture was stirred at room temperature over night. EtOAc was added and the mixture was washed with 0.5 M HCl and brine, dried and concentrated under reduced pressure to give 416 mg of crude 2-[1-(1-tert-butoxycarbonyl-piperidin-4-yl)-ethyl]-malonic acid monoethyl ester.

(e) 4-(2-Ethoxycarbonyl-1-methyl-allyl)-piperidine-1-carboxylic acid tert-butyl ester Formaldehyde (132 mg, 1.65 mmol, 37% in water) was added to a solution of of crude 2-[1-(1-tert-butoxycarbonyl-piperidin4-yl)-ethyl]-malonic acid monoethyl ester (416 mg) in methylene chloride (2 mL) at 0° C. Diethylamine (153 μL, 1.47 mmol) was added dropwise and the mixture was stirred at room temperature over night. EtOAc was added and the mixture was washed with water and saturated $NaHCO_3$, dried and concentrated under reduced pressure. The crude was purified by flash chromatography (toluene/EtOAc, 3:1) to give 4-(2-ethoxycarbonyl-1-methyl-allyl)-piperidine-1-carboxylic acid tert-butyl ester (0.18 g, 49% over two steps).

(f) 4-(3-Acetylsulfanyl-2-ethoxycarbonyl-1-methyl-propyl)-piperidine-1-carboxylic acid tert-butyl ester TEA (86 μL, 0.617 mmol) was added to a solution of 4-(2ethoxycarbonyl-1-methyl-allyl)-piperidine-1-carboxylic acid tert-butyl ester (0.18 g, 0.59 mmol) in thioacetic acid (2 mL) at 0° C. After stirring for 6 h more thioacetic acid (2 mL) was added and the mixture was stirred at 45° C. over night. EtOAc was added and the mixture was washed with water, saturated $NaHCO_3$ and brine, dried and concentrated under reduced pressure. The crude was purified by flash chromatography (toluene/EtOAc, 5:1→1:1) to slightly unpure 4-(3-acetylsulfanyl-2-ethoxycarbonyl-1-methyl-propyl)-piperidine-1-carboxylic acid tert-butyl ester (0.17 g, 75%).

(g) 2-Acetylsulfanylmethyl-3-piperidin-4-yl-butyric acid ethyl ester

TFA (2 mL) was added to a solution of 4-(3-acetylsulfanyl-2-ethoxycarbonyl-1-methyl-propyl)-piperidine-1-carboxylic acid tert-butyl ester (0.17 g, 0.439 mmol) in methylene chloride (10 mL). The reaction was stirred for 90 min and concentrated under reduced pressure. The crude product was purified using HPLC (10→50% acetonitrile in water, 0.1% TFA) to give 2-acetylsulfanylmethyl-3-piperidin4-yl-butyric acid ethyl ester (101 mg, 54%) as the TFA salt.

(h) 2-Mercaptomethyl-3-piperidin-4-yl-butyric acid

Conc. hydrochloric acid (4 mL) was added to 2-acetylsulfanylmethyl-3-piperidin4-yl-butyric acid ethyl ester TFA salt (0.101 g, 0.252 mmol) under argon. The reaction was heated to reflux for 5 h and then concentrated under reduced pressure to give a diastereomeric mixture of the title compound (73.7 mg) as the hydrochloride salt.

$^1$H NMR (500 MHz, $CD_3OD$) for the major diastereomer: δ 1.10 (d, 3H), 1.36–1.58 (m, 2H), 1.71–1.78 (m, 2H), 1.93–1.99 (m, 1H), 2.05–2.11 (m, 1H), 2.60–2.66 (m, 2H), 2.80–2.86 (m, 1H), 2.94–3.02 (m, 2H), 3.38–3.45 (M, 2H). MS (+) 218 (M+1).

Example 17

3-(6-Amino-pyridin-3-yl)-2-mercaptomethyl-butyric acid

(a) (5-formyl-pyridin-2-yl)-carbamic acid tert-butyl ester 5 (5-hydroxymethyl-pyridin-2-yl)-carbamic acid tert-butyl ester (7.00 g, 31.2 mmol) was dissolved in dry DMSO (50 mL) and the reaction flask immersed in a waterbath at 15° C. TEA (13.1 ml, 94.0 mmol) was added, followed by sulfur trioxide pyridine complex (15.0 g, 94.0 mmol) in portions. The reaction mixture was stirred for further 45 min and poured onto crushed ice. The product was extracted with diethyl ether and the combined organic extracts were washed with brine, dried and concentrated under reduced pressure. Recrystallisation from hexane/$CH_2Cl_2$ afforded (5-formyl-pyridin-2-yl)-carbamic acid tert-butyl ester (5.40 g, 78%) as white crystals.

(b) 2-(6-tert-Butoxycarbonylamino-pyridin-3-ylmethylene)-malonic acid diethyl ester To a solution of diethyl malonate (710 μL, 4.7 mmol) and (5-formyl-pyridin-2-yl)-carbamic acid tert-butyl ester (1.04 g, 4.7 mmol) in methylene chloride/DMF (1:1, 5 mL) was added piperidine (46 μL, 0.47 mmol) and acetic acid (27 μL, 0.47 mmol). The reaction mixture was stirred for 72 h at room temperature and then for 16 h at 45° C. Heptane was added slowly to give 2-(6-tertbutoxycarbonylaminopyridin-3-ylmethylene)-malonic acid diethyl ester (0.69 g, 40%) as grey crystals.

(c) 2-[1-(6-tert-Butoxycarbonylamino-pyridin-3-yl)-ethyl]-malonic acid diethyl ester MeLi (6.5 mL, 10.4 mmol, 1.6 M in diethyl ether) was added dropwise to a slurry of CuI (0.9 g, 4.73 mmol) in THF (28 mL) at −78° C. under argon. The reaction mixture was stirred for 30 min. A solution of 2-(6-tert-butoxycarbonylamino-pyridin-3-ylmethylene)-malonic acid diethyl ester (0.84 g, 2.3 mmol) in THF (7 mL) was added dropwise and the reaction was stirred for 180 min at −78° C. Saturated aqueous $NH_4OH$ was added dropwise and the mixture was extracted with EtOAc. The organic phase was washed with saturated aqueous $NH_4OH$ and NaCl, dried and concentrated under reduced pressure. Flash chromatography (toluene/EtOAc, 3:1→1:6) gave 2-[1-(6-tert-butoxycarbonylamino-pyridin-3-yl)-ethyl]-malonic acid diethyl ester (0.723 g, 82.4%) as a white solid.

(d) 2-[1-(6-tert-Butoxycarbonylamino-pyridin-3-yl)-ethyl]-malonic acid monoethyl ester A solution of KOH (113.6 mg, 2.04 mmol) in EtOH (2 mL) was added dropwise to a solution of 2-[1-(6-tert-butoxycarbonylamino-pyridin-3-yl)-ethyl]-malonic acid diethyl ester (0.7 g, 1.84 mmol) in methylene chloride (4 mL) and EtOH (10 mL) at 0° C. under argon and the reaction mixture was stirred over night. 1M KOH (100 mL) was added and the mixture was washed with methylene chloride. The aqueous phase was acidified to pH 2 using 2 M HCl and extracted with EtOAc. The organic phase was dried and concentrated under reduced pressure to give the crude 2-[1-(6-tert-butoxycarbonylamino-pyridin-3-yl)-ethyl]-malonic acid monoethyl ester (423 mg, 65%).

(e) 2-[1-(6-tert-Butoxycarbonylamino-pyridin-3-yl)-ethyl]-acrylic acid ethyl ester Diethylamine (0.153 mL, 1.473 mmol) was added to a solution of 2-[1-(6-tert-butoxycarbonylamino-pyridin-3-yl)-ethyl]-malonic acid monoethyl ester (423 mg, 1.2 mmol) and formaldehyde (132 mg, 1.626 mmol, 36% in water) in methylene chloride (2 mL) at 0° C. under argon. The mixture was stirred at room temperature over night. EtOAc was added and the solution was washed with water, $NaHCO_3$ and brine, dried and concentrated under reduced pressure. Flash chromatography (toluene/EtOAc, 3:1) gave 2-[1-(6-tert-butoxycarbonylamino-pyridin-3-yl)-ethyl]-acrylic acid ethyl ester (158 mg, 41%).

(f) 2-Acetylsulfanylmethyl-3-(6-tert-butoxycarbonylamino-pyridin-3-yl)-butyric acid ethyl ester TEA (0.076 mL, 0.542 mmol) was added to a solution of 2-[1-(6-tert-butoxycarbonylamino-pyridin-3-yl)-ethyl]-acrylic acid ethyl ester (158 mg, 0.493 mmol) in thioacetic acid (2 mL) at 0° C. under argon. The mixture was stirred at 45° C. over night. EtOAc was added and the solution was washed with $NaHCO_3$ and brine, dried and concentrated under reduced pressure. Flash chromatography (toluene/EtOAc, 5:1→1:1) gave slightly unpure 2-acetylsulfanylmethyl-3-(6-tert-butoxycarbonylamino-pyridin-3-yl)-butyric acid ethyl ester (178 mg, 91%).

(g) 2-Acetylsulfanylmethyl-3-(6-amino-pyridin-3-yl)-butyric acid ethyl ester

TFA (2 mL) was added to a solution of 2-acetylsulfanylmethyl-3-(6-tert-butoxycarbonylamino-pyridin-3-yl)-butyric acid ethyl ester (178 mg, 0.449 mmol) in methylene chloride (2 mL). The mixture was stirred for 60 min and concentrated under reduced pressure. Flash chromatography (toluene/EtOAc, 1:6) gave unpure 2-acetylsulfanylmethyl-3-(6-amino-pyridin-3-yl)-butyric acid ethyl ester (176 mg, 95%). Further purification by HPLC (10→70% acetonitrile in water, 0.1% TFA) gave 2-acetylsulfanylmethyl-3-(6-amino-pyridin-3-yl)-butyric acid ethyl ester (104 mg, 56%) as the TFA salt.

(h) 3-(6-Amino-pyridin-3-yl)-2-mercaptomethyl-butyric acid

Conc. hydrochloric acid (4 mL) was added to 2-acetylsulfanylmethyl-3-(6amino-pyridin-3-yl)-butyric acid ethyl ester (104 mg, 0.253 mmol) under argon. The reaction was heated to reflux for 5 h and then concentrated under reduced pressure to give a diastereomeric mixture of the title compound (61 mg, 92%) as the hydrochloride salt.

$^1$H NMR (500 MHz, $D_2O$) for the major diastereomer: δ 1.26 (d, 3H), 2.49–2.53 (m, 2H), 2.64–2.77 (m, 1H), 2.95–3.02 (m, 1H), 7.02 (d, 1H), 7.69 (d, 1H), 7.88 (m, 1H). MS (+) 227 (M+1).

Example 18

3-(6-Amino-2-methyl-pyridin-3-yl)-2-mercaptomethyl-propionic acid (a) (5-Bromo-6-methyl-pyridin-2-yl)-carbamic acid tert-butyl ester 5-Bromo-6-methyl-pyridin-2-ylamine (25.0 g, 133.7 mmol) in THF/tert-butanol (1:10, 550 mL) was treated with di-tert-butyl dicarbonate (39.3 g, 180.0 mmol) and DMAP (2.40 g, 19.6 mmol). The reaction mixture was stirred for 4 h at 40° C. and concentrated under reduced pressure. Flash chromatography (methylene chloride) gave (5-bromo-6-methyl-pyridin-2-yl)-carbamic acid tert-butyl ester (17.0 g, 44%).

(b) [5-(tert-Butyl-dimethyl-silanyloxymethyl)-6-methyl-pyridin-2-yl]-carbamic acid tert-butyl ester A solution of (5-bromo-6-methyl-pyridin-2-yl)-carbamic acid tert-butyl ester (27.5 g, 95.8 mmol), tert-butyl-dimethyl-tributylstannanylmethoxy-silane (43.5 g, 100.2 mmol), and bis(triphenylphosphine)palladium(II) dichloride (1.00 g, 1.40 mmol) in 1,2-dichloroethane (350 mL) was stirred at reflux for 48 h. Additional bis(triphenylphosphine) palladium(II) dichloride (1.00 g, 1.40 mmol) was added every 12 h. The mixture was cooled to 0° C. and diethyl ether (300 mL) was added followed by saturated aqueous potassium fluoride (100 mL). The mixture was stirred vigourously for 60 min and filtered. The organic phase was washed with water, dried and concentrated under reduced pressure. Flash chromatography (MeOH/$CH_2Cl_2$, 1:99) gave [5-(tert-butyl-dimethyl-silanyloxymethyl)-6-methyl-pyridin-2-yl]-carbamic acid tert-butyl ester (15 g, 47%).

(c) (5-Hydroxymethyl-6-methyl-pyridin-2-yl)-carbamic acid tert-butyl ester

Tetrabutylammonium fluoride (19.6 g, 62.4 mmol) was added to a solution of [5-(tert-butyl-dimethyl-silanyloxymethyl)-6-methyl-pyridin-2-yl]-carbamic acid tert-butyl ester (10.5 g, 31.23 mmol) in THF (100 mL) and stirred at room temperature overnight. Water was added and the product extracted with chloroform. The organic phase was dried and concentrated under reduced pressure. Flash chromatography (MeOH/CH$_2$Cl$_2$, 2.5:77.5) gave (5-hydroxymethyl-6-methyl-pyridin-2-yl)-carbamic acid tert-butyl ester (6.0 g, 81%).

(d) 5-Bromomethyl-2-[N,N-bis(tert-butoxycarbonyl) amino]-pyrimidin

Triphenylphosphine (9.83 g, 37.5 mmol) and CBr$_4$ (17.7 g, 53.5 mmol) was added to a solution of (5-hydroxymethyl-6-methyl-pyridin-2-yl)-carbamic acid tert-butyl ester (8.50 g, 35.7 mmol) in dichloromethane (30 mL) at 0° C. The reaction mixture was stirred for 3 h at room temperature and was then diluted with dichloromethane. The organic phase was washed with water, dried and concentrated under reduced pressure. Flash chromatography (CH$_2$Cl$_2$) gave 5-bromomethyl-2-[N,N-bis(tert-butoxycarbonyl)amino]-pyrimidin (4.05 g, 38%).

(e) 2-(6-tert-Butoxycarbonylamino-2-methyl-pyridin-3-ylmethyl)-malonic acid diethyl ester A solution of diethyl malonate (1.21 mL, 7.97 mmol) in DMF (2 mL) was added dropwise to a suspension of NaH (348 mg, 7.97 mmol, 55% in mineral oil) in DMF (5 mL) at 0 ° C. under argon. The reaction mixture was stirred for 45 min and a solution of (5-bromomethyl-6-methyl-pyridin-2-yl)-carbamic acid tert-butyl ester (2.0 g, 6.64 mmol) in DMF (5 mL) was added dropwise. The mixture was stirred over night (0° C.→20° C.). EtOAc was added and the solution was washed with water and brine, dried and concentrated under reduced pressure. Flash chromatography (heptane/ EtOAc, 4:1) gave 2-(6tert-butoxycarbonylamino-2-methyl-pyridin-3-ylmethyl)-malonic acid diethyl ester (1.87 g, 74%).

(f) 2-(6-tert-Butoxycarbonylamino-2-methyl-pyridin-3-ylmethyl)-malonic acid monoethyl ester A solution of KOH (300 mg, 5.35 mmol) in EtOH (4 mL) was added to a solution of 2-(6-tert-butoxycarbonylamino-2-methyl-pyridin-3-ylmethyl)-malonic acid diethyl ester (1.85 g, 4.86 mmol) in EtOH/methylene chloride (2:1, 21 mL) at 0° C. The mixture was stirred for 40 h at room temperature and EtOAc was added. The mixture was washed with 0.5 M HCl and brine, dried and concentrated under reduced pressure to give crude 2-(6-tert-butoxycarbonylamino-2-methyl-pyridin-3-ylmethyl)-malonic acid monoethyl ester (1.45 g).

(g) 2-(6-tert-Butoxycarbonylamino-2-methyl-pyridin-3-ylmethyl)-acrylic acid ethyl ester Diethylamine (359 mg, 4.90 mmol) was added dropwise to a solution of 2-(6-tert-butoxycarbonylamino-2-methyl-pyridin-3-ylmethyl)-malonic acid monoethyl ester (1.44 g, 4.09 mmol) and formaldehyde (464 mg, 5.72 mmol, 37% in water) in methylene chloride (35 mL) at 0° C. under argon. The mixture was stirred at room temperature over night. Methylene chloride was added and the solution was washed with Na$_2$CO$_3$ and brine, dried and concentrated under reduced pressure to give 2-(6-tert-butoxycarbonylamino-2-methyl-pyridin-3-ylmethyl)-acrylic acid ethyl ester (1.03 g, 79%).

(h) 2-Acetylsulfanylmethyl-3-(6-tert-butoxycarbonylamino-2-methyl-pyridin-3-yl)-propionic acid ethyl ester TEA (0.556 mL, 3.99 mmol) was added to a solution of 2-(6-tert-butoxycarbonylamino-2-methyl-pyridin-3-ylmethyl)-acrylic acid ethyl ester (1.23 g, 3.84 mmol) in thioacetic acid (10 mL) at 0 ° C. under argon. The mixture was stirred at room temperature for 64 h. EtOAc was added and the solution was washed with Na$_2$CO$_3$ and brine, dried and concentrated under reduced pressure. Flash chromatography (toluene/EtOAc, 5:1→1:1) gave 2-acetylsulfanylmethyl-3-(6-tert-butoxycarbonylamino-2-methyl-pyridin-3-yl)-propionic acid ethyl ester (1.33 g, 87%).

(i) 3-(6-Amino-2-methyl-pyridin-3-yl)-2-mercaptomethyl-propionic acid

Conc. hydrochloric acid (2 mL) was added to 2-acetylsulfanylmethyl-3-(6-tert-butoxycarbonylamino-2-methyl-pyridin-3-yl)-propionic acid ethyl ester (77 mg, 0.19 mmol) under argon. The reaction was heated to reflux for 110 min and was then concentrated under reduced pressure to give the title compound (39 mg, 76%) as the hydrochloride salt.

$^1$H NMR (500 MHz, D$_2$O): δ 2.49 (s, 3H), 2.73–2.92 (m, 5H), 6.81 (d, 1H), 7.77 (d, 1H). MS (+) 227 (M+1).

Example 19

2-Acetylsulfanylmethyl-3-(2-amino-pyrimidin-5-yl)-propionic acid ethyl ester (a) 2-[N,N-bis(tert-Butoxycarbonyl)amino]-5-bromopyrimidin 2-Amino-5-bromopyrimidine (9.00 g, 51.7 mmol) in THF/tert-butanol (1:1, 100 mL) was treated with di-tert-butyl dicarbonate (34.0 g, 156.0 mmol) and DMAP (3.00 g, 24.5 mmol). The reaction mixture was left at ambient temperature overnight and concentrated under reduced pressure. The residue was partitioned between dichloromethane and water and pH was adjusted to 4 with 1 M HCl. The solution was extracted with dichloromethane, dried and concentrated under reduced pressure. The crude product was suspended in hexane and filtered to yield 2-[N,N-bis(tert-butoxycarbonyl)amino)-5-bromopyrimidin (15.0 g,:77%).

(b) 2-[N,N-bis(tert-Butoxycarbonyl)amino]-5-(tert-butyl-dimethyl-silanyloxymethyl)-pyrimidin A solution of 2-[N,N-bis(tert-butoxycarbonyl)amino]-5-bromopyrimidin (16.0 g, 45.0 mmol), tert-butyl-dimethyl-tributylstannanylmethoxy-silane (20.5 g, 47.1 mmol), and bis(triphenylphosphine)palladium(II) dichloride (1.00 g, 1.40 mmol) in 1,2-dichloroethane (50 mL) was stirred at reflux overnight. Additional bis(triphenylphosphine) palladium(II) dichloride (1.00 g, 1.40 mmol) was added and the solution was refluxed for 8 h. The mixture was cooled to 0° C. and diethyl ether (200 mL) was added followed by saturated aqueous potassium fluoride (50 mL). The mixture was stirred vigourously for 60 min and filtered. The organic phase was washed with water, dried and concentrated under reduced pressure. Flash chromatography (MeOH/CH$_2$Cl$_2$, 1:99) gave 2-[N,N-bis(tert-butoxycarbonyl)amino]-5-(tert-butyl-dimethyl-silanyloxymethyl)-pyrimidin (10.2 g, 55%).

(c) 2-[N,N-bis(tert-Butoxycarbonyl)amino]-5-hydroxymethyl-pyrimidin

Tetrabutylammonium fluoride (15.3 g, 48.6 mmol) was added to a solution of 2-[N,N-bis(tert-butoxycarbonyl) amino]-5-(ter-butyl-dimethyl-silanyloxymethyl)-pyrimidin (10.0 g, 24.3 mmol) in THF (100 mL) and stirred at room temperature overnight. Water was added and the product extracted with chloroform. The organic phase was dried and concentrated under reduced pressure. Flash chromatography (MeOH/CH$_2$Cl$_2$, 2.5:77.5) gave 2-[N,N-bis(tert-butoxycarbonyl)amino]-5-hydroxymethyl-pyrimidin (4.20 g, 53%).

(d) 5-Bromomethyl-2-[N,N-bis(tert-butoxycarbonyl)amino]-pyrimidin

Triphenylphosphine (2.71 g, 10.73 mmol) and CBr$_4$ (4.89 g, 14.8 mmol) was added to a solution of 2-[N,N-bis(tert-butoxycarbonyl)amino]-5-hydroxymethyl-pyrimidin (3.20 g, 9.83 mmol) in dichloromethane (30 mL) at 0° C. The reaction mixture was stirred for 1 h and was then diluted with dichloromethane. The organic phase was washed with water, dried and concentrated under reduced pressure. Flash chromatography (CH$_2$Cl$_2$) gave 5-bromomethyl-2-[N,N-bis(tert-butoxycarbonyl)amino]-pyrimidin (2.55 g, 67%).

(e) 2-(2-[N,N-bis(tert-Butoxycarbonyl)amino]-pyrimidin-5-ylmethyl)-malonic acid diethyl ester A solution of diethyl malonate (0.704 mL, 4.64 mmol) in DMF (2 mL) was added dropwise to a suspension of NaH (200 mg, 4.64 mmol, 55% in mineral oil) in DMF (4 mL) at 0° C. under argon. The reaction mixture was stirred for 30 min and a solution of 5-bromomethyl-2-[N,N-bis(tert-butoxycarbonyl)amino]-pyrimidin (1.5 g, 3.86 mmol) in DMF (4 mL) was added dropwise. The mixture was stirred at room temperature for 3 h. EtOAc was added and the solution was washed with water and brine, dried and concentrated under reduced pressure. Flash chromatography (heptane/EtOAc, 3:2) gave 2-(2-[N,N-bis(tert-butoxycarbonyl)amino]-pyrimidin-5-ylmethyl)-malonic acid diethyl ester (0.87 g, 40%).

(f) 2(2-[N,N-bis(tert-butoxycarbonyl)amino]-pyrimidin-5-ylmethyl)-malonic acid monoethyl ester A solution of KOH (106 mg, 1.88 mmol) in EtOH (2 mL) was added to a solution of 2-(2-[N,N-bis(tert-butoxycarbonyl)amino]-pyrimidin-5-ylmethyl)-malonic acid diethyl ester (0.80 g, 1.71 mmol) in EtOH/methylene chloride (2:1, 12 mL) at 0° C. The mixture was stirred for 16 h at room temperature and EtOAc was added. The mixture was washed with 0.5 M HCl and brine, dried and concentrated under reduced pressure to give 2-(2-[N,N-bis(tert-butoxycarbonyl)amino]-pyrimidin-5-ylmethyl)-malonic acid monoethyl ester (0.67 g, 89%).

(g) 2-(2-[N,N-bis(tert-butoxycarbonyl)amino]-pyrimidin-5-ylmethyl)-acrylic acid ethyl ester Diethylamine (0.124 mL, 1.69 mmol) was added dropwise to a solution of 2-(2-N,N-bis(tert-butoxycarbonyl)amino]-pyrimidin-5-ylmethyl)-malonic acid monoethyl ester (0.62 g, 1.41 mmol) and formaldehyde (160 mg, 2.0 mmol, 37% in water) in methylene chloride (15 mL) at 0° C. under argon. The mixture was stirred at room temperature over night. EtOAc was added and the solution was washed with water, NaHCO$_3$ and brine, dried and concentrated under reduced pressure to give crude 2-(2-[N,N-bis(tert-butoxycarbonyl)-amino]-pyrimidin-5-ylmethyl)-acrylic acid ethyl ester (0.54 g, 94%).

(h) 2-Acetylsulfanylmethyl-3-(2-[N,N-bis(tert-butoxycarbonyl)amino]-pyrimidin-5-yl)-propionic acid ethyl ester TEA (0.189 mL, 1.35 mmol) was added to a solution of 2-(2-[N,N-bis(tert-butoxycarbonyl)amino]-pyrimidin-5-ylmethyl)-acrylic acid ethyl ester (0.53 g, 1.30 mmol) in thioacetic acid (13 mL) at 0° C. under argon. The mixture was stirred at room temperature for 40 h. EtOAc was added and the solution was washed with Na$_2$CO$_3$ and brine, dried and concentrated under reduced pressure. Flash chromatography (heptane/EtOAc, 5:1→1:1) gave 2-acetylsulfanylmethyl-3-(2-[N,N-bis(tert-butoxycarbonyl)amino]-pyrimidin-5-yl)-propionic acid ethyl ester(0.56 g, 89%).

(i) 2-Acetylsulfanylmethyl-3-(2-amino-pyrimidin-5-yl)-propionic acid ethyl ester TFA (1.5 mL) was added to a solution of 2-acetylsulfanylmethyl-3-(2-[N,N-bis(tert-butoxycarbonyl)amino]-pyrimidin-5-yl)-propionic acid ethyl ester (225 mg, 0.46 mmol) in methylene chloride (1.5 mL). The reaction was stirred for 120 min and concentrated under reduced pressure to give the title compound (172 mg, 94%) as the TFA salt.

$^1$H NMR (500 MHz, CD$_3$OD): δ 1.22 (t, 3H), 2.35 (s, 3H), 2.80–3.00 (m, 3H), 3.00–3.22 (m, 2H), 4.13 (q, 2H), 8.43 (s, 2H). MS (+) 284 (M+1).

Example 20

2-(6-Amino-pyridin-3-ylmethyl)-3-mercapto-butyric acid (a) 3-(6-tert-Butoxycarbonylamino-pyridin-3-yl)-2-(diethoxy-phosphoryl)-propionic acid ethyl ester To a suspension of NaH (1.17 g, 60% in mineral oil, 29.3 mmol) in DMF (70 mL) was added triethyl phosphonoacetate (6.01 g, 26.82 mmol) at 0° C. The reaction mixture was allowed to stir at 0 ° C. for 0.5 h. To the reaction was added (5-bromomethyl-pyridin-2-yl)-carbamic acid tert-butyl ester (7.0 g, 24.38 mmol) at 0° C. and the reaction mixture was stirred at room temperature for 16 h. The reaction was quenched with the slow addition of saturated aqueous ammonium chloride (70 mL). The mixture was extracted with EtOAc, washed with brine and dried. The crude product was purified by column chromatography (CH$_2$Cl$_2$/EtOAc, 1:0→1:1→0:1) to give 3-(6-tert-butoxycarbonylamino-pyridin-3-yl)-2-(diethoxy-phosphoryl)-propionic acid ethyl ester (5.1 g, 50%).

(b) 2-(6-tert-Butoxycarbonylamino-pyridin-3-ylmethyl)-but-2-enoic acid ethyl ester To a suspension of NaH (278.8 mg, 60% in mineral oil, 6.97 mmol) in THF (25 mL) at 0° C. was added a solution of 3-(6-tert-butoxycarbonylamino-pyridin-3-yl)-2-(diethoxyphosphoryl)-propionic acid ethyl ester (2.5 g, 5.81 mmol) in THF (30 mL). The reaction mixture was allowed to stir at 0° C. for 1 h. To the reaction was added acetaldehyde (512 mg, 11.6 mmol) dropwise at 0° C. The reaction mixture was allowed to warm to room temperature and then stir for 16 h. Acetaldehyde (2.0 g) was added to the reaction vessel and the reaction mixture was allowed to stir at room temperature for an additional 16 h. The reaction was quenched with the slow addition of saturated aqueous ammonium chloride (30 mL). The mixture was extracted with EtOAc, washed with brine and dried to afford the crude product. The crude product was purified by column chromatography (EtOAc/hexane, 1:8) to give ethyl 2-(6-tert-butoxycarbonylamino-pyridin-3-ylmethyl)-but-2-enoic acid ethyl ester as a mixture of isomers (1.1 g, 60%).

(c) 3-Acetylsulfanyl-2-(6tert-butoxycarbonylamino-pyridin-3-ylmethyl)-butyric acid ethyl ester To thiolacetic acid (15 mL) were added Et$_3$N (1.5 g, 14.8 mmol) and ethyl 2-(6-tert-butoxycarbonylamino-pyridin-3- ylmethyl)-but-2-enoic acid ethyl ester (920 mg, 2.9 mmol) at room temperature. The reaction mixture was stirred at 40–45° C. for 7 days (additional thiolacetic acid (1.5 mL) was added to the reaction mixture every two days). The reaction mixture was cooled to room temperature and then diluted with EtOAc (50 mL). The organic layer was separated, washed with sat. NaHCO₃, brine and dried. The combined organic layers were concentrated under reduced pressure. The crude was purified subsequently by three chromatography columns (CH₂Cl₂, EtOAc/hexane, 1:5 and acetone/hexane, 1:8) to afford 3-acetylsulfanyl-2-(6-tert-butoxycarbonylamino-pyridin-3-ylmethyl)-butyric acid ethyl ester as a diastereometric mixture (780 mg, 68%). The diastereomeric mixture was separated using preparative chiral chromatography according to the procedure described below to give the four isomers 3-acetylsulfanyl-2-(6-tert-butoxycarbonylamino-pyridin-3-ylmethyl)-butyric acid ethyl ester/A, 3-acetylsulfanyl-2-(6-tert-butoxycarbonylamino-pyridin-3-ylmethyl)-butyric acid ethyl ester/B, 3-acetylsulfanyl-2-(6-tert-butoxycarbonylamino-pyridin-3-ylmethyl)-butyric acid ethyl ester/C and 3-acetylsulfanyl-2-(6-tert-butoxycarbonylamino-pyridin-3-yl methyl)-butyric acid ethyl ester/D.

3-Acetylsulfanyl-2-(6-tert-butoxycarbonylamino-pyridin-3 -ylmethyl)-butyric acid ethyl ester/D 3-Acetylsulfanyl-2-(6-tert-butoxycarbonylamino-pyridin-3-yl methyl)-butyric acid ethyl ester/D was separated from a mixture of 3-acetylsulfanyl-2-(6-tert-butoxycarbonylamino-pyridin-3-ylmethyl)-butyric acid ethyl ester/A, 3-acetylsulfanyl-2-(6-tert-butoxycarbonylamino-pyridin-3-ylmethyl)-butyric acid ethyl ester/B, 3-acetylsulfanyl-2-(6-tert-butoxycarbonylamino-pyridin-3-ylmethyl)-butyric acid ethyl ester/C and 3-acetylsulfanyl-2-(6-tert-butoxycarbonylamino-pyridin-3-ylmethyl)-butyric acid ethyl ester/D on a chiralcel OJ column eluting with isohexane:acetonitrile: isopropyl alcohol:diethyl amine (99; 0.5; 0.5; 0.1). The enantiomeric excess was >99% as measured by HPLC using a chiralpak OJ column eluting with isohexane: ethanol: diethyl amine (99; 1; 0.5).

3-Acetylsulfanyl-2-(6-tert-butoxycarbonylamino-pyridin-3-ylmethyl)-butyric acid ethyl ester/A 3-Acetylsulfanyl-2-(6-tert-butoxycarbonylamino-pyridin-3-ylmethyl)-butyric acid ethyl ester/A was separated from a mixture of 3-acetylsulfanyl-2-(6-tert-butoxycarbonylamino-pyridin-3-ylmethyl)-butyric acid ethyl ester/A, 3-acetylsulfanyl-2-(6-tert-butoxycarbonylamino-pyridin-3-ylmethyl)-butyric acid ethyl ester/B and 3-acetylsulfanyl-2-(6-tert-butoxycarbonylamino-pyridin-3-ylmethyl)-butyric acid ethyl ester/C on a chiralcel OJ column eluting with isohexane: 1-propanol: diethyl amine (98; 2; 0.1). The enantiomeric excess was >99% as measured by HPLC using a chiralpak OJ column eluting with isohexane: ethanol: diethyl amine (99; 1; 0.5).

3-Acetylsulfanyl-2-(6tert-butoxycarbonylamino-pyridin-3-ylmethyl)-butyric acid ethyl ester/B 3-Acetylsulfanyl-2-(6-tert-butoxycarbonylamino-pyridin-3-ylmethyl)-butyric acid ethyl ester/B was separated from a mixture of 3-acetylsulfanyl-2-(6-tert-butoxycarbonylamino-pyridin-3-ylmethyl)-butyric acid ethyl ester/B and 3-acetylsulfanyl-2-(6-tert-butoxycarbonylamino-pyridin-3-ylmethyl)-butyric acid ethyl ester/C on a chiralcel AS column eluting with hexane:ethanol:diethyl amine (99: 1: 0.5). The enantiomeric excess was >99% as measured by HPLC using a chiralpak AS column eluting with isohexane:ethanol:diethyl amine (99; 1; 0.5).

3-Acetylsulfanyl-2-(6-tert-butoxycarbonylamino-pyridin-3-ylmethyl)-butyric acid ethyl ester/C 3-Acetylsulfanyl-2-(6-tert-butoxycarbonylamino-pyridin-3-ylmethyl)-butyric acid ethyl ester/C was separated from a mixture of 3-acetylsulfanyl-2-(6-tert-butoxycarbonylamino-pyridin-3-ylmethyl)-butyric acid ethyl ester/B and 3-acetylsulfanyl-2-(6-tert-butoxycarbonylamino-pyridin-3-ylmethyl)-butyric acid ethyl ester/C on a chiralcel AS column eluting with hexane:ethanol:diethyl amine (99: 1: 0.5). The enantiomeric excess was 87% as measured by HPLC using a chiralpak AS column eluting with isohexane:ethanol:diethyl amine (99; 1; 0.5).

(d) 2-(6-Amino-pyridin-3-ylmethyl)-3-mercapto-butyric acid/A

A solution of 3-acetylsulfanyl-2-(6-tert-butoxycarbonylamino-pyridin-3-ylmethyl)-butyric acid ethyl ester/A (45 mg; 0.11 mmol) in concentrated HCl (2 mL) was refluxed under argon for 1 hour. The reaction mixture was allowed to cool to room temperature and concentrated under reduced pressure to afford 28.4 mg of the title compound as the hydrochloride salt.

¹H NMR (400 MHz, D₂O): δ 7.89 (d, 1H), 7.71 (s, 1H), 7.03 (d, 1H), 3.23–3.33 (m, 1H), 3.1–3.2 (m, 1H), 2.75–2.9 (m, 2H), 1.47 (d, 3H). MS(+) 227 (M+1).

(e) 2-(6-Amino-pyridin-3-ylmethyl)-3-mercapto-butyric acid/B

A solution of 3-acetylsulfanyl-2-(6-tert-butoxycarbonylamino-pyridin-3-ylmethyl)-butyric acid ethyl ester/B (55 mg; 0.14 mmol) in concentrated HCl (2 mL) was refluxed under argon for 1 hour. The reaction mixture was allowed to cool to room temperature and concentrated under reduced pressure to afford 39.4 mg of the title compound as the hydrochloride salt.

¹H NMR (400 MHz, D₂O): δ 7.89 (d, 1H), 7.71 (s, 1H), 7.03 (d, 1H), 3.23–3.33 (m, 1H), 3.1–3.2 (m, 1H), 2.75–2.9 (m, 2H), 1.47 (d, 3H). MS(+) 227 (M+1).

(f) 2-(6-Amino-pyridin-3-ylmethyl)-3-mercapto-butyric acid/C

A solution of 3-acetylsulfanyl-2-(6-tert-butoxycarbonylamino-pyridin-3-ylmethyl)-butyric acid ethyl ester/C (9 mg; 0.02 mmol) in concentrated HCL (0.5 mL) was refluxed under 30 argon for 1 hour. The reaction mixture was allowed to cool to room temperature and concentrated under reduced pressure to afford 6.4 mg of the title compound as the hydrochloride salt.

¹H NMR (400 MHz, D₂O): δ 7.82–7.9 (m, 1H), 7.67 (br s, 1H), 7.0 (d, 1H), 3.16–3.28 (m, 1H), 2.96–3.04 (m, 1H), 2.76–2.86 (m, 2H), 1.47 (d, 3H). MS(+) 227 (M+1).

(g) 2-(6-Amino-pyridin-3-ylmethyl)-3-mercapto-butyric acid/D

A solution of 3-acetylsulfanyl-2-(6-tert-butoxycarbonylamino-pyridin-3-ylmethyl)-butyric acid ethyl ester/C (9 mg; 0.02 mmol) in concentrated HCL (0.5 mL) was refluxed under argon for 1 hour. The reaction mixture was allowed to cool to room temperature and concentrated under reduced pressure to afford 6.8 mg of the tide compound as the hydrochloride salt.

$^1$H NMR (400 MHz, D$_2$O): δ 7.82–7.9 (m, 1H), 7.67 (br s, 1H), 7.0 (d, 1H), 3.16–3.28 (m, 1H), 2.96–3.04 (m, 1H), 2.76–2.86 (m, 2H), 1.47 (d, 3H). MS(+) 227 (M+1).

Example 21

6-Amino-pyridin-3-ylmethyl)-3-mercapto-pentanoic acid (a) 2-(6-tert-Butoxycarbonylamino-pyridin-3-ylmethyl)-pent-2-enoic acid ethyl ester To a solution of NaH (290.5 mg, 60% in mineral oil, 7.5 mmol) in THF (25 mL) at 0° C. was added a solution of 3-(6-tert-butoxycarbonylamino-pyridin-3-yl)-2-(diethoxyphosphoryl)-propionic acid ethyl ester (2.5 g, 5.81 mmol) in THF (30 mL). The reaction mixture was allowed to stir at 0° C. for 1 h. To the reaction was added propionaldehyde (725 mg, 12.5 mmol) dropwise at 0° C. The reaction mixture was allowed to stir at room temperature for 16 h. Propionaldehyde (2.5 g) was added and the mixture was stirred at room temperature for an additional 16 h. The reaction was quenched with the slow addition of saturated aqueous NH$_4$Cl (30 mL). The mixture was extracted with EtOAc, washed with brine and dried. The crude product was purified by column chromatography (EtOAc/hexane, 1:8) to give 2-(6tert-butoxycarbonylamino-pyridin-3-ylmethyl)-pent-2-enoic acid ethyl ester as a mixture of isomers (1.2 g, 60%).

(b) 3-Acetylsulfanyl-2-(6-tert-butoxycarbonylamino-pyridin-3-ylmethyl)-pentanoic acid ethyl ester To thiolacetic acid (15 mL) were added Et$_3$N (1.8 g, 17 mmol) and 2-(6-tert-butoxycarbonylamino-pyridin-3-ylmethyl)-pent-2enoic acid ethyl ester (1.1 g, 3.3 mmol) at room temperature. The reaction mixture was stirred at 65° C. for 8 days (additional thioacetic acid (1.5 mL) was added to the reaction mixture every 2 days). The reaction mixture was cooled to room temperature and then diluted with EtOAc. The organic layer was separated, washed with saturated NaHCO$_3$, brine and dried. The combined organic layers were concentrated under reduced pressure. The residue was purified subsequently by two chromatography columns (CH$_2$Cl$_2$ and EtOAc/hexane, 1:5) to afford 350 mg of a mixture of desired products and unreacted starting material. The crude product was further purified by HPLC (EtOH/Hexane, 1:9) and then column chromatography (acetone/hexane, 1:8:) to give the title compound as a diastereometric mixture (180 mg, 18%). The diastereomeric mixture of 3-acetylsulfanyl-2-(6-tert-butoxycarbonylamino-pyridin-3-ylmethyl)-pentanoic acid ethyl ester was separated using preparative chiral chromatography according to the procedure described below to give the four isomers 3-acetylsulfanyl-2-(6-tert-butoxycarbonylamino-pyridin-3-ylmethyl)-pentanoic acid ethyl ester/A, 3-acetylsulfanyl-2-(6-tert-butoxycarbonylamino-pyridin-3-ylmethyl)-pentanoic acid ethyl ester/B, 3-acetylsulfanyl-2-(6-tert-butoxycarbonylamino-pyridin-3-ylmethyl)-pentanoic acid ethyl ester/C and 3-acetylsulfanyl-2-(6-tert-butoxycarbonylamino-pyridin-3-ylmethyl)-pentanoic acid ethyl ester/D. The diastereomeric mixture was separated on two chiralcel OJ columns, which were connected to each other, eluting with isohexane:isopropyl alcohol:methanol (97:1: 2). The enantiomeric excess was measured by analytical HPLC using two chiralcel OJ columns, which were connected to each other, eluting with with isohexane:isopropyl alcohol:methanol (97:1: 2). For 3-acetylsulfanyl-2-(6-tert-butoxycarbonylamino-pyridin-3-ylmethyl)-pentanoic acid ethyl ester A through C the enantiomeric excess was found to be >99%, whereas it was found to be 97% for 3-acetylsulfanyl-2-(6-tert-butoxycarbonyl-amino-pyridin-3-ylmethyl)-pentanoic acid ethyl ester D.

(c) 6-Amino-pyridin-3-ylmethyl)-3-mercapto-pentanoic acid/A

A solution of 3-acetylsulfanyl-2-(6-tert-butoxycarbonylamino-pyridin-3-ylmethyl)-pentanoic acid ethyl ester/A (50.4 mg; 0.12 mmol) in concentrated HCl (2 mL) was refluxed under argon for 1.5 hours. The reaction mixture was allowed to cool to room temperature and concentrated under reduced pressure to afford 33.9 mg of the title compound as the hydrochloride salt.

$^1$H NMR (500 MHz, D$_2$O): δ 7.87 (dd, 1H), 7.67 (d, 1H), 7.0 (d, 1H), 3.02–3.16 (m, 2H), 2.79–2.87 (m, 2H), 1.79–1.88 (m, 1H), 1.53–1.64 (m, 1H), 1.07 (t, 3H). MS(+) 241 (M+1).

(d) 2-(6-Amino-pyridin-3-ylmethyl)-3-mercapto-pentanoic acid/B

A solution of 3-acetylsulfanyl-2-(6-tert-butoxycarbonylamino-pyridin-3-ylmethyl)-pentanoic acid ethyl ester/B (51.6 mg; 0.13 mmol) in concentrated HCl (2 mL) was refluxed under argon for 1.5 hours. The reaction mixture was allowed to cool to room temperature and concentrated under reduced pressure to afford 34.7 mg of the title compound as the hydrochloride salt.

$^1$H NMR (500 MHz, D$_2$O): δ 7.87 (dd, 1H), 7.67 (d, 1H), 7.0 (d, 1H), 3.02–3.16 (m, 2H), 2.79–2.87 (m, 2H), 1.79–1.88 (m, 1H), 1.53–1.64 (m, 1H), 1.07 (t, 3H). MS(+) 241 (M+1).

(e) 2-(6-Amino-pyridin-3-ylmethyl)-3-mercapto-pentanoic acid/C

A solution of 3-acetylsulfanyl-2-(6-tert-butoxycarbonylamino-pyridin-3-ylmethyl)-pentanoic acid ethyl ester/C (4.3 mg; 0.01 mmol) in concentrated HCl (2 mL) was refluxed under argon for 1.5 hours. The reaction mixture was allowed to cool to room temperature and concentrated under reduced pressure to afford 2.9 mg of the title compound as the hydrochloride salt.

$^1$H NMR (500 MHz, D$_2$O): δ 7.86 (dd, 1H), 7.66 (br s, 1H), 7.0 (d, 1H), 2.94–3.04 (m, 2H), 2.74–2.9 (m, 2H), 1.88–1.97 (m, 1H), 1.55–1.66 (m, 1H), 1.05 (t, 3H). MS(+) 241 (M+1).

(f) 2-(6-Amino-pyridin-3-ylmethyl)-3-mercapto-pentanoic acid/D

A solution of 3-acetylsulfanyl-2-(6-tert-butoxycarbonylamino-pyridin-3-ylmethyl)-pentanoic acid ethyl ester/D (19.2 mg; 0.05 mmol) in concentrated HCl (2 mL) was refluxed under argon for 1.5 hours. The reaction mixture was allowed to cool to room temperature and concentrated under reduced pressure to afford 12.9 m, of the title compound as the hydrochloride salt.

$^1$H NMR (500 MHz, D$_2$O): δ 7.86 (dd, 1H), 7.66 (br s, 1H), 7.0 (d, 1H), 2.94–3.04 (m, 2H), 2.74–2.9 (m, 2H), 1.88–1.97 (m, 1H), 1.55–1.66 (m, 1H), 1.05 (t, 3H). MS(+) 241 (M+1).

Example 22

3-(6-Amino-5-chloro-pyridin-3-yl)-2-mercaptomethyl-propionic acid

(a) 6-Amino-5-chloro-nicotinic acid ethyl ester

N-Chlorosuccinimide (21.7 g, 0.162 mol) was added to a suspension of 6-amino-nicotinic acid ethyl ester (18.0 g, 0.108 mol) in acetonitrile (270 ml) and the mixture was refluxed for 2 h. The reaction mixture was filtered and concentrated under reduced pressure. The residue was dissolved in dichloromethane, washed with water and dried. Flash chromatography (2.5% MeOH in $CH_2Cl_2$) gave pure 6-amino-5-chloro-nicotinic acid ethyl ester (17.23 g, 79%).

(b) 6-bis(tert-butoxycarbonyl)-amino-5-chloro-nicotinic acid ethyl ester

DMAP (0.11 g, 0.9 mmol) and $(Boc)_2O$ (21.54 g, 99 mmol) was added to a solution of 6-amino-5-chloro-nicotinic acid ethyl ester (9.0 g, 45 mmol) in dichloromethane (250 ml). The reaction mixture was stirred for 24 h. DMAP (0.02 equiv.) and $(Boc)_2O$ (3×0.5 equiv.) was added during the reaction time. The reaction mixture was washed with water and dried. The crude product was washed with hexane to give pure 6-bis(tert-butoxycarbonyl)-amino-5-chloro-nicotinic acid ethyl ester (11.87 g, 66%).

(c) (3-chloro-5-hydroxymethyl-pyridin-2-yl)-carbamic acid tert-butyl ester $LiAlH_4$ (2.4 g, 63.2 mmol) was added in portions over a period of 3.5 h to solution of 6-bis(tert-butoxycarbonyl)-amino-5-chloro-nicotinic acid ethyl ester (11.5 g, 28.6 mmol) in THF (70 ml) at 0° C. The reaction mixture was stirred in room temperature over night, then $NH_4Cl$ (sat.) was added carefully followed by water. The solution was filtered, dried and concentrated under reduced pressure to yield crude (3-chloro-5-hydroxymethyl-pyridin-2-yl) carbamic acid tert-butyl ester (5.86 g, 79%).

(d) (5-bromomethyl-3-chloro-pyridin-2-yl)-carbamic acid tert-butyl ester

Triphenylphosphine (2.61 g, 9.7 mmol) followed by carbontetrabromide (4.58 g, 13.8 mmol) was added to a suspension of (3-chloro-5-hydroxymethyl-pyridin-2-yl) carbamic acid tert-butyl ester (2.38 g, 9.2 mmol) in $CH_2Cl_2$ (60 ml) at 0° C. The mixture was stirred at room temperature for 5 h and concentrated under reduced pressure. Acetonitrile (40 ml) was added and the mixture was kept to −20° C. overnight. The mixture was then filtered and the crystalline residue washed with cold acetonitrile. The filtrate was concentrated under reduced pressure and another crop of bromide was obtained as described above. (5-bromomethyl-3-chloro-pyridin-2-yl)-carbamic acid tert-butyl ester (1.86 g, 63%) was obtained as white crystals.

(e) 2-(6-tert-butoxycarbonylamino-5-chloro-pyridin-3-ylmethyl)-malonic acid diethyl ester Diethyl malonate (1.87 ml, 12.31 mmol) was added to a suspension of NaH (0.54 g, 12.31 mmol, 55%) in dry DMF (15 ml) at −8° C. This mixture was stirred for 15 min. before it was added dropwise to a solution of (5-bromomethyl-3-chloro-pyridin-2-yl)-carbamic acid tert-butyl ester (3.30 g, 10.26 mmol) in dry DMF (50 ml) at 0° C. The resulting solution was stirred for 40 minutes at 0° C., then $NH_4Cl$ (5 ml, sat.) was added carefully. Stirring at room temperature overnight and concentration under reduced pressure gave a residue, which was dissolved in water/$CH_2Cl_2$. The aqueous layer was extracted with $CH_1Cl_2$ and the combined organic extracts were dried, filtered and concentrated under reduced pressure. Flash chromatography (1% MeOH in $CH_2Cl_2$) gave 2-(6-tert-butoxycarbonylamino-5-chloro-pyridin-3-ylmethyl)-malonic acid diethyl ester (2.45, 60%) as a sticky clear oil.

(f) 2-(6-tert-butoxycarbonylamino-5-chloro-pyridin-3-ylmethyl)-malonic acid monoethyl ester A solution of KOH (0.44 g, 6.72 mmol, 85%) in ethanol (5 ml) was added to a solution of 2-(6-tert-butoxycarbonylamino-5-chloro-pyridin-3-ylmethyl)-malonic acid diethyl ester (2.45 g, 6.11 mmol) in ethanol (25 ml) and methylene chloride (10 ml) at 0° C. The mixture was stirred for 18 h at room temperature. The solvent was evaporated in vacuo and the residue dissolved in water. The aqueous layer was washed with ether, acidified to pH 4 by 1 M HCl and extracted with methylene chloride and ethyl acetate. The combined organic layers were washed with water and brine and dried. Filtration and concentration under reduced pressure gave the crude product which was purified by flash chromatography (10% MeOH in $CH_2Cl_2$) giving 2-(6-tert-butoxycarbonylamino-5-chloro-pyridin-3-ylmethyl)-malonic acid monoethyl ester (1.41 g, 62%) as a yellow-white glassy foam.

(g) 2-(6-tert-butoxycarbonylamino-5-chloro-pyridin-3-ylmethyl)-acrylic acid ethyl ester Diethylamine (3.67 ml, 3.67 mmol) was added dropwise followed by water (2.5 ml) and $CH_2Cl_2$ (2.5 ml) to a mixture of 2-(6-tert-butoxycarbonylamino-5-chloro-pyridin-3-ylmethyl)-malonic acid monoethyl ester (1.40 g, 3.64 mmol) and 37% aq. solution of formaldehyde (0.29 ml, 3.75 mmol) in $CH_2Cl_2$ (2 ml) at 0° C. The mixture was stirred for 20 h at room temperature and then poured onto ice-water and extracted with methylene chloride. The organic layer was washed with 5% $NaHCO_3$, dried and concentrated under reduced pressure. Flash chromatography (1–2.5% methanol in $CH_2Cl_2$) yielded 2-(6-tert-butoxycarbonylamino-5-chloro-pyridin-3-ylmethyl)-acrylic acid ethyl ester 0.81 g (65%).

(h) 2-Acetylsulfanylmethyl-3-(6-tert-butoxycarbonylamino-5-chloro-pyridin-3-ylmethyl)-propionic acid ethyl ester Thioacetic acid (4 ml) was added to a suspension of 2-(6-tert-butoxycarbonylamino-5-chloro-pyridin-3-ylmethyl)-acrylic acid ethyl ester (0.732 g, 2.16 mmol) and triethylamine (0.31 ml, 2.23 mmol) at 0° C. The mixture was stirred at room temperature under argon overnight, poured onto ice-water and extracted with $CH_2Cl_2$. The organic phase was washed with saturated $NaHCO_3$ until gas evolution ceased and then dried. The crude product was purified twice with flash chromatography ($CH_2Cl_2$, 1–2.5% MeOH in $CH_2Cl_2$ and Hexane/EtOAc, 5:2→1:1) to give pure 2-acetylsulfanylmethyl-3-(6-tert-butoxycarbonylamino-5-chloro-pyridin-3-ylmethyl)-propionic acid ethyl ester (0.79 g, 87%).

(i) 3-(6-Amino-5-chloro-pyridin-3-yl)-2-mercaptomethyl-propionic acid

A solution of 2-acetylsulfanylmethyl-3-(6-tert-butoxycarbonylamino-5-chloro-pyridin-3-yl)-propionic acid ethyl ester (55mg, 0.132 mmol) in concentrated HCl (4 mL) was refluxed for 90 min. The reaction was cooled and concentrated under reduced pressure to give the title compound as the HCl salt (36mg, 96.4%)

$^1$H NMR (400 MHz, D$_2$O): δ 2.70–2.97 (m, 5H), 7.73 (s, 1H), 8.09 (s, 1H) MS (+) 248 (M+1)

Example 23

3-(6-Amino5-hydroxymethyl-pyridin-3-yl)-2-mercaptomethyl-propionic acid (a) 6-bis(tert-Butoxycarbonyl)amino-5-vinyl-nicotinic acid ethyl ester A mixture of 5-bromo-6-bis(tert-butoxycarbonyl)amino-nicotinic acid ethyl ester (4.50 g, 10.1 mmol), vinyltributyltin (3.52 g, 11.1 mmol) and tetrakispalladium triphenyphosphin (0.50 g, 0.40 mmol) in THF (15 ml) was stirred at reflux for 24 h. Tetrakispalladium triphenyphosphin (0.50 g) was added and after 24 h at reflux the reaction mixture was cooled and diluted with dichloromethane (100 ml). Saturated aqueous KF (25 ml) was added and the solution stirred for 1 h. Water was added and the product extracted with dichloromethane, the organic phase was dried and concentrated under reduced pressure. Flash chromatography (1% MeOH in dichloromethane) gave 6-bis(tert-butoxycarbonyl)-amino-5-vinyl-nicotinic acid ethyl ester 3.20 g, (81%).

(b) (5-hydroxymethyl-3-vinyl-pyridin-2-yl)carbamic acid tert-butyl ester

DIBAL (25 ml, 1M in hexane) was added dropwise to a solution of 6-bis(tert-butoxycarbonyl)amino-5-vinyl-nicotinic acid ethyl ester (2.00 g, 5.1 mmol) in THF (40 ml) at 0° C. The mixture was stirred at room temperature for 1 h. NH$_4$Cl (sat.) was added carefully followed by water, and the mixture was concentrated under reduced pressure. The residue was suspended in 5% MeOH in dichloromethane and filtered through silicagel. The filtrate was dried and concentrated under reduced pressure to give (5-hydroxymethyl-3-vinyl-pyridin-2-yl)carbamic acid tert-butyl ester (1.00 g, 78%).

(c) (5-bromomethyl-3-vinyl-pyridin-2-yl)carbamic acid tert-butyl ester

To a stirred suspension of (5-hydroxymethyl-3-vinyl-pyridin-2-yl)carbamic acid tert-butyl ester (10.0 g, 40.0 mmol) in CH$_2$Cl$_2$ (150 ml) and THF (60 ml) was added triphenylphosphine (11.5 g, 44.0 mmol) followed by carbontetrabromide (19.9 g, 60.0 mmol) at 0° C. The mixture was stirred at room temperature for 1 h and then concentrated under reduced pressure. Acetonitrile (100 ml) was added and the mixture was kept at −20° C. overnight. The mixture was then filtered and the crystalline residue washed with cold acetonitrile. The product was purified by flash-chromatography (1% MeOH in dichloromethane) to give (5-bromomethyl-3-chloro-pyridin-2-yl)-carbamic acid tert-butyl ester (4.5 g, 36%).

(d) 2-(6-tert-Butoxycarbonylamino-5-vinyl-pyridin-3-ylmethyl)-malonic acid diethyl ester Diethyl malonate (2.30 g, 14.3 mmol) was added to a suspension of NaH (0.61 g, 14.3 mmol, 55%) in dry DMF (75 ml) at 0° C. The mixture was stirred for 15 min and then added dropwise to a solution of (5-bromomethyl-3-chloro-pyridin-2-yl)-carbamic acid tert-butyl ester (4.50 g, 14.3 mmol) in dry DMF (100 ml) at 0° C. The resulting solution was stirred for 40 min at 0° C., then NH$_4$Cl (30 ml, sat.) was added carefully. Concentration under reduced pressure gave a residue, which was dissolved in water/CH$_2$Cl$_2$. The aqueous layer was extracted with CH$_2$Cl$_2$ and the combined extracts were dried, filtered and concentrated under reduced pressure. Flash chromatography (1% MeOH in CH$_2$Cl$_2$) gave 2-(6-tert-Butoxycarbonylamino-5-vinyl-pyridin-3-ylmethyl)-malonic acid diethyl ester (4.30 g, 77%).

(e) 2-(6-tert-Butoxycarbonylamino-5-vinyl-pyridin-3-ylmethyl)-malonic acid monoethyl ester A solution of KOH (0.71 g, 12.6 mmol, 85%) in ethanol (10 ml) was added to a solution of 2-(6-tert-butoxycarbonylamino-5-vinyl-pyridin-3-ylmethyl)-malonic acid diethyl ester (4.30 g, 11.0 mmol) in ethanol (25 ml) and dichloromethane (10 ml) at 0° C. The mixture was stirred for 6 h at room temperature. The solvent was evaporated in vacuo and the residue dissolved in water. The aqueous layer was washed with ether, acidified to pH 4 by 1 M HCl and extracted with dichloromethane. The organic layer was washed with water and brine and dried. Filtration and concentration under reduced pressure followed by flash chromatography (10% MeOH in CH$_2$Cl$_2$) gave 2-(6tert-butoxycarbonylamino5-vinyl-pyridin-3-ylmethyl)-malonic acid monoethyl ester (3.05 g, 76%).

(f) 2-(6-tert-Butoxycarbonylamino-5-vinyl-pyridin-3-ylmethyl)- acrylic acid ethyl ester Diethylamine (0.85 ml, 8.80 mmol) was added dropwise to a mixture of 2-(6-tert-butoxycarbonylamino-5-vinyl-pyridin-3-ylmethyl)-malonic acid monoethyl ester (3.05 g, 8.37 mmol) and 37% aq. solution of formaldehyde (0.71 g, 8.80 mmol) in CH$_2$Cl$_2$ (2 ml) at 0° C. The mixture was stirred for 3 h at room temperature and then poured onto ice-water and extracted with dichloromethane. The organic layer was washed with 5% NaHCO$_3$ and dried. Flash chromatography (1% methanol in CH$_2$Cl$_2$) yielded 2-(6-tert-butoxycarbonylamino-5-vinyl-pyridin-3-ylmethyl)- acrylic acid ethyl ester (1.70 g, 61%).

(g) 2-Acetylsulfanylmethyl-3-(6-tert-butoxycarbonylamino-5-vinyl-pyridin-3-yl)-propionic acid ethyl ester Thioacetic acid (4 ml) was added to a suspension of 2-(6-tert-butoxycarbonylamino-5-vinyl-pyridin-3-ylmethyl)-acrylic acid ethyl ester (0.73 g, 2.16 mmol) in triethylamine (0.31 ml, 2.23 mmol) at 0° C. The mixture was stirred at room temperature under argon overnight, poured onto ice-water and extracted with CH$_2$Cl$_2$. The organic phase was washed with saturated NaHCO$_3$ until gas evolution ceased and then dried. Flash chromatography (1% MeOH in CH$_2$Cl$_2$) gave 2-acetylsulfanylmethyl-3-(6-tert-butoxycarbonylamino-5-chloro-pyridin-3-ylmethyl)-propionic acid ethyl ester (0.51 g, 70%).

(h) 3-(6-tert-butoxycarbonylamino-5-hydroxymethyl-pyridin-3-yl)-mercaptomethyl-propionic acid ethyl ester Ozone was bubbled through a solution of 2-acetylsulfanylmethyl-3-(6-tert-butoxycarbonylamino-5-vinyl-pyridin-3-yl)-propionic acid ethyl ester (0.65 g, 1.60 mmol) in ethanol (25 ml) at −78° C. O$_2$ was then bubbled through the mixture for 5 min followed by N$_2$ bubbling for 15 min. A mixture of NaBH₄ 0.30 g, 8.00 mmol) in water was carefully added to the mixture at −78° C., and the reaction mixture allowed to reach 0° C. Stirring was continued for 3 h. Acetone (10 ml) was added and the reaction mixture evaporated to ⅓ of the initial volume. 50% NaCl (aq) was added and the mixture was extracted with dichloromethane, dried and concentrated under reduced pressure to give crude 3-(6-tert-butoxy-carbonylamino-5-hydroxymethyl-pyridin-3-yl)-mercaptomethyl-propionic acid ethyl ester (0.38 g, 63%).

(i) 2-Acetylsulfanylmethyl-3-(6-tert-butoxycarbonylamino-5-hydroxymethyl-pyridin -3-yl)-propionic acid ethyl ester A mixture of crude 3-(6-tert-butoxycarbonylamino-5-hydroxymethyl-pyridin-3-yl)-mercaptomethyl-propionic acid ethyl ester (0.38 g, 1.0 mmol) and KHCO₃ (0.11 g, 1.1 mmol) in acetic acid anhydride (1 mL) was stirred at room temperature for 5 h. NH₄Cl (sat.) and water was then added. The mixture was extracted with dichloromethane, dried and concentrated under reduced pressure. Flash chromatography (CH₂Cl₂, 2.5% MeOH in CH₂Cl₂) gave 2-acetylsulfanylmethyl-3-(6-tert-butoxycarbonylamino-5-hydroxymethyl-pyridin-3-yl)-propionic acid ethyl ester (0.23 g, 60%).

(i) 3-(6-Amino-5-hydroxymethyl-pyridin-3-yl)-2-mercaptomethyl-propionic acid

A solution of 3-(6-tert-butoxycarbonylamino-5-hydroxymethyl-pyridin-3-yl)-2-mercaptomethyl-propionic acid ethyl ester (50 mg, 135 mmol) in concentrated HCl (2 mL) was refluxed for 60 min. The reaction was cooled and concentrated under reduced pressure to give the title compound as the HCl salt (37mg, 98.3%).

$^1$H NMR (400 MHz. D₂O): δ 2.70–2.95 (m, 5H), 4.65 (s, 2H), 7.68 (s, 1H), 7.88 (s, 1H) MS (+) 244 (M+1)

Example 24

2-Mercaptomethyl-3-pyrrolidin-3-yl-propionic acid (a) (1 -Benzyl-pyrrolidin-3-yl)-methanol Red-Al (160 mL of a 3.5 M solution in toluene, 560 mmol) was added to a solution of 1-benzyl-5-oxo-pyrrolidine-3-carboxylic acid (20 g, 91 mmol) in dry THF (650 mL) under argon. The reaction mixture was refluxed for 2.5 h and then poured onto a mixture of crushed ice and NaOH (20%). The phases were separated, the aqueous phase was extracted with toluene and the combined organic phases were dried and concentrated under reduced pressure to give 17.9 g of the crude product as a yellow oil.

(b) 3-Hydroxymethyl-pyrrolidine-1-carboxylic acid tert-butyl ester

10% Pd-C (6.1 g) and ammonium formate (10 g, 158 mmol) were added to a solution of (1-Benzyl-pyrrolidin-3-yl)-methanol (6.1 g, 32 mmol) in methanol (220 mL) under argon. After reflux for 15 minutes the reaction mixture was filtered while warm through a pad of celite, the celite was further washed with methanol, and the combined organic phases were concentrated. The residue was dissolved in THF (35 mL) and water (35 mL), the solution was cooled to 0° C. and K₂CO₃ (22 g, 159 mmol) and di-tert-butyl dicarbonate (6.95 g, 32 mmol) were added. The reaction mixture was stirred at room temperature overnight. The THF was removed under reduced pressure, water added and the aqueous phase was extracted with EtOAc. The combined organic phases were dried and concentrated under reduced pressure to give 4.64 g of the crude product. Flash chromatography (Heptane/EtOAc: 1/0→68/32) of the crude product afforded 3-hydroxymethyl-pyrrolidine-1-carboxylic acid tert-butyl ester (3.82 g, 60%) as a colorless oil.

(c) 3-Trifluoromethanesulfonyloxymethyl-pyrrolidine-1-carboxylic acid tert-butyl ester Methanesulfonyl chloride (0.4 mL, 5.17 mmol) was added dropwise to a solution of 3-hydroxymethyl-pyrrolidine-1-carboxylic acid tert-butyl ester (1 g, 4.97 mmol) and triethyl amine (1.04 mL, 7.46 mmol) in CH₂Cl₂ (15 mL) at 0° C. The reaction mixture was stirred at room temperature overnight. After filtration CH₂Cl₂ was added, and the organic phase was washed with 1 M HCl, dried and concentrated under reduced pressure to yield 3-trifluoromethanesulfonyloxymethyl-pyrrolidine-1-carboxylic acid tert-butyl ester (1.4 g 97%).

(d) 3-Bromomethyl-pyrrolidine-1-carboxylic acid tert-butyl ester

A mixture of 3-trifluoromethanesulfonyloxymethyl-pyrrolidine-1-carboxylic acid tert-butyl ester (3.85 g, 13.8 mmol) and LiBr (3.61 g, 42 mmol) in dry acetone (30 mL) was refluxed overnight. The reaction mixture was allowed to cool to room temperature, filtered and concentrated. The residue was dissolved in CH₂Cl₂ and washed with water, dried and concentrated under reduced pressure to give 6 g of the crude product. Purification by flash chromatography (Heptane/EtOAc: 1/0→68/32) afforded of 3-bromomethyl-pyrrolidine-1-carboxylic acid tert-butyl ester (2.84 g, 78%) as a colourless oil.

(e) 2-(1-tert-Butoxycarbonyl-pyrrolidin-3-ylmethyl)-malonic acid diethyl ester

Diethyl malonate (1.93 mL, 12.7 mmol) was added dropwise to a solution of NaH (60%; 0.51 g, 12.8 mmol) in dry THF (15 mL) at 0° C. The mixture was stirred at room temperature for 1 h after which it was added to a refluxed mixture of 3-bromomethyl-pyrrolidine-1-carboxylic acid tert-butyl ester (2.8 g, 10.6 mmol) in dry THF (30 mL). The reaction mixture was further refluxed for 19 h, and then concentrated to almost dryness. Water (1 L) was added, and the product was extracted with CH₂Cl₂. The combined organic phases were dried and concentrated under reduced pressure to yield 3.3 g of the crude product. Purification by flash chromatography (CH₂Cl₂/EtOAc: 1/0→68/32) afforded 2-(1-tert-butoxycarbonyl-pyrrolidin-3-ylmethyl)-malonic acid diethyl ester (1.64 g, 45%).

(f) 2-(1-tert-Butoxycarbonyl-pyrrolidin-3-ylmethyl)-malonic acid monoethyl ester A solution of KOH (0.26 g; 4.6 mmol) in ethanol (7 mL) was added to a solution of 2-(1-tert-butoxycarbonyl-pyrrolidin-3-ylmethyl)-malonic acid diethyl ester (1.52 g; 4.4 mmol) in ethanol (7 mL) at 0° C. The reaction mixture was stirred at room temperature overnight, concentrated under reduced pressure and the residue was dissolved in water (500 mL). The aqueous layer was washed with diethyl ether, acidified to pH. 3 by 0.5 M HCl, and extracted with diethyl ether. The organic phase was dried and concentrated under reduced pressure to yield 2-(1-tert-butoxycarbonyl-pyrrolidin-3-ylmethyl)-malonic acid monoethyl ester (1.13 g, 81%).

(g) 3-(2-Ethoxycarbonyl-allyl)-pyrrolidine-1-carboxylic acid tert-butyl ester Diethyl amine (0.34 mL; 3.3 mmol) was added to a mixture of 2-(1-tert-butoxycarbonyl-pyrrolidin-3-ylmethyl)-malonic acid monoethyl ester (0.69 g, 2.19 mmol) in 36% aqueous solution of formaldehyde (0.27 mL, 3.5 mmol), $CH_2Cl_2$ (1.6 mL) and water (1.6 mL) at 0° C. The reaction mixture was stirred at room temperature overnight, poured onto ice-water (500 mL) and extracted with $CH_2Cl_2$. The combined organic phases were washed with 5% $NaHCO_3$, dried and concentrated under reduced pressure to yield 3-(2-ethoxy-carbonyl-allyl)-pyrrolidine-1-carboxylic acid tert-butyl ester (0.55 g, 87%) as a colourless oil.

(h) 3-(3-Acetylsulfanyl-2-ethoxycarbonyl-propyl)-pyrrolidine-1-carboxylic acid tert-butyl ester Thioacetic acid (5 mL), which had been cooled to 0° C., was added to a mixture of 3-(2-ethoxycarbonyl-allyl)-pyrrolidine-1-carboxylic acid tert-butyl ester (0.72 g; 2.54 mmol) and triethyl amine (0.37 mL; 2.67 mmol) at 0° C. The reaction mixture was stirred at 0° C. for 30 minutes, at room temperature for 23 hours and then poured onto ice-water (400 mL). The aqueous layer was extracted with $CH_2Cl_2$. The combined organic phases were washed with saturated $NaHCO_3$, dried and concentrated under reduced pressure. The crude product was purified by flash chromatography ($CH_2Cl_2$/EtOAc: 1/10→68/32) to yield 3-(3-acetylsulfanyl-2-ethoxycarbonyl-propyl)-pyrrolidine-1-carboxylic acid tert-butyl ester (0.72 g, 79%) as an oil.

(i) 2-Mercaptomethyl-3-pyrrolidin-3-yl-propionic acid

A solution of 3-(3-acetylsulfanyl-2-ethoxycarbonyl-propyl)-pyrrolidine-1-carboxylic acid tert-butyl ester (0.52 g; 1.45 mmol) in concentrated HCl (15 mL) was refluxed under argon for 1 h. The reaction mixture was allowed to cool to room temperature and concentrated under reduced pressure to afford a diasteromeric mixture of the title compound as the hydrochloride salt (0.33 g; 100%).

$^1H$ NMR (500 MHz, $D_2O$): δ 1.60–1.92 (m, 3H), 2.19–2.32 (m, 1H), 2.32–2.42 (m, 1H), 2.66–2.83 (m, 3H), 2.84–2.96 (m, 1H), 3.23–3.32 (m, 1H), 3.40–3.58 (m, 2H). MS (+) 190 (M+1).

Example 25

3-(Cis4-amino-cyclopent-2-enyl)-2-mercaptomethyl-propionic acid

(a) Cis-methanesulfonic acid 4-tert-butoxycarbonylamino-cyclopent-2-enylmethyl ester Methanesulfonyl chloride (0.76 mL, 9.8 mmol) was added to a solution of cis-(4-hydroxymethyl-cyclopent-2-enyl)-carbamic acid tert-butyl ester (2 g, 9.4 mmol) and triethyl amine (1.96 mL, 14.1 mmol) in $CH_2Cl_2$ (30 mL) at 0° C. The reaction mixture was stirred at room temperature overnight. After filtration $CH_2Cl_2$ was added, and the organic phase was washed with 1M HCl, dried and concentrated under reduced pressure to yield of cis- methanesulfonic acid 4-tert-butoxycarbonylamino-cyclopent-2enylmethyl ester (2.64 g, 96%).

(b) Cis-(4-bromomethyl-cyclopent-2-enyl)-carbamic acid tert-butyl ester

A mixture of cis-methanesulfonic acid 4-tert-butoxycarbonylamino-cyclopent-2-enylmethyl ester (2.51 g, 8.6 mmol) and LiBr (2.24 g, 25.8 mmol) in dry acetone (20 mL) was refluxed overnight. The reaction mixture was allowed to cool to room temperature, filtered and concentrated. The residue was dissolved in $CH_2Cl_2$ and washed with water, dried and concentrated under reduced pressure to give of cis-(4bromomethyl-cyclopent-2-enyl)-carbamic acid tert-butyl ester (2.23 g, 94%).

(c) 2-(Cis4-tert-butoxycarbonylamino-cyclopent-2-enylmethyl)-malonic acid diethyl ester Diethyl malonate (1.29 mL, 8.5 mmol) was added to a mixture of NaH (60%, 0.34 g; 8.5 mmol) in DMF (10 mL). After stirring at room temperature for 15 min a solution of cis-(4-bromomethyl-cyclopent-2-enyl)-carbamic acid tert-butyl ester (1.95 g, 7.1 mmol) in DMF (12 mL) was added, and the reaction mixture was stirred at 60° C. for 19 h. EtOAc was added and the organic phase was extracted with water and brine, dried and concentrated under reduced pressure to give 2.44 g of the crude product. Purification by flash chromatography ($CH_2Cl_2$/EtOAc: 1/0→68/32) afforded of 2-(cis-4-tert-butoxycarbonylamino-cyclopent-2-enylmethyl)-malonic acid diethyl ester (1.47 g, 58%).

(d) 2-(Cis4-tert-butoxycarbonylamino-cyclopent-2-enylmethyl)-malonic acid monoethyl ester A solution of KOH (0.19 g; 3.4 mmol) in ethanol (6 mL) was added to a solution of 2-(Cis-4-tert-butoxycarbonylamino-cyclopent-2-enylmethyl)-malonic acid diethyl ester (1.15 g; 3.2 mmol) in ethanol (6 mL) at 0° C. The reaction mixture was stirred at room temperature overnight, concentrated and ice-water (400 mL) was added. The aqueous phase was washed with diethyl ether (the emulsion formed during the extraction was treated with brine in order to get good phase separation), acidified to pH 3 with 0.5 M HCl, and extracted with diethyl ether. The organic phase was dried and concentrated under reduced pressure to afford 2-(cis4-tert-butoxycarbonylamino-cyclopent-2-enylmethyl)-malonic acid monoethyl ester (0.86 g, 81%) as white crystals.

(e) 2-(Cis-4-tert-butoxycarbonylamino-cyclopent-2-enylmethyl)-acrylic acid ethyl ester Diethyl amine (0.31 mL; 3.0 mmol) was added to a mixture of 2-(cis-4-tert-butoxycarbonylamino-cyclopent-2-enylmethyl)-malonic acid monoethyl ester (0.66 g, 2.0 mmol) in 36% aqueous solution of formaldehyde (0.25 mL, 3.2 mmol), $CH_2Cl_2$ (1.6 mL) and water (1.6 mL) at 0° C. The reaction mixture was stirred at room temperature overnight, poured onto ice-water (400 mL) and extracted with $CH_2Cl_2$. During the extraction, phase separation was improved by the addition of brine. The combined organic phases were washed with 5% $NaHCO_3$, dried and concentrated under reduced pressure to yield 2-(cis-4-tert-butoxycarbonylamino-cyclopent-2-enylmethyl)-acrylic acid ethyl ester (0.56 g, 94%) as an oil.

(f) 2-Acetylsulfanylmethyl-3-(cis4-tert-butoxycarbonylamino-cyclopent-2-enyl)-propionic acid ethyl ester Thioacetic acid (4 mL), which had been cooled to 0° C., was added to a mixture of 2-(cis4-tert-butoxycarbonylamino-cyclopent-2-enylmethyl)-acrylic acid ethyl ester (0.56 g, 1.9 mmol) and triethyl amine (0.28 mL, 2.0 mmol) at 0° C. The reaction mixture was stirred at 0° C. for 30 min, at room temperature for 19 h and then poured onto ice-water (400 mL). The aqueous layer was extracted with CH$_2$Cl$_2$. The organic phase was washed with saturated NaHCO$_3$, dried and concentrated under reduced pressure to give 1.7 g of the crude product. Purification by flash chromatography (CH$_2$Cl$_2$/EtOAc: 1/0→68/32) afforded 2-acetylsulfanylmethyl-3-(cis4-tert-butoxycarbonylamino-cyclopent-2-enyl)-propionic acid ethyl ester (0.46 g, 65%).

(g) 3-(Cis4-amino-cyclopent-2-enyl)-2-mercaptomethyl-propionic acid

A solution of 2-acetylsulfanylmethyl-3-(cis4-tert-butoxycarbonylamino-cyclopent-2-enyl)-propionic acid ethyl ester (86 mg, 0.23 mmol) in concentrated HCl (5 mL) was refluxed under argon for 1 h. The reaction mixture was allowed to cool to room temperature and concentrated under reduced pressure to afford a diasteromeric mixture of the title compound as the hydrochloride salt (65 mg).

$^1$H NMR (400 MHz, D$_2$O): δ 1.35–1.47 (m, 2H), 1.60–1.72 (m, 1H), 1.74–1.92 (m, 2H), 1.92–2.04 (m, 1H), 2.67–2.92 (m, 10H), 4.34–4.43 (m, 2H), 5.79–5.85 (br s, 2H), 6.12 (d, 1H), 6.18 (d, 1H).

Example 26

2-Mercaptomethyl-3-piperazin-1-yl-propionic acid (a) 4-(2-Ethoxycarbonyl-allyl)-piperazine-1-carboxylic acid tert-butyl ester To a solution of 2-bromomethyl-acrylic acid ethyl ester (1.93 g, 10 mmol) in N,N-dimethylformamide (25 mL) was added piperazine-1-carboxylic acid tert-butyl ester (1.86 g, 10 mmol) and then, dropwise, ethyl-diisopropyl-amine (1.71 mL, 10 mmol). After stirring for 16 h at room temperature the solvent was removed under reduced pressure and water (50 mL) and dichloromethane (50 mL) were added. After stirring for 2 min the layers were separated, the organic was washed with water and brine, and dried over magnesium sulphate. The solvent was removed under reduced pressure to give crude 4-(2-ethoxycarbonyl-allyl)-piperazine-1-carboxylic acid tert-butyl ester (2.456 g, 82%).

(b) 4-(3-Acetylsulfanyl-2-ethoxycarbonyl-propyl)-piperazine-1-carboxylic acid tert-butyl ester To crude 4-(2-ethoxycarbonyl-allyl)-piperazine-1-carboxylic acid tert-butyl ester (2.45 g, 8.2 mmol) was added thiolacetic acid (7.5 mL) under argon. The mixture was cooled to 0° C. and triethylamine (1.14 mL, 8.2 mmol) was added dropwise. The mixture was then stirred at room temperature for 2 d and thiolacetic acid (2.5 mL) was added. Stirring was continued for 1 d, then aqueous saturated sodium hydrogencarbonate solution was added carefully until neutral reaction and the mixture was extracted three times with dichloromethane. The combined organic layers were washed twice with aqueous saturated sodium hydrogencarbonate solution and once with brine. After drying over magnesium sulphate the solvent was removed under reduced pressure and the residue was purified by column chromatography (silica gel, 1.7% methanol in dichloromethane) to give 4-(3-acetylsulfanyl-2-ethoxycarbonyl-propyl)-piperazine-1-carboxylic acid tert-butyl ester (0.29 g, 9.4%).

(c) 2-Mercaptomethyl-3-piperazin-1-yl-propionic acid

To 4-(3-acetylsulfanyl-2-ethoxycarbonyl-propyl)-piperazine-1-carboxylic acid tert-butyl ester (0.095 g, 0.25 mmol) argon saturated hydrochloric acid (3 mL, 37%) was added and the mixture was heated under argon to reflux for 2.5 h. The solution was concentrated under reduced pressure to give the title compound as the dihydrochloride salt (0.071 g, quantitative.

$^1$H NMR (300 MHz, D$_2$O): δ 3.86–3.49 (m, 10 H), 3.36–3.28 (m, 1 H), 3.01–2.88 (m, 2 H). MS 205 (M+H).

Example 27

3-(6-Amino-pyridin-3-yl)-2-mercaptomethyl-pentanoic acid (a) 2-[1-(6-tert-Butoxycarbonylamino-pyridin-3-yl)-propyl]-malonic acid diethyl ester To a stirred suspension of copper iodide (5.71 g, 30 mmol) in diethyl ether (120 mL) under argon was added ethylmagnesium bromide (3 M solution in diethyl ether, 20 mL, 20 mmol) within 10 min at 0° C. After 5 min stirring the mixture was cooled to –78° C. and a solution of 2-(6tert-butoxycarbonylamino-pyridin-3-ylmethylene)-malonic acid diethyl ester (5.47 g, 15.0 mmol) in tetrahydrofurane (60 mL) was added dropwise with in 0.5 h. During this period tetrahydrofurane (40 mL) was added. The mixture was allowed to stir at –40° C. for 2.5 h. Then a solution of ammonium chloride (5%) in aqueous ammonia solution (5%) was added with vigorous stirring, allowing access of air, and the mixture was warmed up to room temperature. The mixture was extracted twice with ethyl acetate. The combined organic layers were washed successively with aqueous ammonia solution (5%) and brine, and dried over magnesium sulphate. The solvent was removed under reduced pressure and the residue was recrystallised from a mixture of diisopropyl ether and tetrahydrofurane (5:1, vol./vol.) to give 2-[1-(6-tert-butoxycarbonylamino-pyridin-3-yl)-propyl]-malonic acid diethyl ester (3.23 g, 55%).

b) 2-[1-(6-tert-Butoxycarbonylamino-pyridin-3-yl)-propyl]-malonic acid monoethyl ester 2-[1-(6-tert-Butoxycarbonylamino-pyridin-3-yl)-propyl]-malonic acid diethyl ester (3.23 g, 8.19 mmol) was dissolved in a mixture of dichloromethane (12 mL) and ethanol (24 mL, 99.5%). To this solution was added dropwise a solution of potassium hydroxide (0.528 g, 87%, 8.20 mmol) in ethanol (16 mL, 99.5%) at 0° C. over 0.5 h. Stirring was continued for 16 h while the mixture was allowed to warm up to room temperature. After concentration under reduced pressure to 5–10 mL, water (50 mL) was added and the resulting emulsion was stirred for 0.5 h, and then filtered. The filtrate was washed twice with a mixture of ethyl acetate and diethyl ether (2:1, vol/vol). The aqueous layer was acidified by addition of a solution of citric acid in water (10%) to reach a pH of 4 to 5, and extracted three times with ethyl acetate. The combined organic layers were washed with brine, dried over magnesium sulphate, and the solvent was removed under reduced pressure to yield 2-[1-(6-tert-butoxycarbonylamino-pyridin-3-yl)-propyl]-malonic acid monoethyl ester (2.47 g, 82%)

(c) 2-[1-(6-tert-Butoxycarbonyl-pyridin-3-yl)-propyl]-acrylic acid ethyl ester

To a solution of 2-[1-(6-tert-butoxycarbonylamino-pyridin-3-yl)-propyl]-malonic acid monoethyl ester (2.45 g, 6.69 mmol) in dichloromethane (11 mL) were added an aqueous solution of formaldehyde (0.49 mL, 37%) and diethylamine (0.62 mL, 6.4 mmol) at 0° C. After stirring the mixture vigorously for 16 h water (40 mL) and ethyl acetate (40 mL) were added. After additional 2 min stirring at room temperature the layers were separated and the aqueous was extracted twice with ethyl acetate. The combined organic layers were washed with a saturated aqueous solution of sodium hydrogencarbonate and brine. After drying over sodium sulphate the solvent was removed under reduced pressure to afford 2-[1-(6-tert-Butoxycarbonyl-pyridin-3-yl)-propyl]-acrylic acid ethyl ester (1.21 g, 54%).

(d) 2-Acetylsulfanylmethyl-3-(6-tert-butoxycarbonylamino-pyridin-3-yl)-pentanoic acid ethyl ester 2-[1-(1-(6-tert-Butoxycarbonyl-pyridin-3-yl)-propyl]-acrylic acid ethyl ester (1.20 g, 3.59 mmol) was dissolved in thiolacetic acid (4 mL) under argon and triethylamine (0.56 mL, 4.0 mmol) was added. The mixture was heated to 60° C. After 22 h thiolacetic acid (2 mL) was added. After additional 14 h the mixture was cooled to room temperature and a saturated solution of sodium hydrogenacarbonate was added slowly to obtain a neutral solution. This was extracted three times with ethyl acetate. The combined organic layers were washed with aqueous saturated sodium hydrogencarbonate solution and brine, and dried over magnesium sulphate. After concentration under reduced pressure the residue was purified by column chromatography (silica gel, 1.7% methanol in dichloromethane) to yield 2-acetylsulfanylmethyl-3-(6-tert-butoxycarbonylamino-pyridin-3-yl)-pentanoic acid ethyl ester (1.22 g, 83%).

The mixture of diastereomers was separated in preparative scale by chiral chromatography using a Chiralpak AD column (250*4.6 mm) as stationary phase and hexane (mixture of isomers)/ethanol mixture (85:15), containing diethylamine (0.05%) at a flow rate of 1 mL/min with a sample concentration of 5 mg/mL.

The enatiomeric excess was determined analytically by chiral HPLC on the same column with hexane/ethanol mixture (85:15) as eluent.

2-Acetylsulfanylmethyl-3-(6-tert-butoxycarbonylamino-pyridin-3-yl)-pentanoic acid ethyl ester/A Retention time 10.72 min, ee=99%.

2-Acetylsulfanylmethyl-3-(6-tert-butoxycarbonylamino-pyridin-3-yl)-pentanoic acid ethyl ester/B Retention time 14.41 min, ee=98%

2-Acetylsulfanylmethyl-3-(6-tert-butoxycarbonylamino-pyridin-3-yl)-pentanoic acid ethyl ester/C Retention time 23.01 min, ee=98%

2-Acetylsulfanylmethyl-3-(6-tert-butoxycarbonylamino-pyridin-3-yl)-pentanoic acid ethyl ester/D Retention time 29.83 min, ee=97%

(e) 3-(6-Amino-pyridin-3-yl)-2-mercaptomethyl-pentanoic acid

Hydrochloric acid (38%, 4 mL) was added to 2-acetylsulfanylmethyl-3-(6-tert-butoxycarbonylamino-pyridin-3-yl)-pentanoic acid ethyl ester (0.041 g, 0.1 mmol) under argon and the mixture was heated to reflux for 4 h. Concentration under reduced pressure and drying (45° C., 0.3 mbar) afforded the title compound as the hydrochloride salt (0.027 mg, 97%).

3-(6Amino-pyridin-3-yl)-2-mercaptomethyl-pentanoic acid/A

This compound was obtained from 2-acetylsulfanylmethyl-3-(6-tert-butoxycarbonylamino-pyridin-3-yl)-pentanoic acid ethyl ester/A by the method described above.

$^1$H NMR (300 MHz, D$_2$O): δ 7.79 (dd, 1H), 7.69 (d, 1H), 7.05 (d, 1H), 2.81 (m, 2 H), 2.51 (m, 2 H), 1.66 (m, 2 H), 0.72 (t, 3 H). MS+ 241 (M+H).

3-(6-Amino-pyridin-3-yl)-2-mercaptomethyl-pentanoic acid/B

This compound was obtained from 2-acetylsulfanylmethyl-3-(6-tert-butoxycarbonylamino-pyridin-3-yl)-pentanoic acid ethyl ester/B by the method described above.

$^1$H NMR (300 MHz, D$_2$O): δ 7.85 (dd, 1 H), 7.64 (d, 1 H), 7.01 (d, 1 H), 2.98–2.64 (m, 4 H), 1.89 (m, 1H), 1.60 (m, 1 H), 0.74 (t, 3 H). MS+ 241 (M+H).

3-(6-Amino-pyridin-3-yl)-2-mercaptomethyl-pentanoic acid/C

This compound was obtained from 2-acetylsulfanylmethyl-3-(6-tert-butoxycarbonylamino-pyridin-3-yl)-pentanoic acid ethyl ester/C by the method described above.

$^1$H NMR (300 MHz, D$_2$O): δ 7.85 (dd, 1 H), 7.64 (d, 1 H), 7.01 (d, 1 H), 2.98–2.64 (m, 4 H), 1.89 (m, 1 H), 1.60 (m, 1 H), 0.74 (t, 3 H). MS+ 241 (M+H).

3-(6Amino-pyridin-3-yl)-2-mercaptomethyl-pentanoic acid/D

This compound was obtained from 2-acetylsulfanylmethyl-3-(6-tert-butoxycarbonylamino-pyridin-3-yl)-pentanoic acid ethyl ester/D by the method described above.

$^1$H NMR (300 MHz, D$_2$O): δ 7.79 (dd, 1 H), 7.69 (d, 1 H), 7.05 (d, 1 H), 2.81 (m, 2 H), 2.51 (m, 2 H), 1.66 (m, 2 H), 0.72 (t, 3 H). MS+ 241 (M+H).

Example 28

3-(6-Amino-pyridin-3-yl)-2-mercaptomethyl-4-methyl-pentanoic acid

(a) 2-[1-(6-tert-Butoxycarbonylamino-pyridin-3-yl)-2-methyl-propyl]-malonic acid diethyl ester To a stirred solution of copper cyanide (3.58 g, 40 mmol) in tetrahydrofurane (50 mL) at −15° C. a solution of iso-propylmagnesium bromide (40 mL, 2 M, 80 mmol) in tetrahydrofurane was added under argon over 15 min. After additional 15 min stirring a solution of 2-(6-tert-butoxycarbonylamino-pyridin-3-ylmethylene)-malonic acid diethyl ester (3.78 g, 10.4 mmol) in tetrahydrofurane (50 ml) was added dropwise over 15 min. After stirring for 16 h the mixture was allowed to warm up to room temperature. Then a solution of ammonium chloride (5%) in aqueous ammonia solution (5%) was added with vigorous stirring, allowing access of air. The mixture was extracted twice with ethyl acetate. The combined organic layers were washed successively with aqueous ammonia solution (5%) and brine, and dried over magnesium sulphate. The solvent was removed under reduced pressure and the residue was purified by column chromatography (silica gel, 1.7% methanol in dichloromethane) to give crude 2-[1-(6-tert-butoxycarbonylamino-pyridin-3-yl)-2-methyl-propyl]-malonic acid diethyl ester (2.85 g, 25%).

(b) 2-[1-(6-tert-Butoxycarbonylamino-pyridin-3-yl)-2-methyl-propyl]-malonic acid monoethyl ester To a solution of 2-[1-(6-tert-butoxycarbonylamino-pyridin-3-yl)-2-methyl-propyl]-malonic acid diethyl ester (1.569 g, 3.84 mmol) in a mixture of dichloromethane (6 mL) and ethanol (12 mL, 95%) at 0° C. a solution of potassium hydroxide (0.272 g, 85%, 4.2 mmol) in ethanol (6 mL, 95%) was added dropwise over 40 min. After additional 1 h stirring the mixture was allowed to warm up to room temperature and stirring was continued for 18 h. Then water (30 mL) and dichloromethane (30 mL) were added, and after 3 min stirring the layers were separated. The organic was extracted once with water and the combined aqueous were washed once with ether. Then an aqueous solution of citric acid (10%) was added to adjust the pH to 4, and the solution was extracted three times with ethyl acetate. The combined organic layers were washed with brine and dried over magnesium sulphate. After evaporation of the solvent crude 2-[1-(6-tert-butoxycarbonylamino-pyridin-3-yl)-2-methyl-propyl]-malonic acid monoethyl ester (0.94 g, 64%) was obtained.

(c) 2-[1-(6-tert-Butoxycarbonyl-pyridin-3-yl)-2-methyl-propyl]-acrylic acid ethyl ester To a solution of 2-[1-(6-tert-butoxycarbonylamino-pyridin-3-yl)-2-methyl-propyl]-malonic acid monoethyl ester (0.94 g, 2.47 mmol) in dichloromethane (4 mL) were added an aqueous solution of formaldehyde (0.18 mL, 37%) and diethylamine (0.23 mL, 2.32 mmol) at 0° C. After stirring the mixture vigorously for 16 h water (30 mL) and ethyl acetate (30 mL) were added. After additional 2 min stirring at room temperature the layers were separated and the aqueous was extracted twice with ethyl acetate. The combined organic layers were washed with a saturated aqueous solution of sodium hydrogencarbonate and brine. After drying over sodium sulphate the solvent was removed under reduced pressure and the residue was purified by column chromatography (silica gel, 1.7% methanol in dichloromethane) to give 2-[1-(6-tert-butoxycarbonyl-pyridin-3-yl)-2-methyl-propyl]-acrylic acid ethyl ester (0.24 g, 28%).

(d) 2-Acetylsulfanylmethyl-3-(6-tert-butoxycarbonylamino-pyridin-3-yl)-4-methyl-pentanoic acid ethyl ester 2-[1-(6-tert-Butoxycarbonyl-pyridin-3-yl)-2-methyl-propyl]-acrylic acid ethyl ester (0.431 g, 1.24 mmol) was dissolved in thioacetic acid (4 mL) under argon and triethylamine (0.21 mL, 1.5 mmol) was added. The mixture was heated to 60° C. After 24 h thiolacetic acid (2 mL) was added. After additional 20 h the mixture was cooled to room temperature and a saturated solution of sodium hydrogenacarbonate was added slowly to obtain a neutral solution. This was extracted three times with ethyl acetate. The combined organic layers were washed with aqueous saturated sodium hydrogencarbonate solution and brine, and dried over magnesium sulphate. After concentration under reduced pressure the residue was purified by column chromatography (silica gel, 1.7% methanol in dichloromethane) to yield 2-acetylsulfanylmethyl-3-(6-tert-butoxycarbonylamino-pyridin-3-yl)4-methyl-pentanoic acid ethyl ester (0.284 g, 54%) as a mixture of diastereomers (6:1).

(e) 3-(6-Amino-pyridin-3-yl)-2-mercaptomethyl-4-methyl-pentanoic acid

Acetylsulfanylmethyl-3-(6-tert-butoxycarbonylamino-pyridin-3-yl)-4-methyl-pentanoic acid ethyl ester (0.085 g, 0.20 mmol) was dissolved in argon saturated hydrochloric acid (5 mL, 37%) and heated to reflux under argon for 5.5 h. Concentration under reduced pressure and drying at 45° C./0.3 mbar gave the title compound as the hydrochloride salt (0.058 g, 99%) as a mixture of diastereomers (6: 1).

$^1$H NMR (300 MHz, D$_2$O): δ 7.81 (m, 1 H), 7.62 (m, 1 H), 6.98 (m, 1 H), 3.18–3.06 (m, 1 H), 2.93–2.40 (m, 3 H), 2.23–1.93 (m, 1 H), 0.93–0.74 (m, 6 H). MS 255 (M+H)

Example 29

3-(6-Amino-pyridin-3-yl)-2-mercaptomethyl-3-phenyl-propionic acid (a) 2-[(6-tert-Butoxycarbonylamino-pyridin-3-yl)-phenyl-methyl]-malonic acid diethyl ester To a vigorously stirred suspensin of copper(I)cyanide (1.71 g, 19.06 mmol) in dry THF (18 mL) was added a solution of phenylmagnesium bromide (12.7 mL 3 M in ether, 38.11 mmol) at 0° C. under argon. The mixture was allowed to warm to room temperature, giving a dark brown solution. After 150 minutes a solution of 2-(6-tert-butoxycarbonylamino-pyridin-3-ylmethylene)-malonic acid diethyl ester (1.74 g, 4.76 mmol) in dry THF (19 mL) was added at 0° C. The mixture was left stirring for 3 days then aqueous ammonium chloride was added. The aqueous layer was separated and extracted with ethyl acetate. The combined organic layers were washed with brine and dried. Removal of the solvent in vacuo gave a residue, which was suspended in hexane. Filtration of the crystals gave 2-[(6-tert-butoxycarbonylamino-pyridin-3-yl)-phenyl-methyl]-malonic acid diethyl ester (1.85 g, 88%).

(b) 2-[(6-tert-Butoxycarbonylamino-pyridin-3-yl)-phenyl-methyl]-malonic acid monoethyl ester A solution of KOH (0.266 g, 4.11 mmol) in ethanol (14 mL) was added to a solution of 2-[(6-tert-butoxycarbonylamino-pyridin-3-yl)-phenyl-methyl]-malonic acid diethyl ester (1.82 g, 4.11 mmol) in ethanol (12 mL) and methylene chloride (13 mL) at 0° C. The mixture was stirred overnight at room temperature. More KOH (80 mg dissolved in 3 mL ethanol) was added at 0° C. The reaction mixture was stirred for additional 18 h. The mixture was concentrated under reduced pressure and ethyl acetate, and 0.5 M HCl were added to the residue. The organic layer was washed with brine and dried. After filtration and evaporation in vacuo, the residue was suspended in hexane. Filtration of the crystals gave 2-[(6-tert-butoxycarbonylamino-pyridin-3-yl)-phenyl-methyl]-malonic acid monoethyl ester (1.7 g, 98%).

(c) 2-[(6-tert-Butoxycarbonylamino-pyridin-3-yl)-phenyl-methyl]-acrylic acid ethyl ester Diethylamine (0.52 mL, 5.04 mmol) was added to a mixture of 2-[(6-tert-butoxycarbonylamino-pyridin-3-yl)- phenyl-methyl]-malonic acid monoethyl ester (1.7 g, 4.1 mmol) and 37% aq. solution of formaldehyde (0.42 mL, 5.6 mmol) in methylene chloride (6.5 mL) at 0° C. The mixture was stirred overnight at room temperature and then diluted with ethyl acetate. The organic layer was washed with aqueous saturated sodium bicarbonate and is brine and dried. After filtration and evaporation in vacuo the crude product was purified by flash chromatography ($CH_2Cl_2$) to yield 2-[(6-tert-butoxycarbonylamino-pyridin-3-yl)-phenyl-methyl]-acrylic acid ethyl ester (0.36 g, 23%).

(d) 2-Acetylsulfanylmethyl-3-(6-tert-butoxycarbonylamino-pyridin-3-yl)-3-phenyl-propionic acid ethyl ester Triethylamine (0.105 g, 1.04 mmol) was added to a solution of 2-[(6tert-butoxycarbonylamino-pyridin-3-yl)-phenyl-methyl]-acrylic acid ethyl ester (0.36 g, 0.94 mmol) in thioacetic acid (4 mL) at 0° C. under argon. The mixture was heated at 45° C. for 24 h. Ethyl acetate was added and the organic phase was washed with aqueous saturated sodium bicarbonate and brine and dried. After filtration and evaporation in vacuo the crude product was purified by flash chromatography (toluene/ethyl acetate, 1:0→5:1) to give 2-acetylsulfanylmethyl-3-(6-tert-butoxycarbonylamino-pyridin-3-yl)-3-phenyl-propionic acid ethyl ester (0.314 g, 73%).

3-(6-Amino-pyridin-3-yl)-2-mercaptomethyl-3-phenyl-propionic acid

2-Acetylsulfanylmethyl-3-(6-tert-butoxycarbonylamino-pyridin-3-yl )-3-phenyl-propionic acid ethyl ester (58 mg, 0.125 mmol) was dissolved in conc. HCl (3.0 mL). The solution was heated to reflux for 130 min under argon. Concentration under reduced pressure gave the title compound as the hydrochloride salt (41 mg, 100%).

$^1$H NMR (500 MHz, $D_2O$): δ 8.03–7.83 (m, 2H), 7.5–7.3 (m, 5H), 7.05–6.95 (m, 1H), 4.27–4.15 (m, 1H), 3.6–3.45 (m, 1H), 2.84–2.58 (m, 2H). MS (+) 289 (M+1).

Example 30

3-(6-Amino-pyridin-3-yl)-2-mercaptomethyl-4-phenyl-butyric acid

(a) 2-[1-(6-tert-Butoxycarbonylamino-pyridin-3-yl)-2-phenyl-ethyl]-malonic acid diethyl ester To a vigorously stirred suspensin of copper(I)cyanide (0.66 g, 7.32 mmol) in dry THF (5 mL) was added a solution of benzylmagnesium bromide (5 mL 2.93 M in ether, 14.64 mmol) at 0° C. under argon. The mixture was allowed to warm to room temperature, giving a dark brown solution. After 60 minutes a solution of 2-(6-tert-butoxycarbonylamino-pyridin-3-ylmethylene)-malonic acid diethyl ester (0.67 g, 1.83 mmol) in dry THF (4 mL) was added at 0° C. The mixture was stirred overnight at room temperature then aqueous ammonium chloride was added. The aqueous layer was separated and extracted with ethyl acetate. The combined organic layers were washed with brine and dried. Removal of the solvent in vacuo gave a residue which was purified by flash chromatography ($CH_2Cl_2$/ethyl acetate, 1:0→100:15) to give 2-[1-(6-tert-butoxycarbonylamino-pyridin-3-yl)-2-phenyl-ethyl]-malonic acid diethyl ester (0.44 g, 53%).

(b) 2-[ 1 -(6-tert-Butoxycarbonylamino-pyridin-3-yl)-2-phenyl-ethyl]-malonic acid monoethyl ester A solution of KOH (0.067 g, 1.03 mmol) in ethanol (3 mL) was added to a solution of 2-[1-(6-tert-butoxycarbonylamino-pyridin-3-yl)-2-phenyl-ethyl]-malonic acid diethyl ester (0.44g, 0.96 mmol) in ethanol (3 mL) and methylene chloride (2 mL) at 0° C. The mixture was stirred for 48 h at room temperature. The mixture was concentrated under reduced pressure and ethyl acetate and 0.5 M HCl were added to the residue. The organic layer was washed with brine and dried. Filtration and evaporation in vacuo gave 2-[1-(6-tert-butoxycarbonylamino-pyridin-3-yl)-2-phenyl-ethyl]-malonic acid monoethyl ester (0.37, 90%).

(c) 2-[1-(6-tert-Butoxycarbonylamino-pyridin-3-yl)-2-phenyl-ethyl]-acrylic acid ethyl ester Diethylamine (0.27 mL, 2.59 mmol) was added to a mixture of 2-[1-(6-tert-butoxy-carbonylamino-pyridin-3-yl)-2-phenyl-ethyl]-malonic acid monoethyl ester (0.37 g, 0.86 mmol) and 37% aq. solution of formaldehyde (0.22 mL, 2.9 mmol) in methylene chloride (3.5 mL) at 0° C. The mixture was stirred overnight at room temperature. More formaldehyde (0.24 mL) and diethylamine (0.24 mL) was added. Stirring at room temperature was continued for 18 h and ethyl acetate and water was then added. The organic layer was washed with aqueous saturated sodium bicarbonate and brine, dried and concentrated under reduced pressure to give 2-[1-(6-tert-butoxycarbonylaminopyridin-3-yl)-2-phenyl-ethyl]-acrylic acid ethyl ester (0.34 g, 99%).

(d) 2-Acetylsulfanylmethyl-3-(6-tert-butoxycarbonylamino-pyridin-3-yl )4-phenyl-butyric acid ethyl ester Triethylamine (0.096 g, 0.95 mmol) was added to a solution of 2-[1-(6-tert-butoxycarbonylamino-pyridin-3-yl)-2-phenyl-ethyl]-acrylic acid ethyl ester (0.34 g, 0.86 mmol) in thioacetic acid (3.5 mL) at 0° C. under argon. The mixture was heated at 45° C. for 24 h. Ethyl acetate was added and the organic phase was washed with aqueous saturated sodium bicarbonate and brine and dried. After filtration and evaporation in vacuo the crude product was purified by flash chromatography ($CH_2Cl_2$/ethyl acetate, 1:0→100:5) to give 2-acetylsulfanylmethyl-3-(6-tert-butoxycarbonylamino-pyridin-3-yl)-4-phenyl-butyric acid ethyl ester (0.264 g, 65%).

(e) 3-(6-Amino-pyridin-3-yl)-2-mercaptomethyl-4-phenyl-butyric acid

2-Acetylsulfanylmethyl-3-(6-tert-butoxycarbonylamino-pyridin-3-yl)4-phenyl-butyric acid ethyl ester (0.14 g, 0.3 mmol) was dissolved in conc. HCl (5.0 mL). The solution was heated to reflux for 4.5 h under argon. Concentration under reduced pressure gave the title compound as the hydrochloride salt (100 mg, 98%).

$^1$H NMR (500 MHz, $D_2O$): δ 7.90–7.83 (m, 1H), 7.43 (d, 1H), 7.34–7.18 (m, 3H), 7.17–7.06 (m, 2H), 7.01–6.9 (m, 1H), 3.4–2.5 (m, 6H). MS (+) 303 (M+1).

Example 31

2-(6-Amino-pyridin-3-ylmethyl)-3-mercapto-5-phenyl-pentanoic acid

(a) Ethel (E,Z)-2-([6-[(tert-butoxycarbonyl)amino]-3-pyridinyl]methyl)-5-phenyl-2-pentenoate To a suspension of NaH (310 mg, 7.12 mmol, 55% in mineral oil) in THF (25 mL) at 0° C. under argon was added a solution of (ethyl 3-{6-[(tert-butoxycarbonyl)amino]-3- pyridinyl}-2-(diethoxyphosphoryl)propanoate (2.55 g, 5.95 mmol) in THF (25 mL). After 1 h, a solution of 3-phenylpropanal (1.59 g, 11.9 mmol) was added dropwise. The reaction was stirred for 17 h at room temperature, then quenched with NH$_4$Cl (50 mL, sat, aq). The mixture was extracted with ethyl acetate, the organic layer was washed with brine, dried (Na$_2$SO$_4$), filtered and concentrated under reduced pressure. Column chromatography (CH$_2$Cl$_2$/EtOAc 20:1→10.1) gave ethyl (E,Z)-2-({6-[(tert-butoxycarbonyl)amino]-3-pyridinyl}methyl)-5-phenyl-2-pentenoate (2.49 g, 100%).

(b) Ethyl 3-(acetylsulfanyl)-2-({6-[(tert-butoxycarbonyl)amino]-3-pyridinyl}methyl)-5-phenylpentanoate Triethylamine (1.22 mL, 0.617 mmol) was added to a solution of ethyl (E,Z)-2-({6-[(tert-butoxycarbonyl)amino]-3-pyridinyl}methyl)-5-phenyl-2-pentenoate (400 mg, 0.597 mmol) in thioacetic acid (10 mL) at 40° C. After stirring for 90 h., the mixture was concentrated under reduced pressure. Column chromatography (CH$_2$Cl$_2$/EtOAc 20:1→10.1), then (toluene/EtOAc, 10:1) and then (heptane/EtOAc 2:1) gave ethyl 3-(acetylsulfanyl)-2-({6-[(tert-butoxycarbonyl)amino]-3-pyridinyl}methyl)-5-phenylpentanoate (126 mg, 27%) as a diastereomeric mixture 1:1.

(c) 2-(6-Amino-pyridin-3-ylmethyl)-3-mercapto-5-phenyl-pentanoic acid

Ethyl 3-(acetylsulfanyl)-2-({6-[(tert-butoxycarbonyl)amino]-3-pyridinyl}methyl)-5-phenylpentanoate (9 mg, 18.5 μmol) was dissolved in conc. HCl (1 mL) under argon. The solution was heated to reflux for 4.5 h. Concentration under reduced pressure yielded the title compound as the hydrochloride salt (6.4 mg, 98%) as a diastereomeric mixture 1:1.

$^1$H NMR (400 MHz, D$_2$O): δ 1.78–2.20 (m, 2H), 2.70–3.04 (m, 6H), 6.88, 6.92 (2d, 1H), 7.22–7.39 (m, 5H), 7.52, 7.54 (2d, 1H), 7.69, 7.75 (2d, 1H). MS (+) 317 (M+1).

Example 32

3-[3-(6-Amino-pyridin-3-yl)-2-ethoxycarbonyl-propyldisulfanyl]-2-(6-amino-pyridin-3-ylmethyl)-propionic acid ethyl ester (a) 3-[3-(6-tert-Butoxycarbonylamino-pyridin-3-yl)-2-ethoxycarbonyl-propyldisulfanyl]-2-(6tert-butoxycarbonylamino-pyridin-3-ylmethyl)-propionic acid ethyl ester 3-Acetylsulfanyl-2-(6-tert-butoxycarbonylamino-pyridin-3-ylmethyl)-propionic acid ethyl ester (150 mg, 0.392 mmol) was dissolved in ethanol (15 mL) saturated with NH$_3$ (g). After stirring for 160 min., the mixture was concentrated under reduced pressure. The residue was dissolved in EtOH (10 mL) whereafter a solution of 12 in EtOH (0.5 M, 0.784 mL) was added. The reaction was stirred for 30 min. at room temperature, then diluted with CH$_2$Cl$_2$, washed with saturated aqueous Na$_2$S$_2$O$_5$ and saturated aqueous NaHCO3, dried, filtered and concentrated under reduced pressure to give 3-[3-(6-tert-butoxycarbonylamino-pyridin-3-yl)-2-ethoxycarbonyl-propyldisulfanyl]-2-(6-tert-butoxycarbonylamino-pyridin-3-ylmethyl)-propionic acid ethyl ester (130 mg, 98%).

(b) 3-[3-(6-Amino-pyridin-3-yl)-2-ethoxycarbonyl-propyldisulfanyl]-2-(6-amino-pyridin-3-ylmethyl)-propionic acid ethyl ester Etylacetate saturated with HCl (g) (15 mL) was added to a solution of 3-[3-(6tert-butoxycarbonylamino-pyridin-3-yl)-2-ethoxycarbonyl-propyldisulfanyl]-2-(6-tert-butoxycarbonylamino-pyridin-3-ylmethyl)-propionic acid ethyl ester (130 mg, 0.191 mmol) in ethylacetate (7 mL) at 0° C. The reaction was allowed to attain room temperature and was stirred for 19 h, then evaporated under reduced pressure. The residue was dissolved in water, saturated aqueous Na$_2$CO$_3$ was added and the aqueous phase was extracted with CH$_2$Cl$_2$. The organic layer was dried and concentrated under reduced pressure to give the title compound (90 mg, 98%).

$^1$H NMR (400 MHz, CDCl$_3$): δ 1.19 (t, 3H), 1.20 (t, 3H), 2.68–2.86 (m, 6H), 2.90–3.01 (m, 4H), 4.07–4.14 (m, 4H), 6.45 (d, 2H), 7.28 (m, 2H), 7.87 (s, 2H). MS (+) 479 (M+1).

Example 33

3-(6-Amino-pyridin-3-yl)-2-mercaptomethyl-hexanoic acid (a) N-(5-Butyryl-pyridin-2-yl)-2,2-dimethyl-propionamide A solution of N-(5-bromopyridin-2-yl)-2,2-dimethyl-propionamide (3.582 g, 13.9 mmol) in diethyl ether (36 mL) was cooled to –78° C. under argon and n-butyllithium (1.6 M, 19 mL, 30.4 mmol) was added dropwise within 20 min. 5 min after complete addition the mixture was allowed to warm up to 0° C. N-Methoxy-N-methyl butyramide (3.65 g, 27.8 mmol) was added within less than 5 min and stirring was continued for 45 min. The clear solution was acidified with 2 N hydrochloric acid to pH 2. After vigorous stirring for 15 min the mixture was neutralised with sodium hydrogen carbonate and the layers were separated. The aqueous layer was extracted three times with diethyl ether. The combined organic layers were washed with brine, dried and concentrated under reduced pressure. The resulting oil was dried in oil pump vacuum to remove the excess reagent. After flash chromatography (dichloromethane/methanol 60:1) crude N-(5-butyryl-pyridin-2-yl)-2,2-dimethyl-propionamide (2.47 g, 71%) was obtained as a light orange oil which was not purified further.

(b) N-[5-(1-Hydroxy-butyl)-pyridin-2-yl]-2,2-dimethyl-propionamide

To a solution of N-(5-butyryl-pyridin-2-yl)-2,2-dimethyl-propionamide (2.47 g, 9.95 mmol) in ethanol (20 mL) sodium borohydride (185 mg, 5.0 mmol) was added. After 40 min stirring at room temperature the mixture was acidified with 1 N hydrochloric acid to pH 2 and stirred for 10 min. After neutralisation with sodium hydrogencarbonate the mixture was extracted three times with dichloromethane. The combined organic extracts were washed twice with sodium hydrogen carbonate solution and once with brine. After drying and concentration under reduced pressure the residue was purified by flash chromatography (dichloromethane/methanol 30:1) to give N-[5-(1-hydroxy-butyl)-pyridin-2-yl]-2,2-dimethyl-propionamide (1.025 g, 41%).

(c) 2-[1-[6(2,2-Dimethyl-propionylamino)-pyridin-3-yl]-butyl]-malonic acid monoethyl ester To a solution of N-[5-(1-hydroxy-butyl)-pyridin-2-yl]-2, 2-dimethyl-propionamide (1.025 g, 4.09 mmol) in trichloromethane (12 mL), thionylchloride (6 mL) was added and the mixture was heated to 55° C. for 1 h. Then the solution was concentrated under reduced pressure to leave crude N-[5-(1-chloro-butyl)-pyridin-2-yl]-2,2-dimethyl-propionamide hydrochloride as a colourless solid.

To a solution of diethyl malonate (1.31 g, 8.2 mmol) in dimethylformamide (20 mL) sodium hydride (60% dispersion in mineral oil, 350 mg, 8.7 mmol) was added and the mixture was stirred at room temperature for IS min. After cooling to 0° C. the solution of the intermediate N-[5-(1-chloro-butyl)-pyridin-2-yl]-2,2-dimethyl-propionamide hydrochloride in dimethylformamide (5 mL) was added. After 1 h stirring the solvent was concentrated under reduced pressure and ethyl acetate (25 mL) was added followed by ammonium chloride solution (half-saturated) for neutralisation. The layers were separated, the aqueous was extracted with ethyl acetate and the combined organic layers were washed three times with water and brine, and dried. After concentrated under reduced pressure the residue was filtered through silica gel with dichloromethane/methanol mixture (30:1) as solvent.

This crude 2-{1-[6-(2,2-dimethyl-propionylamino)-pyridin-3-yl]-butyl}-malonic acid diethyl ester was dissolved in a mixture of dichloromethane (2.5 mL) and ethanol (5 mL) at 0° C. and a solution of potassium hydroxide (87%, 111 mg, 5.4 mmol) in ethanol (4 mL) was added. The mixture was allowed to warm up slowly to room temperature and stirring was continued for 24 h. Then dichloromethane (20 mL), water (20 mL) and brine (3 mL) was added. The mixture was stirred vigorously for 2 min. Then the layers were separated, the aqueous was washed with dichloromethane. The combined aqueous layers were acidified (pH 5) with citric acid, and extracted three times with dichloromethane. The combined organic layers were washed with brine and dried. Concentration under reduced pressure gave crude 2-[1-{6-(2,2-dimethyl-propionylamino)-pyridin-3-yl]-butyl}-malonic acid monoethyl ester (258 mg, 41%).

(d) 2-{1-[6-(2,2-Dimethyl-propionylamino)-pyridin-3-yl]-butyl}-acrylic acid ethyl ester To a solution of 2-{1-[6-(2,2-dimethyl-propionylamino)-pyridin-3-yl]-butyl}-malonic acid monoethyl ester (712 mg, 1.95 mmol) in THF (6.5 mL) at 0° C. formaldehyde (37% in water, 0.3 mL) was added within 5 min. Stirring was continued for 10 min, then piperidine (0.26 mL, 2.63 mmol) was added dropwise within 10 min. The mixture was allowed to warm up overnight to room temperature. After 14 h the mixture was concentrated under reduced pressure to one third of its volume, then ether and water were added (15 mL each). After 2 min vigorous stirring the layers were separated, the aqueous was extracted with ether and the combined organic layers were washed with water, 4% citric acid, water and brine. Drying and concentration under reduced pressure gave 2-{1-[6-(2,2-dimethyl-propionylamino)-pyridin-3-yl]-butyl}-acrylic acid ethyl ester (550 mg, 85%) as a colourless solid.

(e) 2-Acetylsulfanylmethyl-3-[6-(2,2-dimethyl-propionylamino)-pyridin-3-yl]-hexanoic acid ethyl ester 2-{1-[6-(2,2-Dimethyl-propionylamino)-pyridin-3-yl]-butyl}-acrylic acid ethyl ester (550 mg, 1.65 mmol) was dissolved under argon in thiolacetic acid (4 mL), and triethylamine (0.24 mL, 1.7 mmol) was added dropwise. After stirring for 16 h at 50° C. thiolacetic acid (2 mL) was added and stirring was continued for 14 h. The solution was cooled to room temperature and neutralised by addition of sodium hydrogen carbonate solution. The mixture was extracted three times with ethyl acetate, the combined extracts were washed with sodium hydrogen carbonate solution and brine. After drying and concentration under reduced pressure the residue was purified by flash chromatography (dichloromethane/methanol, 60:1) to give 2-acetylsulfanylmethyl-3-[6-(2,2-dimethyl-propionylamino)-pyridin-3-yl]-hexanoic acid ethyl ester (619 mg, 92%) as a viscous oil.

(f) 3-(6-Amino-pyridin-3-yl)-2-mercaptomethyl-hexanoic acid

2-Acetylsulfanylmethyl-3-[6-(2,2-dimethyl-propionylamino)-pyridin-3-yl]-hexanoic acid ethyl ester (40.4 mg, 99 μmol) was dissolved under argon in aqueous hydrochloric acid (37%, 4.2 mL) and heated under reflux for 2 h. Concentration under reduced pressure (0.3 torr, 40° C.) gave the title compound as the hydrochloride salt (28 mg, 97%).

$^1$H NMR (300 MHz, D$_2$O): δ 7.86 (d, 1H), 7.65 (d, 1H), 7.02 (t, 1H), 2.98–2.42 (m, 4 H). 1.85–1.54 (m, 2 H), 1.19–1.00 (m, 2 H), 0.87–0.77 (m, 3H). MS (+) 255 (M+1).

Example 34

3-(2-Amino-thiazol-5-yl)-2-mercaptomethyl-propionic acid (a) 2-(2-Amino-thiazol-5-ylmethylene)-malonic acid diethyl ester To a solution of 2-amino-thiazole-5-carbaldehyde (47%; 6 g; 23 mmol) in CH$_2$Cl$_2$ (30 mL) and DMF (30 mL), was added 4A molecular sieves, diethyl malonate (3.5 mL; 23 mmol), piperidine (1.1 mL; 11.5 mmol) and acetic acid (0.7 mL; 11.5 mmol). The reaction mixture was stirred at room temperature for 96 hours. Then EtOAc was added, and the reaction mixture was filtered through celite in order to remove the precipitate formed. EtOAc (500 mL) was added to the filtrate, and the organic phase was washed with NaHCO$_3$ and brine. The organic phase was dried and concentrated to yield 4.9 g of the crude product. Addition of petroleum ether to a solution of the crude product in ethanol followed by filtration afforded 2-(2-amino-thiazol-5-ylmethylene)-malonic acid diethyl ester (1.13 g, 18%).

(b) 2-(2-Amino-thiazol-5-ylmethyl)-malonic acid diethyl ester

NaCNBH$_3$ (1.88 g; 29.9 mmol) was added to a stirred solution of 2-(2-amino-thiazol-5-ylmethylene)-malonic acid diethyl ester (1.13 g; 4.2 mmol) in ethanol at 0° C. The pH of the solution was monitored by addition of a small amount of Bromocresol Green to the solution. Concentrated HCl was added dropwise until the solution turned yellow. The ice bath was removed, and the reaction mixture was stirred at room temperature for 5 hours. Water was added and the product was extracted with CH$_2$Cl$_2$. The combined organic phases were dried and concentrated to yield 2-(2-amino-thiazol-5-ylmethyl)-malonic acid diethyl ester (1 g, 87.8%).

(c) 2-(2-tert-Butoxycarbonylamino-thiazol-5-ylmethyl)-malonic acid diethyl ester BOC$_2$O (0.6 g; 27.5 mmol) was added to a solution of triethyl amine (0.4 mL; 30.1 mmol), 4-(dimethylamino) pyridine (0.34 g; 27.8 mmol) and 2-(2-amino-thiazol-5-ylmethyl)-malonic acid diethyl ester (0.75 g; 27.5 mmol) in CH$_2$Cl$_2$ (5 mL) at 0° C. The reaction mixture was stirred at room temperature overnight. Additional BOC$_2$O (0.15 g; 0.7 mmol) was added at 0° C., and the reaction mixture was stirred at room temperature for 1 hour. CH$_2$Cl$_2$ was added, and the organic phase was extracted with 0.3 M KHSO$_4$ and brine). The organic phase was dried and concentrated to yield 0.78 g of the crude product. NMR indicated that approximately 40% of 2-(2-amino-thiazol-5-ylmethyl)-malonic acid diethyl ester remained. BOC$_2$O (0.6 g; 27.5 mmol) was added to a solution of the crude product (0.78 g), triethyl amine (0.4 mL; 30.1 mmol), 4-(dimethylamino) pyridine (0.34 g; 27.8 mmol) in CH$_2$Cl$_2$ (5 mL) at 0° C. The reaction mixture was stirred at room temperature overnight and the work up procedure was repeated. The crude product (1 g) was purified by flash chromatography (Heptane/EtOAc; 1:1) and HPLC to afford 2-(2-tert-butoxycarbonylamino-thiazol-5-ylmethyl)-malonic acid diethyl ester (184 mg, 17.9%).

(d) 2-(2-tert- Butoxycarbonylamino-thiazol-5-ylmethyl)-malonic acid monoethyl ester 2-(2-tert-Butoxycarbonylamino-thiazol-5-ylmethyl)-malonic acid diethyl ester (158 mg; 0.43 mmol) was dissolved in ethanol (1 mL) and THF (0.5 mL), and a solution of KOH (24 mg; 0.43 mmol) in ethanol (0.14 mL) was added at 0° C. The reaction mixture was stirred at room temperature for 96 hours, and then poured onto ice-water. The aqueous phase was extracted with diethyl ether, acidified to pH 3 by addition of 0.5 M HCl, and extracted with diethyl ether. The combined organic phases were dried and concentrated to yield 2-(2-tert-butoxycarbonylamino-thiazol-5-ylmethyl)-malonic acid monoethyl ester (97 mg, 66.4%).

(e) 2-(2-tert-Butoxycarbonylamino-thiazol-5-ylmethyl)-acrylic acid ethyl ester To a mixture of 2-(2-tert- butoxycarbonylamino-thiazol-5-ylmethyl)-malonic acid monoethyl ester (94 mg; 0.27 mmol), a 36% aqueous solution of formaldehyde (36 μl; 1.2 mmol), CH$_2$Cl$_2$ (0.2 mL) and water (0.2 mL) was added at 0° C. diethyl amine (30 μl; 0.40 mmol). The reaction mixture was stirred at room temperature overnight, poured onto ice-water and extracted with CH$_2$Cl$_2$. The combined organic phases were washed with 5% NaHCO$_3$, dried and concentrated to yield 2-(2-tert-butoxycarbonylamino-thiazol-5-ylmethyl)-acrylic acid ethyl ester (69 mg, 80.9%).

(f) 2-Acetylsulfanylmethyl-3-(2-tert-butoxycarbonylamino-thiazol-5-yl)-propionic acid ethyl ester Triethyl amine (32 μl; 0.23 mmol) was added to a solution of 2-(2-tert-butoxycarbonyl-amino-thiazol-5-ylmethyl)-acrylic acid ethyl ester (67 mg; 0.21 mmol) in thioacetic acid (0.4 mL) at 0° C. The reaction mixture was stirred at room temperature for 48 hours, and then poured onto ice-water. The aqueous layer was extracted with CH$_2$Cl$_2$. The combined organic phases were washed with saturated NaHCO$_3$, dried and concentrated to yield 190 mg of the crude product. The crude product was purified by flash chromatography (Heptane/EtOAc: 1:0→68:32) to yield 2-acetylsulfanylmethyl-3-(2-tert-butoxycarbonyl-amino-thiazol-5-yl)-propionic acid ethyl ester (43 mg, 51.6%).

(g) 3-(2-Amino-thiazol-5-yl)-2-mercaptomethyl-propionic acid

A solution of 2-acetylsulfanylmethyl-3-(2-tert-butoxycarbonylamino-thiazol-5-yl)-propionic acid ethyl ester (43 mg; 0.11 mmol) in concentrated HCl (1.5 mL) was refluxed under argon for 1.5 hours. The reaction mixture was allowed to cool to room temperature and concentrated under reduced pressure to yield 30 mg of the crude product. The crude product was purified by preparative HPLC to afford the title compound (8 mg; 21%) as the hydrochloride salt.

$^1$H NMR (500 MHz, D$_2$O): δ 2.75–3.1 (m, 5H), 7.0 (br s, 1H). MS (+) 219 (M+1).

Abbreviations

Ac=acetate
aq=aqueous
AIBN=α,α'-azoisobutyronitrile
Bn=benzyl
Bu=butyl
Bz=benzoyl
DCC dicyclohexylcarbodiimide
DIAD=diisopropyl azodicarboxylate
DIPEA=diisopropylethylamine
DMAP=N,N-dimethyl amino pyridine
DME=1,2-dimethoxyethane
DMF=dimethylformamide
DMSO=dimethylsulfoxide
EDC=1-(3-dimethylaminopropyl)-3-ethylcarbodiimide
ee=enantiomeric excess
Et=ethyl
EtOAc=ethyl acetate
EtOH=ethanol
h=hour
HOAc=acetic acid
HOBt=1-hydroxybenzotriazol
HPLC=high performance liquid chromatography
KHMDS=potassium bis(trimethylsilyl)amide
LDA=lithium diisopropylamide
MCPBA=3-chloroperbenzoic acid
Me=methyl
MeOH=methanol
min=minutes
PMB=4-methoxybenzyl
Ph=phenyl
Pr=propyl
PyBOP=(benzotriazol-1-yloxy)tripyrrolidinophosphonium hexafluorophosphate
TEA=triethylamine
TFA=trifluoroacetic acid
THF=tetrahydrofuran
Tos=toluene-4-sulfonyl

What is claimed is:

1. A compound of Formula I

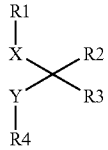

(I)

or a pharmaceutically acceptable salt or solvate thereof, or a solvate of such a salt,
wherein:
R$_1$ is pyridyl substituted with one or more basic groups;
R$_2$ is selected from the group consisting of H, acyl, acylamino, alkyl, alkylcarbamoyl, alkylthio, alkoxy, aroyl, aroylamino, aryloxy, arylthio, amidino, amino, aryl, carbamoyl, carboxy, cyano, cycloalkyl, formyl, guanidino, halogen, heterocyclyl, hydroxy, oxo, nitro, thiol, a Z$_2$N—CO—O— group, a ZO—CO—NZ— group, and a Z$_2$N—CO—NZ— group;
R$_3$ is selected from the group consisting of COOR$_5$, SO(OR$_5$), SO$_3$R$_5$, P=O(OR$_5$)$_2$, B(OR$_5$)$_2$, P=OR$_5$ (OR$_5$), tetrazole, and a carboxylic acid isostere which is an acidic group having a pKa of from about −5 to about 25;

R$_4$ is SH, S—CO—C$_1$–C$_6$ alkyl, or S—CO-aryl;

R$_5$ is H, C$_1$–C$_6$ alkyl, or aryl;

R$_6$ is H or C$_1$–C$_6$ alkyl;

X is selected from the group consisting of O, S, SO, SO$_2$, C(Z)$_2$,

N (Z), NR$_6$SO$_2$, SO$_2$NR$_6$, NR$_6$CO, and CONR$_6$;

Y is C(Z)$_2$; and

Z is independently selected from the group consisting of H, C$_1$–C$_6$ alkyl, aryl, cycloalkyl, and heterocyclyl.

2. The compound according to claim 1, or a pharmaceutically acceptable salt or solvate thereof, or a solvate of such a salt,
wherein:

R$_2$ is selected from the group consisting of H, acyl, acylamino, alkyl, alkylcarbamoyl, alkylthio, alkoxy, aroyl, aroylamino, aryloxy, arylthio, amidino, amino, aryl, carbamoyl, carboxy, cyano, cycloalkyl, formyl, guanidino, halogen, heterocyclyl, hydroxy, oxo, nitro, thiol, Z$_2$N—CO—O—, ZO—CO—NZ—, and Z$_2$N—CO—NZ—;

R$_3$ is COOR$_5$;

R$_4$ is SH, S—CO—C$_1$–C$_6$ alkyl, or S—CO-aryl;

R$_5$ is H, C$_1$–C$_6$ alkyl, or aryl;

R$_6$ is H or C$_1$–C$_6$ alkyl;

X is selected from the group consisting of O, S, SO, SO$_2$, C(Z)$_2$,

N(Z), NR$_6$SO$_2$, SO$_2$NR$_6$, and CONR$_6$;

Y is C(Z)$_2$; and

Z is independently selected from the group consisting of H, C$_1$–C$_6$ alkyl, aryl, cycloalkyl and heterocyclyl.

3. The compound according to claim 1, or a pharmaceutically acceptable salt or solvate thereof, or a solvate of such a salt,
wherein:

R$_2$ is selected from the group consisting of H, C$_1$–C$_3$ alkyl, amino, halogen, and hydroxy;

R$_3$ is COOR$_5$;

R$_4$ is SH, S—CO—C$_1$–C$_6$ alkyl, or S—CO-aryl;

R$_5$ is H, C$_1$–C$_6$ alkyl, or aryl;

X is C(Z)$_2$;

Y is C (Z)$_2$; and

Z is independently H or C$_1$–C$_6$ alkyl.

4. The compound according to claim 1, or a pharmaceutically acceptable salt or solvate thereof, or a solvate of such a salt,
wherein:

R$_2$ is H, F, or C$_1$ alkyl;

R$_3$ is COOR$_5$;

R$_4$ is SH, S—CO—C$_1$–C$_6$ alkyl, or S—CO-aryl;

R$_5$ is H, C$_1$–C$_6$ alkyl, or aryl;

X is C (Z)$_2$;

Y is C(Z)$_2$; and

Z is independently H or C$_1$–C$_6$ alkyl.

5. The compound according to claim 1, or a pharmaceutically acceptable salt or solvate thereof, or a solvate of such a salt, wherein:

R$_2$ is H, F, or C$_1$ alkyl;

R$_3$ is COOR$_5$;

R$_4$ is SH;

R$_5$ is H;

X is CHZ;

Y is CHZ; and

Z is independently H or C$_1$–C$_6$ alkyl.

6. The compound according to any one of claims 1–5, wherein the basic group is selected from the group consisting of amino, amidino, and guanidino.

7. A pharmaceutical formulation comprising a compound according to any one of claims 1 to 5 as active ingredient in combination with a pharmaceutically acceptable adjuvant, diluent or carrier.

8. A pharmaceutical formulation, comprising:

(i) a compound of Formula I according to claim 1, or a pharmaceutically acceptable salt or solvate thereof, or a solvate of such a salt; and (ii) one or more antithrombotic agents selected from the group consisting of an antiplatelet agent, thromboxane receptor inhibitor, synthetase inhibitor, fibrinogen receptor antagonist, prostacyclin mimetic, phosphodiesterase inhibitor, and an ADP-receptor (P$_2$T) antagonist, in admixture with a pharmaceutically acceptable adjuvant, diluent, or carrier.

9. A method for inhibiting carboxypeptidase U, comprising administering an effective amount of a compound according to any one of claims 1–5.

10. A method both for inhibiting carboxypeptidase U and for achieving an antithrombotic effect via a different mechanism, which method comprises administering a therapeutically effective total amount of:

(i) a compound of Formula I according to claim 1, or a pharmaceutically acceptable salt or solvate thereof, or a solvate of such a salt, in admixture with a pharmaceutically acceptable adjuvant, diluent, or carrier; and (ii) one or more antithrombotic agents selected from the group consisting of an antiplatelet agent, thromboxane receptor inhibitor, synthetase inhibitor, fibrinogen receptor antagonist, prostacyclin mimetic, phosphodiesterase inhibitor, and an ADP-receptor (P$_2$T) antagonist, in admixture with a pharmaceutically acceptable adjuvant, diluent, or carrier.

11. A method both for inhibiting carboxypeptidase U and for achieving an antithrombotic effect via a different mechanism, which method comprises administering the formulation according to claim 8.

12. A method for treatment of thrombosis and hypercoagulability, comprising administering to a patient in need of such treatment an effective amount of a compound according to any one of claims 1–5.

13. A process for the preparation of a compound according to claim 1, wherein X is C(Z)$_2$, and R$_2$ is H, comprising the step of:

reacting a compound of Formula VI,

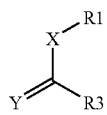

(VI)

wherein $R_1$, $R_3$ and Y are as defined in claim 1 and X is $C(Z)_2$, with a compound of Formula IX,

R5-SH (IX)

wherein $R_5$ is a protecting group, optionally in the presence of a base or a free-radical initiator.

14. A process for the preparation of a compound according to claim 1, wherein Y is $CH_2$, and X is O, S, $C(Z)_2$, or N(Z), comprising the step of:

reacting a compound of Formula XIV,

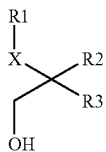

(XIV)

wherein $R_1$, $R_2$, and $R_3$ are as defined in claim 1, and X is O, S, $C(Z)_2$, or N(Z), with a compound of general Formula IX,

R5-SH (IX)

wherein $R_5$ is a protecting group, in the presence of a suitable reagent, under standard conditions.

15. A process for the preparation of a compound according to claim 1, wherein X is $NR_6CO$ or $NR_6SO_2$, comprising the step of:

reacting a compound of Formula XV,

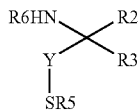

(XV)

wherein $R_2$, $R_3$, $R_6$ and Y are as defined in claim 1 and $R_5$ is a protecting group, with a compound of Formula XVI,

R1-X (XVI)

wherein $R_1$ is as defined in claim 1 and X is COOH or $SO_2Cl$, in the presence of a coupling reagent, under standard conditions.

16. The process according to claim 13, wherein the protecting group is selected from the group consisting of acetate (Ac), benzoyl (Bz), benzyl (Bn), and 4-methoxybenzyl (PMB).

17. The process according to claim 13, wherein the base is selected from the group consisting of NaOMe, NaH, and triethylamine.

18. The process according to claim 13, wherein the free-radical initiator is α,α'-azoisobutyronitrile (AIBN).

19. The process according to claim 14, wherein the protecting group is acetate (Ac) or benzoyl (Bz).

20. The process according to claim 14, wherein the reagent is $PPh_3$/diisopropyl azodicarboxylate (DIAD).

21. The process according to claim 15, wherein the protecting group is selected from the group consisting of acetate (Ac), benzoyl (Bz), benzyl (Bn), and 4-methoxybenzyl (PMB).

22. The process according to claim 15, wherein the coupling reagent is selected from the group consisting of:
  (i) (benzotriazol-1-yloxy)tripyrrolidinophosphonium hexafluorophosphate (PyBOP)/diisopropylethylamine (DIPEA);
  (ii) dicyclohexylcarbodiimide (DCC)/1-hydroxybenzotriazol (HOBt);
  (iii) 1-(3-dimethylaminopropyl)-3-ethylcarbodiimide (EDC)/triethylamine (TEA)/N,N-dimethyl amino pyridine (DMAP); and
  (iv) pyridine.

23. A kit of parts comprising:
  (i) a pharmaceutical formulation comprising a compound of Formula I according to claim 1, or a pharmaceutically acceptable salt or solvate thereof, or a solvate of such a salt, in admixture with a pharmaceutically acceptable adjuvant, diluent, or carrier; and
  (ii) a pharmaceutical formulation comprising one or more antithrombotic agents selected from the group consisting of an antiplatelet agent, thromboxane receptor inhibitor, synthetase inhibitor, fibrinogen receptor antagonist, prostacyclin mimetic, phosphodiesterase inhibitor, and an ADP-receptor ($P_2T$) antagonist,
  in admixture with a pharmaceutically acceptable adjuvant, diluent, or carrier,
wherein compound (i) and agent (ii) are each formulated for administration in conjunction with the other.

* * * * *